US009150621B2

(12) United States Patent
Jennings

(10) Patent No.: US 9,150,621 B2
(45) Date of Patent: Oct. 6, 2015

(54) MUTANT BACTERIAL GLYCOPROTEINS AND USES THEREOF

(75) Inventor: Michael Paul Jennings, Brisbane (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 13/061,492

(22) PCT Filed: Aug. 28, 2009

(86) PCT No.: PCT/AU2009/001111
§ 371 (c)(1),
(2), (4) Date: Jul. 12, 2011

(87) PCT Pub. No.: WO2010/022462
PCT Pub. Date: Mar. 4, 2010

(65) Prior Publication Data
US 2011/0262476 A1   Oct. 27, 2011

(30) Foreign Application Priority Data

Aug. 28, 2008 (AU) ................. 2008904429

(51) Int. Cl.
*C07K 14/22* (2006.01)
*A61K 39/095* (2006.01)
*A61K 38/00* (2006.01)
*C07K 16/22* (2006.01)
*C12N 9/06* (2006.01)
*C07K 16/12* (2006.01)
*C12P 21/00* (2006.01)

(52) U.S. Cl.
CPC ............... *C07K 14/22* (2013.01); *A61K 39/095* (2013.01); *C07K 16/1217* (2013.01); *C12N 9/0044* (2013.01); *C12P 21/005* (2013.01); *C12Y 107/02001* (2013.01); *A61K 38/00* (2013.01)

(58) Field of Classification Search
None
See application file for complete search history.

(56) References Cited

U.S. PATENT DOCUMENTS 6,872,398 B2   3/2005 Castric et al.
6,936,261 B2 * 8/2005 Granoff et al. ............ 424/249.1

FOREIGN PATENT DOCUMENTS

| WO | WO 02/079243 | 10/2002 |
| WO | WO2006138238 | * 12/2006 |
| WO | WO 2007/128136 A1 | 11/2007 |
| WO | WO 2008/093165 A2 | 8/2008 |
| WO | WO2008135446 | * 11/2008 |

OTHER PUBLICATIONS

DYKDDDDK Tag antibody. Nov. 23, 2007. Retrieved from http://web.archive.org/web/20071123122432/http://www.cellsignal.com/products/2368.html.*
Boulanger et al. J. Mol. boil 315:1111-1127.*
"Crystal Structure of the Soluble Domain of AniA from Neisseria gonorrhoeae" retrieved on Oct. 31, 2014 from Protein Data Bank http://www.rcsb.org/pdb/explore.do?structureId=1KBW.*
Stefanelli et al. IUBMB Life, vol. 60, pp. 629, 2008.*
Chamot-Rooke et al., "Alternative *Neisseria* spp. Type IV pilin glycosylation with a glyceramido acetamido trideoxyhexose residue," *PNAS*, 104(37):14783-14788, 2007.
Ku et al., "The pilin O-glycosylation pathway of pathogenic *Neisseria* is a general system that glycosylates AniA, an outer membrane nitrite reductase," *BBRC*, 378:84-89, 2009.
Boulanger et al., "Crystal Structure of the Soluble Domain of the Major Anaerobically Induced Outer Membrane Protein (AniA) from Pathogenic *Neisseria*: A New Class of Copper-containing Nitrite Reductases," *J. Mol. Biol.*, vol. 315, pp. 1111-1127, 2002.
Database UniProt Accession No. Q27PS6, 2006 (one page).
Database UniProt Accession No. Q5F7A4, 2005 (one page).
Hoehn et al., "The Major Anaerobically Induced Outer Membrane Protein of *Neisseria gonorrhoeae*. Pan 1, is a Lipoprotein," *Infection and Immunity*, vol. 60, pp. 4704-4708, 1992.
Mellies et al., "The *Neisseria gonorrhoeae* Gene *aniA* Encodes an Inducible Nitrite Reductase," *Molecular and General Genetics*, vol. 256, pp. 525-532, 1997.
Stefanelli et al., "Molecular Characterization of Nitrite Reductase Gene (*aniA*) and Gene Product in *Neisseria meningitidis* Isolates: Is *aniA* Essential for Meningococcal Survival?" *IUBMB Life*, vol. 60, pp. 629-636, 2008.

* cited by examiner

*Primary Examiner* — Oluwatosin Ogunbiyi
(74) *Attorney, Agent, or Firm* — Klarquist Sparkman, LLP

(57) ABSTRACT

The present invention relates to the use of mutant glycoproteins from pathogenic bacteria lacking one or more phosphorylcholine and/or glycosylation post-translational modifications as immunogens. These post-translational modifications act as masking structures that elicit an immune response which does not confer protection on an infected individual. The removal or modification of these masking structures alters the protein such that it elicits a stronger immune response to the protein and/or the bacterial pathogen. Particular examples are pilin proteins and nitrite reductase glycoproteins of *Neisseria* bacteria.

10 Claims, 21 Drawing Sheets

FIG. 5A, continued

```
             ....|....|....|....|....|....|....|....|....|....|....|....|....|....|....|....|....|....|....|....|
                    110        120        130        140        150        160        170        180        190        200
MC58         YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
C311         YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
4/88         YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
AK50         YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
BZ83         YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
FG327        YIYWTFDGDV PGRV RVREC DTVEVEFSNN PSSTVPHNVD FHAATGQGGG AAATFTAPGR TSTFSFKA Q PGLYIYICAV APVCMHIANG MYCLILVEPK
EG329        YRYWTFDCDV PCRV RVREC DTVEVEFSNN PSSTVPHNVD FHAATGQCCC AAATFTAPGR TSTFSFKA Q PCLYIYHCAV APVCMHIANC MYCLILVEPK
NGPD24       YRYWTFDGDV PGRV RVREG DTVEVEFSNN PSSIVPHNVD FHAATGQGGG AAATFTAPGR TSTFSFKA Q PGLYIYHCAV APVGMHIANG MYGLILVEPK
NG144/82     YRYWTFDGDV PGRV RVREG DIVEVEFSNN PSSIVPHNVD FHAATGQGGG AAATFTAPGR TSTHSFKA Q PGLYIYHCAV APVGMHIANG MYGLILVEPK
BZ169        YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
44/76        YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
Z2491        YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
107          YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
3/88         YRYWTFDCDV PCRV RVREC DTVEVEFSNN PSSTVPHNVD FHAATCQCCC AAATFTAPGR TSTFSFKA Q PCLYIYHCAV APVCMHIANC MYCLILVEPK
BZ133        YRYWTFDGDV PGRV RVREG DIVEVEFSNN PSSIVPHNVD FHAATGQGGG AAATFTAPGR TSTFSFKA Q PGLYIYHCAV APVGMHIANG MYGLILVEPK
528          YRYWTFDGDV PGRV RVREG DTVEVEFSNN PSSTVPHNVD FHAATGQGGG AAATFTAPGR TSTFSFKA Q PGLYIYHCAV APVGMHIANG MYGLILVEPK
Fam18        
10C0         
NGP20        
42R          
B6116/77     
2970         
DK353        
BZ210        
BZ157        
BZ163        
MPJ31B       
MPJ1B        
MPJ8D        
AK2          TATGHLTATF RVA*
E38          YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
E15          YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
E36          YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
40C          YHYWTFDCDV PGRV RVREG DTVEVEFSNN PSSTVPHNVD FHAATGQGGG AAATFTAPGR TSTFSFKA Q ACLYIYHCAV APVCMHIANC MYCLILVEPK
BZ47         YHYWTFDGDV PGRV RVREG DTVEVEFSNN PSSTVPHNVD FHAATCQCCC AAATFTAPGR TSTFSFKA Q AGLYIYHCAV APVCMHIANG MYGLILVEPK
931905       YHYWTFDGDV PGRV RVREG DIVEVEFSNN PSSIVPHNVD FHAATGQGGG AAATH TAPGR TSIHSFKA Q AGLYIYHCAV APVGMHIANG MYGLILVEPK
88/03415     YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
M4C/94       YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
351          YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
BZ198        YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
MPJ3B        YHYWTFDGDV PGRV RVREG DTVEVEFSNN PSSTVPHNVD FHAATGQGGG AAATFTAPGR TSTFSFKA Q AGLYIYHCAV APVGMHIANG MYGLILVEPK
```

FIG. 5A, continued

```
                    ....|....|....|....|....|....|....|....|....|....|....|....|....|....|....|....|....|....|....|
                        210        220        230        240        250        260        270        280        290        300
MC58         EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
C311         EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
4/88         EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
AK50         EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
E83          EGLPKVDKEF YIVQGDFYTK GKKGAQGLQP FDMDKRATAEQ PEYVVFNGHV GA_AGDNALK AKAGETVRMY VGNGGPNLVS SFHVTGEIFD KVYVEGGK_I
EG327        EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
EG329        EGLPKVDKEF YIVQGDFYTK GKKGAQGLQP FDMDKAVAEQ PEYVVFNCHV CA_ACDNALK AKAGETVRMY VCNCCPNLVS SFHVIGEIFD KVYVECCK_I
NGPD24       EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
NG144/82     EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
B2169        EGLPKVDKEF YIVQGDFYTK GKKGAQGLQP FDMDKAVAEQ PEYVVFNGIIV GA_AGDNALK AKAGETVRMY VGNGGPNLVS SFHVIGEIFD KVYVEGGK_I
44/76        EGLPKVDKEF YIVQGDFYTK GKKGAQGLQP FDMDKAVAEQ PEYVVFNGHV GA_AGDNALK AKAGETVRMY VGNGGPNLVS SFHVIGEIFD KVYVEGGK_I
Z2491        EGLPKVDKEF YIVQGDFYTK GKKGAQGLQP FDMDKAIAEQ PEYVVFNGHV GA_AGDNALK AKAGETVRMY VGNGGPNLVS SFHVIGEIFD KVYVEGGK_I
1C7          EGLPKVDKEF YIVQGDFYTK GKKGAQGLQP FDMDKATAEQ PEYVVFNGHV GA_AGDNALK AKAGETVRMY VGNGGPNLVS SFHVTGEIFD KVYVEGGK_T
3/88         EGLPKVDKEF YIVQGDFYTK CKKCAQCLQP FDMDKAIAEQ PEYVVFNCHV CA_ACDNALK AKACCPNALK AKACETVRMY VCNCCPNLVS SFHVICEIFD KVYVECCK_I
B2133        EGLPKVDKEF YIVQGDFYTK GKKGAQGLQP FDMDKAIAEQ PEYVVFNGHV GA_AGDNALK AKAGETVRMY VGNGGPNLVS SFHVIGEIFD KVYVEGGK_I
528          EGLPKVDKEF YIVQGDFYTK GKKGAQGLQP FDMDKAIAEQ PEYVVFNGHV GA_AGDNALK AKAGETVRMY VGNGGPNLVS SFHVIGEIFD KVYVEGGK_I
Fam18
1000
NCP20
42B
B6116/77
29/0
DK353
B2210
B2157
B2163
MPJ31B
MPJ1B
MPJ8D
AK22
E38          EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
E15          EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
E36          EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
40C          EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
B247         EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
931905       EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
88/03415     EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
M4C/94       EGLPKVDKEF YIVQGDFYTK GKKGAQGLQP FDMDKAIAEQ PEYVVFNGIIV GS_AGDNALK AKAGETIRMY VGNGGPNLVS SFHVIGEIFD KVYVEGGK_I
351          EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
E4198        EGLPKVDKEF YIVQGDFYTK GKKGAQGLQP FDMDKAIAEQ PEYVVFNGHV GS_AGDNALK AKAGETIRMY VGNGGPNLVS SFHVIGEIFD KVYVEGGK_I
MPJ3B        EGLPKVDKEF YIVQGDFYTK GKKGAQGLQP FDMDKATAEQ PEYVVFNGHV GS_AGDNALK AKAGETIRMY VGNGGPNLVS SFHVIGEIFD KVYVEGGK_T
```

FIG. 5A, continued

```
             310        320        330        340        350        360        370        380        390        400
             ....|....|....|....|....|....|....|....|....|....|....|....|....|....|....|....|....|....|....|....|
MC58         NENVQSTIVP AGGSAIVEFK VDTPGSYTLV DHSTFRAFNK GALGQLKVEG AENPEIMTQK LSDTAYAGNG AAPAASAPAA SAPAASASEK SVY*
C311         NENVQSTIVP AGGSAIVEFK VDTPGSYTLV DHSTFRAFNK GALGQLKVEG AENPEIMTQK LSDTAYAGNG AAPAASAPAA SAPAASASEK SVY*
4/88         NENVQSTIVP AGGSAIVEFK VDTPGSYTLV DHSTFRAFNK GALGQLKVEG AENPEIMTQK LSDTAYAGNG AAPAASAPAA SAPAASASEK SVY*
AK50         NENVQSTIVP AGGSAIVEFK VDTPGSYTLV DHSTFRAFNK GALGQLKVEG AENPEIMTQK LSDTAYAGNG AAPAASAPAA SAPAASASEK SVY*
BZ83         NENVQSTIVP AGGSAIVEFK VDTPGSYTLV DHSTFRAFNK GALGQLKVE- ---------- ---------- ---------- ---------- ----
EG327        NENVQSTIVP AGGSAIVEFK VDTPGSYTLV DHSTFRAFNK GALGQLKVE- ---------- ---------- ---------- ---------- ----
EG329        NENVQSTIVP AGGSAIVEFK VDTPGSYTLV DHSTFRAFNK GALGQLKVE- ---------- ---------- ---------- ---------- ----
NCPB24       NENVQSTIVP AGGSAIVEFK VDTPGSYTLV DHSTFRAFNK GALGQLKVE- ---------- ---------- ---------- ---------- ----
NG144/82     NENVQSTIVP AGGSAIVEFK VDTPGSYTLV DISTFRAFNK GALGQLKVE- ---------- ---------- ---------- ---------- ----
BZ169        NENVQSTIVP ACCSAIVEFK VDTPGSYTLV DHSTFRAFNK CALGQLKVE- ---------- ---------- ---------- ---------- ----
44/76        NENVQSTIVP AGGSAIVEFK VDTPGSYTLV DHSTFRAFNK GALGQLKVE- ---------- ---------- ---------- ---------- ----
Z2491        NRNVQSTIVP AGGSAIVEFK VDTPGSYTLV DHSTFRAFNK GALGQLKVRG AENPEIMTQK LSDTAYAGNG AAPAASAPAA SAPAASAPAK GDY*
107          NENVQSTIVP AGGSAIVEFK VDTPGSYTLV DHSTFRAFNK GALGQLKVE- ---------- ---------- ---------- ---------- ----
3/88         NENVQSTIVP AGGSAIVEFK VDTPGSYTLV DHSTFRAFNK GALGQLKVE- ---------- ---------- ---------- ---------- ----
BZ133        NENVQSTIVP AGGSAIVEFK VDTPGSYTLV DHSTFRAFNK GALGQLKVE- ---------- ---------- ---------- ---------- ----
528          NENVQSTIVP AGGSAIVEFK VDTPGSYTLV DISTFRAFNK GALGQLKVE- ---------- ---------- ---------- ---------- ----
Far18
1000
NGP20
42B
R6116/77
2970
DK353
BZ210
BZ157
BZ163
MPJ31B
MPJ1B
MPJ8B
AK22         NENVQSTIVP ACCSAIVEFK VDTPGSYTLV DHSTFRAFNK GALGQLKVE- ---------- ---------- ---------- ---------- ----
E38          NENVQSTIVP AGGSAIVEFK VDTPGSYTLV DHSTFRAFNK GALGQLKVE- ---------- ---------- ---------- ---------- ----
L15          NENVQSTIVP AGGSAIVEFK VDTPGSYTLV DHSTFRAFNK GALGQLKVE- ---------- ---------- ---------- ---------- ----
E36          NENVQSTIVP AGGSAIVEFK VDTPGSYTIV DHSTFRAFNK GAIGQLKVE- ---------- ---------- ---------- ---------- ----
400          NENVQSTIVP AGGSAIVEFK VDTPGSYTLV DHSTFRAFNK GALGQLKVE- ---------- ---------- ---------- ---------- ----
DZ47         NENVQSTIVP AGGSAIVEFK VDTPGSYTLV DHSTFRAFNK GALGQLKVE- ---------- ---------- ---------- ---------- ----
931905       NENVQSTIVP AGGSAIVEFK VDTPGSYTLV DHSTFRAFNK GALGQLKVE- ---------- ---------- ---------- ---------- ----
88/03415     NENVQSTIVP AGGSAIVEFK VDTPGSYTLV DHSTFRAFNK GALGQLKVE- ---------- ---------- ---------- ---------- ----
M40/94       NENVQSTIVP AGGSAIVEFK VDTPGSYTLV DHSTFRAFNK GALGQLKVE- ---------- ---------- ---------- ---------- ----
351          NENVQSTIVP AGGSAIVEFK VDTPGSYTLV DHSTFRAFNK GALGQLKVE- ---------- ---------- ---------- ---------- ----
BZ198        NRNVQSTIVP AGGSAIVEFK VDTPGSYTLV DHSTFRAFNK GAIGQLKVF- ---------- ---------- ---------- ---------- ----
MPJ3B        NENVQSTIVP AGGSAIVEFK VDLPGSYTLV DHSTFRAFNK GALGQLKVE- ---------- ---------- ---------- ---------- ----
```

FIG. 5B, continued

| | 110 | 120 | 130 | 140 | 150 | 160 | 170 | 180 | 190 | 200 |
|---|---|---|---|---|---|---|---|---|---|---|
| MC58 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| C311 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 4/88 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| AK5C | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| BZ83 | YHYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| EG327 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| EG329 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| NGPB24 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| NG144/82 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| BZ169 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 44/76 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| Z2491 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 107 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 3/88 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| BZ133 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 528 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| Fam18 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 100C | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| NGP20 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| 42B | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| B6116/77 | YRYWTFDGDV | PGRMIRVREG | DTVEVEFSNN | PSSIVPIINVD | FHAAIGQGGG | AAAITFTAPGR | TSTFSLKALQ | PGLYIYHCAV | APVGMHIANG | MYGLIIVEPK |
| 297C | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| DK353 | YRYWTFDGDV | PGRMIRVREG | DTVEVEFSNN | PSSIVPHNVD | FIIAAIGQGGG | AAAITFTAPGR | TSTFSFKALQ | PGLYIYHCAV | APVGMHIANG | MYGLIIVEPK |
| BZ210 | YRYWTFDGDV | PGRMIRVREG | DTVEVEFSNN | PSSIVPHNVD | FHAAIGQGGG | AAAITFTAPGR | TSTTSFKALQ | PGLYIYHCAV | APVGMHIANG | MYGLIIVEPK |
| BZ157 | YRYWTFDGDV | PGRMIRVREG | DTVEVEFSNN | PSSIVPIINVD | FIIAAIGQGGG | AAAITFTAPGR | TSTTSFKALQ | PGLYIYHCAV | APVGMIIANG | MYGLIIVEPK |
| BZ163 | YRYWTFDGDV | PGRMIRVREG | DTVEVEFSNN | PSSIVPIINVD | FIIAAIGQGGG | AAAITFTAPGR | TSTTSFKALQ | PGLYIYHCAV | APVGMIIANG | MYGLIIVEPK |
| M2J31B | YRYWTFDGDV | PGRMIRVREG | DTVEVEFSNN | PSSIVPIINVD | FIIAAIGQGGG | AAAITFTAPGR | TSTFSFKALQ | PGLYIYHCAV | APVGMIIANG | MYGLIIVEPK |
| M2J1B | YRYWTFDGDV | PGRMIRVREG | DTVEVEFSNN | PSSIVPIINVD | FIIAAIGQGGG | AAAITFTAPGR | TSTFSFKALQ | PGLYIYHCAV | APVGMIIANG | MYGLIIVEPK |
| M2J8B | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMIIANG | MYGLIIVEPK |
| AK22 | YRYWTFDGDV | PGRMIRVREG | DTVEVEFSNN | PSSIVPHNVD | FHAAIGQGGG | AAAITFTAPGR | TSTFSFKALQ | PGLYIYHCAV | APVGMHIANG | MYGLIIVEPK |
| H38 | YIIYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| H15 | YRYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| H36 | YHYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| 400 | YIIYWTFDGDV | PGRMIRVREG | DTVEVEFSNN | PSSIVPHNVD | FIIAAIGQGGG | AAAITFTAPGR | TSTFSFKALQ | AGLYIYIICAV | APVGMIIANG | MYGLIIVEPK |
| BZ47 | YRYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| 9.31.1905 | YHYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| 88/03415 | YHYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| M40/94 | YHYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |
| 351 | YIIYWTFDGDV | PGRMIRVREG | DTVEVEFSNN | PSSIVPHNVD | FIIAAIGQGGG | AAAITFTAPGR | TSTFSFKALQ | AGLYIYIICAV | APVGMIIANG | MYGLIIVEPK |
| BZ198 | YIIYWTFDGDV | PGRMIRVREG | DTVEVEFSNN | PSSIVPHNVD | FIIAAIGQGGG | AAAITFTAPGR | TSTFSFKALQ | AGLYIYIICAV | APVGMIIANG | MYGLIIVEPK |
| M2J3B | YHYWTFDGDV | PGRMIRVREG | DTVEVEFSNN | PSSIVPHNVD | FHAAIGQGGG | AAAITFTAPGR | TSTFSFKALQ | AGLYIYHCAV | APVGMHIANG | MYGLIIVEPK |

FIG. 5B, continued

| | | | | | | | | | |
|---|---|---|---|---|---|---|---|---|---|
| | 210 | 220 | 230 | 240 | 250 | 260 | 270 | 280 | 290 | 300 |
| MC58 | EGLPKVDKE$\ddot{\text{F}}$ | Y-VQGDFYTK | GKKGAQGQ̊LQP | FDMDKAV̊AEQ | PEYVVFNGHV | GAIAGDNALK | AKAGETVRMY | VGNGGPNLVS | SFHV-GSIFD | KVYVEGGKLI |
| C311 | EGLPKVDKEF | Y-VQGDEYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| 4/88 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| AK50 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| B783 | EGLPKVDKEF | Y-VQGDEYTK | GKKGAQGLQP | FDMDKAVAEQ | PFYVVFNCHV | GAIACDNALK | AKAGETVRMY | VGNCGPNLVS | SFHV-GSIFD | KVYVECGKLI |
| EG327 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVFGGKLI |
| EG329 | EGLPKVDKEF | Y-VQGDFYIK | GKKCAQGLQP | FDMDKAVAEQ | PLYVVENCHV | CAIAGDNAIK | AKAGETVRMY | VGNCCPNLVS | SFHV-GSIFD | KVYVECCKLI |
| NGPB24 | EGLPKVDKEF | Y-VQGDEYIK | GKKGAQGLQP | FDMDKAVAEQ | PEYVVFNGHV | CAIACDNALK | AKAGETVRMY | VGNCCPNLVS | SFHV-GSIFD | KVYVFGGKLI |
| NG144/82 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVFGGKLI |
| BZ169 | EGLPKVDKEF | Y-VQGDFYTK | GKKGAQGLQP | FDMDKAIAEQ | PFYVVFNGHV | GATAGDNALK | AKAGETVRMY | VGNGGPNLVS | SFHV-GSIFD | KVYVFGGKLT |
| 44/76 | EGLPKVDKEF | Y-VQGDFYTK | GKKGAQGLQP | FDMDKAIAFQ | PEYVVFNGHV | GAIAGDNALK | AKAGETVRMY | VGNGGPNLVS | SFHV-GTIFD | KVYVFGGKLI |
| Z2491 | EGLPKVDKEF | Y-VQGDFYTK | GKKGAQGLQP | FDMDKAVAEQ | PEYVVFNGHV | GAIAGDNAIK | AKAGETVRMY | VGNGGPNLVS | SFHV-GSIFD | KVYVFGGKLI |
| 1C7 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| 3/88 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| BZ133 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVFGGKLI |
| 528 | EGLPKVDKEF | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| Fam18 | EGLPKVDKEF | Y-VQGDFYTK | GKKGAQGLQP | FDMDKAVAEQ | PEYVVFNGHV | GSIAGDNALK | AKAGETVRMY | VGNGGPNLVS | SFHV-GSIFD | KVYVEGGKLI |
| 1C00 | EGLPKVDKEF | Y-VQGDFYTK | GKKGAQGPQP | FDMDKAVAEQ | PEYVVFNGHV | GSIAGDNALK | AKAGETVRMY | VGNGGPNLVS | SFHV-GSIFD | KVYVFGGKLI |
| NGF20 | EGLPKVDKEF | Y-VQGDFYTK | GKKGAQGLQP | FDMDKAVAEQ | PEYVVFNGIIV | GSIAGDNALK | AKAGETVRMY | VGNGGPNLVS | SFHV-GSIFD | KVYVEGGKLI |
| 42B | EGLPKVDKES | Y-VQGDFYIK | GKKGAQGLQP | FDMDKAVAEQ | PEYVVFNGIIV | GAIAGDNALK | AKAGETVRMY | VGNGGPNLVS | SFIIV-GSIFD | KVYVEGGKLI |
| B6116/77 | EGLPKVDKES | Y-VQGDFYTK | GKKGAQGLQP | FDMDKAVAEQ | PEYVVFNGHV | GAIAGDNALK | AKAGETVRMY | VGNGGPNLVS | SFIIV-GSIFD | KVYVEGGKLI |
| 2970 | EGLPKVDKES | Y-VQGDFYTK | GKKGAQGLQP | FDMDKAVAEQ | PEYVVFNGHV | GAIAGDNALK | AKAGETVRMY | VGNGGPNLVS | SFHV-GSIFD | KVYVEGGKLI |
| DK353 | EGLPKVDKES | Y-VQGDFYTK | GKKGAQGLQP | FDMDKAVAEQ | PEYVVFNGHV | GSIAGDNALK | AKAGETVRMY | VGNGGPNLVS | SFHV-GSIFD | KVYVEGGKLI |
| BZ210 | EGLPKVDKES | Y-VQGDFYTK | GKKGAQGLQP | FDMDKAVAEQ | PEYVVFNGHV | GAIAGDNALK | EKAGETVRMY | VGNGGPNLVS | SFHV-GSIFD | KVYVEGGKLI |
| B7157 | EGLPKVDKES | Y-VQGDFYTK | GKKGAQGLQP | FDMDKAVAEQ | PFYVVFNGHV | GAIAGDNALK | AKAGETIRMY | VGNGGPNLVS | SFHV-GSIFD | KVYVEGGKLI |
| BZ163 | EGLPKVDKES | Y-VQGDFYTK | GKKGAQGLQP | FDMDKAVAEQ | PEYVVFNGHV | GAIAGDNALK | AKAGETIRMY | VGNGGPNLVS | SFHV-GSIFD | KVYVEGGKLI |
| MPJ31B | EGTPKVDKES | Y-VQGDFYIK | GKKGAQGLQP | FDMDKAVAEQ | PEYVVFNGHV | GSIAGDNALK | AKAGETIRMY | VGNGGPNLVS | SFHV-GSIFD | KVYVEGGKLI |
| MPJ1B | EGTPKVDKES | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| MPJ8B | EGLPKVDKES | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVFGGKLI |
| AK22 | EGLPKVDKES | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| H38 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| H15 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| II36 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| 4C0 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| BZ47 | EGLPKVDKEF | Y-VQGDFYTK | GKKGAQGLQP | FDMDKAVAEQ | PEYVVFNGHV | GSIAGDNALK | AKAGETIRMY | VGNGGPNLVS | SFHV-GSIFD | KVYVEGGKLI |
| 931905 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| 88/03415 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| M10/94 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| 351 | EGLPKVDKES | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| BZ198 | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |
| MPJ3B | EGLPKVDKEF | Y-VQGDFYTK | GKKGAQGLQP | FDMDKAIAEQ | PEYVVFNGHV | GSIAGDNALK | AKAGETIRMY | VGNGGPNLVS | SFHV-GSIFD | KVYVEGGKLI |

FIG. 5B, continued

```
              |....|....|....|....|....|....|....|....|....|....
                  310        320        330        340        350        360        370        380        390        400
MC58          NENVQSTIVP ACCSAIVEFK VDIPGSYTLV DHSIFRAFNK GALGQLKVEC AENPEIMTQK LSDTAYAGNG AAPAASAPAA SAPAASASEK SVY*
C311          NENVQSTIVP AGGSAIVEFK VDIPGSYTLV DHSIFRAFNK GALGQLKVEG AENPEIMTQK LSDTAYAGNG AAPAASAPAA SAPAASASEK SVY*
4/88          NENVQSTIVP AGGSAIVRFK VDIPGSYTLV DHSIFRAFNK GAIGQLKVRG AFNPEITTQK LSDTAYAGNG AAPAASAPAA SAPAASAPEK SVY*
AK50          NENVQSTIVP AGGSAIVEFK VDIPGSYTLV DHSIFRAFNK GALGQLKVEG AENPEIMTQK LSDTAYAGNG AAPAASAPAA SAPAASASFK SVY*
B283          NENVQSTIVP AGGSAIVEFK VDIPGSYTLV DHSIFRAFNK GALGQLKVE- --------- ---------- ---------- ---------- ----
EG327         NENVQSTIVP AGGSAIVEFK VDIPGSYTLV DHSIFRAFNK GALGQLKVE- --------- ---------- ---------- ---------- ----
FG329         NENVQSTIVP AGGSAIVEFK VDIPGSYTLV DHSIFRAFNK GALGQLKVE- --------- ---------- ---------- ---------- ----
NGPB24        NENVQSTIVP AGGSAIVEFK VDIPGSYTLV DHSIFRAFNK GALGQLKVE- --------- ---------- ---------- ---------- ----
NG144/82      NENVQSTIVP AGGSAIVEFK VDIPGSYTLV DHSIFRAFNK GALGQLKVE- --------- ---------- ---------- ---------- ----
BZ169         NENVQSTIVP AGGSAIVEFK VDIPGSYTLV DHSIFRAFNK GALGQLKVE- --------- ---------- ---------- ---------- ----
44/76         NENVQSTIVP AGGSAIVEFK VDIPGSYTLV DHSIFRAFNK GALGQLKVE- --------- ---------- ---------- ---------- ----
Z2491         NENVQSTIVP ACCSAIVEFK VDIPGSYTLV DHSIFRAFNK GALGQLKVEG AENPEIMTQK LSDTAYAGNG AAPAASAPAA SAPAASAPAK SDY*
107           NENVQSTIVP ACCSAIVEFK VDIPCSYTLV DHSIFRAFNK CALGQLKVE- --------- ---------- ---------- ---------- ----
3/88          NENVQSTIVP AGGSAIVEFK VDIPGSYTLV DHSIFRAFNK GALGQLKVE- --------- ---------- ---------- ---------- ----
BZ133         NENVQSTIVP AGGSAIVEFK VDIPGSYTLV DHSIFRAFNK GALGQLKVE- --------- ---------- ---------- ---------- ----
528           NFNVQSTIVP AGGSAIVRFK VNTPGSYTLV DHSIFRAFNK GALGQIKVE- --------- ---------- ---------- ---------- ----
Fam18         NENVQSTIVP AGGSAIVEFK VDIPGSYTLV DHSIFRAFNK GALGQLKVEG AENPEIMTQK LSDTAYAGNG AAPAASAPAA SAPAASASEK SVY*
1000          NENVQSTIVP AGGSAIVEFK VDIPGSYTLV DHSIFRAFNK GALGQLKVEG AENPEIMTQK LSDTAYAGNG AAPAASAPRA SAPAASESEK SVY*
NGP20         NENVQSTIVP ACCSAIVEFK VDLPGSYTLV DHSIFRAFNK GALGQLKVEC AENPEIMTQK LSDTAYACNC AAPAASAPAA SAPAASASEK SVY*
42B           NENVQSTIVP AGGSAIVEFK VDIPGSYTLV DHSIFRAFNK GALGQLKVEG AENPEIMTQK LSDTAYAGNG AAPAASAPAA SAPAASASEK SVY*
B6116/77      NENVQSTIVP AGGSAIVEFK VDIPGSYTLV DHSIFRANFK GALGQLKVE- --------- ---------- ---------- ---------- ----
2970          NENVQSTIVP AGGSAIVEFK VDIPGSYTLV DHSIFRAFNK GALGQLKVE- --------- ---------- ---------- ---------- ----
DK353         NENVQSTIVP AGGSAIVEFK VDIPGSYTLV DHSIFRAFNK GALGQLKVE- --------- ---------- ---------- ---------- ----
BZ210         NENVQSTIVP AGGSAIVEFK VDIPGSYTLV DHSIFRAFNK GALGQLKVE- --------- ---------- ---------- ---------- ----
BZ157         NENVQSTIVP AGGSATVEFK VDIPGSYTLV DHSTFRAFNK GAIGQLKVF- --------- ---------- ---------- ---------- ----
BZ163         NENVQSTIVP AGGSAIVEFK VDIPGSYTLV DHSIFRAFNK GALGQLKVE- --------- ---------- ---------- ---------- ----
MP-31B        NENVQSTIVP AGGSAIVEHK VDLPGSYTLV DHSIFRAFNK GALGQLKVE- --------- ---------- ---------- ---------- ----
MP-1B         NENVQSTIVP AGGSAIVEFK VDIPGSYTLV DHSIFRAFNK GALGQLKVE- --------- ---------- ---------- ---------- ----
MP-8B         NENVQSTIVP AGGSAIVEFK VDIPGSYTLV DHSIFRAFNK GALGQLKVE- --------- ---------- ---------- ---------- ----
AK22          NENVQSTIVP ACCSAIVEFK VDIPGSYTLV DHSIFRAFNK CALGQLKVE- --------- ---------- ---------- ---------- ----
H38           NENVQSTIVP AGGSAIVEFK VDIPGSYTLV DHSIFRAFNK GALGQLKVE- --------- ---------- ---------- ---------- ----
H15           NENVQSTIVP AGGSAIVEFK VDIPGSYTLV DHSIFRAFNK GALGQLKVE- --------- ---------- ---------- ---------- ----
H36           NENVQSTIVP AGGSATVRFK VDTPGSYTLV DHSTFRAFNK GAIGQIKVE- --------- ---------- ---------- ---------- ----
400           NFNVQSTIVP AGGSAIVEFK VDIPGSYTLV DHSIFRAFNK GALGQLKVE- --------- ---------- ---------- ---------- ----
BZ47          NENVQSTIVP AGGSAIVEFK VDLPGSYTLV DHSIFRAFNK GALGQLKVE- --------- ---------- ---------- ---------- ----
931905        NENVQSTIVP AGGSAIVEFK VDIPGSYTLV DHSIFRAFNK GALGQLKVE- --------- ---------- ---------- ---------- ----
88/03415      NENVQSTIVP AGGSAIVEFK VDIPGSYTLV DHSIFRAFNK GALGQLKVE- --------- ---------- ---------- ---------- ----
M40/94        NENVQSTIVP AGGSAIVEFK VDIPGSYTLV DHSIFRAFNK GALGQLKVE- --------- ---------- ---------- ---------- ----
351           NENVQSTIVP AGGSAIVEFK VDIPGSYTLV DHSIFRAFNK GALGQLKVE- --------- ---------- ---------- ---------- ----
BZ198         NENVQSTIVP AGGSAIVEFK VDIPGSYTLV DHSIFRAFNK GALGQLKVE- --------- ---------- ---------- ---------- ----
MP-3B         NENVQSTIVP AGGSAIVEFK VDIPGSYTLV DHSIFRAFNK GALGQLKVE- --------- ---------- ---------- ---------- ----
```

SEQ ID NO: 1

MKRQALAAMIASLFALAACGGEPAAQAPAETPAAAAEAASSAAQTAAETPSGELPVIDAVTT
HAPEVPPAIDRDYPAKVRVKMETVEKTMTMEDGVEYRYWTFDGDVPGRMIRVREGDTVEVEF
SNNPSSTVPHNVDFHAATGQGGGAAATFTAPGRTSTFSFKALQPGLYIYHCAVAPVGMHIAN
GMYGLILVEPKEGLPKVDKEFYIVQGDFYTKGKKGAQGLQPFDMDKAVAEQPEYVVFNGHVG
AIAGDNALKAKAGETVRMYVGNGGPNLVSSFHVIGEIFDKVYVEGGKLINENVQSTIVPAGG
SAIVEFKVDIPGSYTLVDHSIFRAFNKGALGQLKVEGAENPEIMDYKDDDDK

FIG. 8

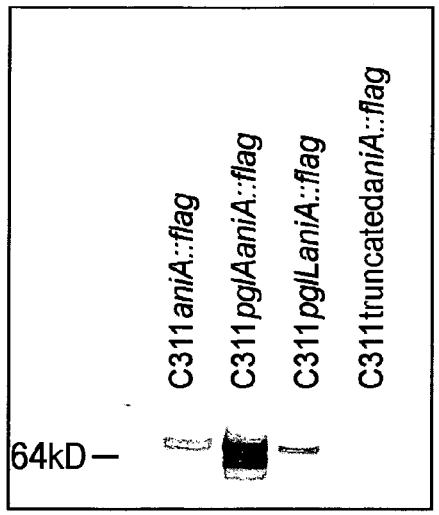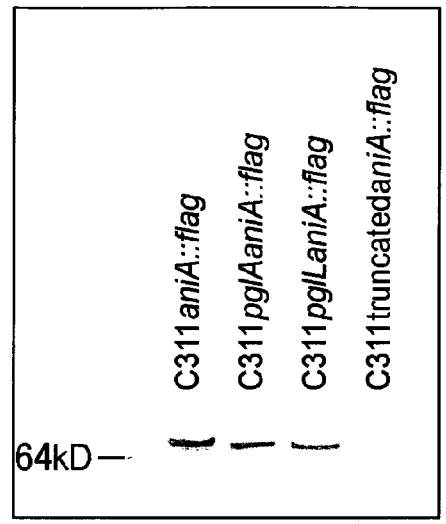
FIG. 10

SEQ ID NO: 2
Tc AniA#1
GSHMAAQATAETPAGELPVIDAVTTHAPEVPPAIDRDYPAKVRVKMETVEKTMKMDD
GVEYRYWTFDGDVPGRMIRVREGDTVEVEFSNNPSSTVPHNVDFHAATGQGGGAAAT
FTAPGRTSTFSFKALQPGLYIYHCAVAPVGMHIANGMYGLILVEPKEGLPKVDKEFY
IVQGDFYTKGKKGAQGLQPFDMDKAVAEQPEYVVFNGHVGAIAGDNALKAKAGETVR
MYVGNGGPNLVSSFHVIGEIFDKVYVEGGKLINENVQSTIVPAGGSAIVEFKVDIPG
NYTLVDHSIFRAFNKGALGQLKVE

SEQ ID NO: 3
Tc AniA #2
GSHMAAQATAETPAGELPVIDAVTTHAPEVPPAIDRDYPAKVRVKMETVEKTMKMDD
GVEYRYWTFDGDVPGRMIRVREGDTVEVEFSNNPSSTVPHNVDFHAATGQGGGAAAT
FTAPGRTSTFSFKALQPGLYIYHCAVAPVGMHIANGMYGLILVEPKEGLPKVDKEFY
IVQGDFYTKGKKGAQGLQPFDMDKAVAEQPEYVVFNGHVGAIAGDNALKAKAGETVR
MYVGNGGPNLVSSFHVIGEIFDKVYVEGGKLINENVQSTIVPAGGSAIVEFKVDIPG
NYTLVDHSIFRAFNKGALGQLKVEGAENPEIM

SEQ ID NO: 4
Tc AniA #3
GSHMAAQATAETPAGELPVIDAVTTHAPEVPPAIDRDYPAKVRVKMETVEKTMKMDD
GVEYRYWTFDGDVPGRMIRVREGDTVEVEFSNNPSSTVPHNVDFHAATGQGGGAAAT
FTAPGRTSTFSFKALQPGLYIYHCAVAPVGMHIANGMYGLILVEPKEGLPKVDKEFY
IVQGDFYTKGKKGAQGLQPFDMDKAVAEQPEYVVFNGHVGAIAGDNALKAKAGETVR
MYVGNGGPNLVSSFHVIGEIFDKVYVEGGKLINENVQSTIVPAGGSAIVEFKVDIPG
NYTLVDHSIFRAFNKGALGQLKVEGAENPEIMTQKLSDTAYAGSG

SEQ ID NO: 5
Tc AniA#4
GSHMAAQATAETPAGELPVIDAVTTHAPEVPPAIDRDYPAKVRVKMETVEKTMKMDD
GVEYRYWTFDGDVPGRMIRVREGDTVEVEFSNNPSSTVPHNVDFHAATGQGGGAAAT
FTAPGRTSTFSFKALQPGLYIYHCAVAPVGMHIANGMYGLILVEPKEGLPKVDKEFY
IVQGDFYTKGKKGAQGLQPFDMDKAVAEQPEYVVFNGHVGAIAGDNALKAKAGETVR
MYVGNGGPNLVSSFHVIGEIFDKVYVEGGKLINENVQSTIVPAGGSAIVEFKVDIPG
NYTLVDHSIFRAFNKGALGQLKVEGAENPEIMTQKLSDTAYAGSGAASAPAASAPAA
SAPAASASEKSVY

SEQ ID NO: 6
Tc AniA#5
GSHMELPVIDAVTTHAPEVPPAIDRDYPAKVRVKMETVEKTMKMDDGVEYRYWTFDG
DVPGRMIRVREGDTVEVEFSNNPSSTVPHNVDFHAATGQGGGAAATFTAPGRTSTFS
FKALQPGLYIYHCAVAPVGMHIANGMYGLILVEPKEGLPKVDKEFYIVQGDFYTKGK
KGAQGLQPFDMDKAVAEQPEYVVFNGHVGAIAGDNALKAKAGETVRMYVGNGGPNLV
SSFHVIGEIFDKVYVEGGKLINENVQSTIVPAGGSAIVEFKVDIPGNYTLVDHSIFR
AFNKGALGQLKVE

FIG. 13

SEQ ID NO: 7
Tc AniA #6
GSHMELPVIDAVTTHAPEVPPAIDRDYPAKVRVKMETVEKTMKMDDGVEYRYWTFDG
DVPGRMIRVREGDTVEVEFSNNPSSTVPHNVDFHAATGQGGGAAATFTAPGRTSTFS
FKALQPGLYIYHCAVAPVGMHIANGMYGLILVEPKEGLPKVDKEFYIVQGDFYTKGK
KGAQGLQPFDMDKAVAEQPEYVVFNGHVGAIAGDNALKAKAGETVRMYVGNGGPNLV
SSFHVIGEIFDKVYVEGGKLINENVQSTIVPAGGSAIVEFKVDIPGNYTLVDHSIFR
AFNKGALGQLKVEGAENPEIM

SEQ ID NO: 8
Tc AniA #7
GSHMELPVIDAVTTHAPEVPPAIDRDYPAKVRVKMETVEKTMKMDDGVEYRYWTFDG
DVPGRMIRVREGDTVEVEFSNNPSSTVPHNVDFHAATGQGGGAAATFTAPGRTSTFS
FKALQPGLYIYHCAVAPVGMHIANGMYGLILVEPKEGLPKVDKEFYIVQGDFYTKGK
KGAQGLQPFDMDKAVAEQPEYVVFNGHVGAIAGDNALKAKAGETVRMYVGNGGPNLV
SSFHVIGEIFDKVYVEGGKLINENVQSTIVPAGGSAIVEFKVDIPGNYTLVDHSIFR
AFNKGALGQLKVEGAENPEIMTQKLSDTAYAGSG

SEQ ID NO: 9
Tc AniA #8
GSHMELPVIDAVTTHAPEVPPAIDRDYPAKVRVKMETVEKTMKMDDGVEYRYWTFDG
DVPGRMIRVREGDTVEVEFSNNPSSTVPHNVDFHAATGQGGGAAATFTAPGRTSTFS
FKALQPGLYIYHCAVAPVGMHIANGMYGLILVEPKEGLPKVDKEFYIVQGDFYTKGK
KGAQGLQPFDMDKAVAEQPEYVVFNGHVGAIAGDNALKAKAGETVRMYVGNGGPNLV
SSFHVIGEIFDKVYVEGGKLINENVQSTIVPAGGSAIVEFKVDIPGNYTLVDHSIFR
AFNKGALGQLKVEGAENPEIMTQKLSDTAYAGSGAASAPAASAPAASAPAASASEKS
VY

FIG. 13, continued

SEQUENCE LISTING

<160> NUMBER OF SEQ ID NOS: 113

<210> SEQ ID NO 1
<211> LENGTH: 362
<212> TYPE: PRT
<213> ORGANISM: Artificial Sequence
<220> FEATURE:
<223> OTHER INFORMATION: Truncated FLAG-tagged AniA.

<400> SEQUENCE: 1

```
Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Glu Thr Pro
            20                  25                  30

Ala Ala Ala Ala Glu Ala Ala Ser Ser Ala Ala Gln Thr Ala Ala Glu
        35                  40                  45

Thr Pro Ser Gly Glu Leu Pro Val Ile Asp Ala Val Thr Thr His Ala
    50                  55                  60

Pro Glu Val Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
        115                 120                 125

Ser Ser Thr Val Pro His Asn Val Asp Phe His Ala Ala Thr Gly Gln
    130                 135                 140

Gly Gly Gly Ala Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190
```

```
Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Gly Ala Gln Gly
    210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Met Asp Tyr Lys Asp Asp Asp Lys
            355                 360

<210> SEQ ID NO 2
<211> LENGTH: 309
<212> TYPE: PRT
<213> ORGANISM: Neisseria gonorrhoea

<400> SEQUENCE: 2

Gly Ser His Met Ala Ala Gln Ala Thr Ala Thr Pro Ala Gly Glu
1               5                   10                  15

Leu Pro Val Ile Asp Ala Val Thr Thr His Ala Pro Glu Val Pro Pro
                20                  25                  30

Ala Ile Asp Arg Asp Tyr Pro Ala Lys Val Arg Val Lys Met Glu Thr
            35                  40                  45

Val Glu Lys Thr Met Lys Met Asp Asp Gly Val Glu Tyr Arg Tyr Trp
    50                  55                  60

Thr Phe Asp Gly Asp Val Pro Gly Arg Met Ile Arg Val Arg Glu Gly
65                  70                  75                  80

Asp Thr Val Glu Val Glu Phe Ser Asn Asn Pro Ser Ser Thr Val Pro
                85                  90                  95

His Asn Val Asp Phe His Ala Ala Thr Gly Gln Gly Gly Gly Ala Ala
                100                 105                 110

Ala Thr Phe Thr Ala Pro Gly Arg Thr Ser Thr Phe Ser Phe Lys Ala
            115                 120                 125

Leu Gln Pro Gly Leu Tyr Ile Tyr His Cys Ala Val Ala Pro Val Gly
        130                 135                 140

Met His Ile Ala Asn Gly Met Tyr Gly Leu Ile Leu Val Glu Pro Lys
145                 150                 155                 160

Glu Gly Leu Pro Lys Val Asp Lys Glu Phe Tyr Ile Val Gln Gly Asp
                165                 170                 175

Phe Tyr Thr Lys Gly Lys Lys Gly Ala Gln Gly Leu Gln Pro Phe Asp
            180                 185                 190

Met Asp Lys Ala Val Ala Glu Gln Pro Glu Tyr Val Val Phe Asn Gly
        195                 200                 205
```

His Val Gly Ala Ile Ala Gly Asp Asn Ala Leu Lys Ala Lys Ala Gly
    210                 215                 220

Glu Thr Val Arg Met Tyr Val Gly Asn Gly Gly Pro Asn Leu Val Ser
225                 230                 235                 240

Ser Phe His Val Ile Gly Glu Ile Phe Asp Lys Val Tyr Val Glu Gly
                245                 250                 255

Gly Lys Leu Ile Asn Glu Asn Val Gln Ser Thr Ile Val Pro Ala Gly
            260                 265                 270

Gly Ser Ala Ile Val Glu Phe Lys Val Asp Ile Pro Gly Asn Tyr Thr
        275                 280                 285

Leu Val Asp His Ser Ile Phe Arg Ala Phe Asn Lys Gly Ala Leu Gly
    290                 295                 300

Gln Leu Lys Val Glu
305

<210> SEQ ID NO 3
<211> LENGTH: 317
<212> TYPE: PRT
<213> ORGANISM: Neisseria gonorrhoea

<400> SEQUENCE: 3

Gly Ser His Met Ala Ala Gln Ala Thr Ala Glu Thr Pro Ala Gly Glu
1               5                   10                  15

Leu Pro Val Ile Asp Ala Val Thr Thr His Ala Pro Glu Val Pro Pro
                20                  25                  30

Ala Ile Asp Arg Asp Tyr Pro Ala Lys Val Arg Val Lys Met Glu Thr
            35                  40                  45

Val Glu Lys Thr Met Lys Met Asp Asp Gly Val Glu Tyr Arg Tyr Trp
        50                  55                  60

Thr Phe Asp Gly Asp Val Pro Gly Arg Met Ile Arg Val Arg Glu Gly
65                  70                  75                  80

Asp Thr Val Glu Val Glu Phe Ser Asn Asn Pro Ser Ser Thr Val Pro
                85                  90                  95

His Asn Val Asp Phe His Ala Thr Gly Gln Gly Gly Gly Ala Ala
            100                 105                 110

Ala Thr Phe Thr Ala Pro Gly Arg Thr Ser Thr Phe Ser Phe Lys Ala
        115                 120                 125

Leu Gln Pro Gly Leu Tyr Ile Tyr His Cys Ala Val Ala Pro Val Gly
    130                 135                 140

Met His Ile Ala Asn Gly Met Tyr Gly Leu Ile Leu Val Glu Pro Lys
145                 150                 155                 160

Glu Gly Leu Pro Lys Val Asp Lys Glu Phe Tyr Ile Val Gln Gly Asp
                165                 170                 175

Phe Tyr Thr Lys Gly Lys Lys Gly Ala Gln Gly Leu Gln Pro Phe Asp
            180                 185                 190

Met Asp Lys Ala Val Ala Glu Gln Pro Glu Tyr Val Val Phe Asn Gly
        195                 200                 205

His Val Gly Ala Ile Ala Gly Asp Asn Ala Leu Lys Ala Lys Ala Gly
    210                 215                 220

Glu Thr Val Arg Met Tyr Val Gly Asn Gly Gly Pro Asn Leu Val Ser
225                 230                 235                 240

Ser Phe His Val Ile Gly Glu Ile Phe Asp Lys Val Tyr Val Glu Gly
                245                 250                 255

Gly Lys Leu Ile Asn Glu Asn Val Gln Ser Thr Ile Val Pro Ala Gly

```
              260                 265                 270
Gly Ser Ala Ile Val Glu Phe Lys Val Asp Ile Pro Gly Asn Tyr Thr
            275                 280                 285

Leu Val Asp His Ser Ile Phe Arg Ala Phe Asn Lys Gly Ala Leu Gly
            290                 295                 300

Gln Leu Lys Val Glu Gly Ala Glu Asn Pro Glu Ile Met
305                 310                 315

<210> SEQ ID NO 4
<211> LENGTH: 330
<212> TYPE: PRT
<213> ORGANISM: Neisseria gonorrhoea

<400> SEQUENCE: 4

Gly Ser His Met Ala Ala Gln Ala Thr Ala Glu Thr Pro Ala Gly Glu
1               5                  10                  15

Leu Pro Val Ile Asp Ala Val Thr Thr His Ala Pro Glu Val Pro Pro
            20                  25                  30

Ala Ile Asp Arg Asp Tyr Pro Ala Lys Val Arg Val Lys Met Glu Thr
        35                  40                  45

Val Glu Lys Thr Met Lys Met Asp Asp Gly Val Glu Tyr Arg Tyr Trp
50                  55                  60

Thr Phe Asp Gly Asp Val Pro Gly Arg Met Ile Arg Val Arg Glu Gly
65                  70                  75                  80

Asp Thr Val Glu Val Glu Phe Ser Asn Asn Pro Ser Ser Thr Val Pro
                85                  90                  95

His Asn Val Asp Phe His Ala Ala Thr Gly Gln Gly Gly Gly Ala Ala
            100                 105                 110

Ala Thr Phe Thr Ala Pro Gly Arg Thr Ser Thr Phe Ser Phe Lys Ala
        115                 120                 125

Leu Gln Pro Gly Leu Tyr Ile Tyr His Cys Ala Val Ala Pro Val Gly
130                 135                 140

Met His Ile Ala Asn Gly Met Tyr Gly Leu Ile Leu Val Glu Pro Lys
145                 150                 155                 160

Glu Gly Leu Pro Lys Val Asp Lys Glu Phe Tyr Ile Val Gln Gly Asp
                165                 170                 175

Phe Tyr Thr Lys Gly Lys Lys Gly Ala Gln Gly Leu Gln Pro Phe Asp
            180                 185                 190

Met Asp Lys Ala Val Ala Glu Gln Pro Glu Tyr Val Val Phe Asn Gly
        195                 200                 205

His Val Gly Ala Ile Ala Gly Asp Asn Ala Leu Lys Ala Lys Ala Gly
            210                 215                 220

Glu Thr Val Arg Met Tyr Val Gly Asn Gly Gly Pro Asn Leu Val Ser
225                 230                 235                 240

Ser Phe His Val Ile Gly Glu Ile Phe Asp Lys Val Tyr Val Glu Gly
                245                 250                 255

Gly Lys Leu Ile Asn Glu Asn Val Gln Ser Thr Ile Val Pro Ala Gly
            260                 265                 270

Gly Ser Ala Ile Val Glu Phe Lys Val Asp Ile Pro Gly Asn Tyr Thr
        275                 280                 285

Leu Val Asp His Ser Ile Phe Arg Ala Phe Asn Lys Gly Ala Leu Gly
            290                 295                 300

Gln Leu Lys Val Glu Gly Ala Glu Asn Pro Glu Ile Met Thr Gln Lys
305                 310                 315                 320
```

```
Leu Ser Asp Thr Ala Tyr Ala Gly Ser Gly
            325                 330

<210> SEQ ID NO 5
<211> LENGTH: 355
<212> TYPE: PRT
<213> ORGANISM: Neisseria gonorrhoea

<400> SEQUENCE: 5

Gly Ser His Met Ala Ala Gln Ala Thr Ala Glu Thr Pro Ala Gly Glu
1               5                   10                  15

Leu Pro Val Ile Asp Ala Val Thr Thr His Ala Pro Glu Val Pro Pro
            20                  25                  30

Ala Ile Asp Arg Asp Tyr Pro Ala Lys Val Arg Val Lys Met Glu Thr
        35                  40                  45

Val Glu Lys Thr Met Lys Met Asp Asp Gly Val Glu Tyr Arg Tyr Trp
    50                  55                  60

Thr Phe Asp Gly Asp Val Pro Gly Arg Met Ile Arg Val Arg Glu Gly
65                  70                  75                  80

Asp Thr Val Glu Val Glu Phe Ser Asn Asn Pro Ser Ser Thr Val Pro
                85                  90                  95

His Asn Val Asp Phe His Ala Ala Thr Gly Gln Gly Gly Gly Ala Ala
            100                 105                 110

Ala Thr Phe Thr Ala Pro Gly Arg Thr Ser Thr Phe Ser Phe Lys Ala
        115                 120                 125

Leu Gln Pro Gly Leu Tyr Ile Tyr His Cys Ala Val Ala Pro Val Gly
    130                 135                 140

Met His Ile Ala Asn Gly Met Tyr Gly Leu Ile Leu Val Glu Pro Lys
145                 150                 155                 160

Glu Gly Leu Pro Lys Val Asp Lys Glu Phe Tyr Ile Val Gln Gly Asp
                165                 170                 175

Phe Tyr Thr Lys Gly Lys Lys Gly Ala Gln Gly Leu Gln Pro Phe Asp
            180                 185                 190

Met Asp Lys Ala Val Ala Glu Gln Pro Glu Tyr Val Val Phe Asn Gly
        195                 200                 205

His Val Gly Ala Ile Ala Gly Asp Asn Ala Leu Lys Ala Lys Ala Gly
    210                 215                 220

Glu Thr Val Arg Met Tyr Val Gly Asn Gly Gly Pro Asn Leu Val Ser
225                 230                 235                 240

Ser Phe His Val Ile Gly Glu Ile Phe Asp Lys Val Tyr Val Glu Gly
                245                 250                 255

Gly Lys Leu Ile Asn Glu Asn Val Gln Ser Thr Ile Val Pro Ala Gly
            260                 265                 270

Gly Ser Ala Ile Val Glu Phe Lys Val Asp Ile Pro Gly Asn Tyr Thr
        275                 280                 285

Leu Val Asp His Ser Ile Phe Arg Ala Phe Asn Lys Gly Ala Leu Gly
    290                 295                 300

Gln Leu Lys Val Glu Gly Ala Glu Asn Pro Glu Ile Met Thr Gln Lys
305                 310                 315                 320

Leu Ser Asp Thr Ala Tyr Ala Gly Ser Gly Ala Ala Ser Ala Pro Ala
                325                 330                 335

Ala Ser Ala Pro Ala Ala Ser Ala Pro Ala Ala Ser Ala Ser Glu Lys
            340                 345                 350

Ser Val Tyr
        355
```

<210> SEQ ID NO 6
<211> LENGTH: 298
<212> TYPE: PRT
<213> ORGANISM: Neisseria gonorrhoea

<400> SEQUENCE: 6

```
Gly Ser His Met Glu Leu Pro Val Ile Asp Ala Val Thr Thr His Ala
1               5                   10                  15

Pro Glu Val Pro Pro Ala Ile Asp Arg Asp Tyr Pro Ala Lys Val Arg
            20                  25                  30

Val Lys Met Glu Thr Val Glu Lys Thr Met Lys Met Asp Asp Gly Val
        35                  40                  45

Glu Tyr Arg Tyr Trp Thr Phe Asp Gly Asp Val Pro Gly Arg Met Ile
    50                  55                  60

Arg Val Arg Glu Gly Asp Thr Val Glu Val Glu Phe Ser Asn Asn Pro
65                  70                  75                  80

Ser Ser Thr Val Pro His Asn Val Asp Phe His Ala Ala Thr Gly Gln
                85                  90                  95

Gly Gly Gly Ala Ala Ala Thr Phe Thr Ala Pro Gly Arg Thr Ser Thr
            100                 105                 110

Phe Ser Phe Lys Ala Leu Gln Pro Gly Leu Tyr Ile Tyr His Cys Ala
        115                 120                 125

Val Ala Pro Val Gly Met His Ile Ala Asn Gly Met Tyr Gly Leu Ile
    130                 135                 140

Leu Val Glu Pro Lys Glu Gly Leu Pro Lys Val Asp Lys Glu Phe Tyr
145                 150                 155                 160

Ile Val Gln Gly Asp Phe Tyr Thr Lys Gly Lys Lys Gly Ala Gln Gly
                165                 170                 175

Leu Gln Pro Phe Asp Met Asp Lys Ala Val Ala Glu Gln Pro Glu Tyr
            180                 185                 190

Val Val Phe Asn Gly His Val Gly Ala Ile Ala Gly Asp Asn Ala Leu
        195                 200                 205

Lys Ala Lys Ala Gly Glu Thr Val Arg Met Tyr Val Gly Asn Gly Gly
    210                 215                 220

Pro Asn Leu Val Ser Ser Phe His Val Ile Gly Glu Ile Phe Asp Lys
225                 230                 235                 240

Val Tyr Val Glu Gly Gly Lys Leu Ile Asn Glu Asn Val Gln Ser Thr
                245                 250                 255

Ile Val Pro Ala Gly Gly Ser Ala Ile Val Glu Phe Lys Val Asp Ile
            260                 265                 270

Pro Gly Asn Tyr Thr Leu Val Asp His Ser Ile Phe Arg Ala Phe Asn
        275                 280                 285

Lys Gly Ala Leu Gly Gln Leu Lys Val Glu
    290                 295
```

<210> SEQ ID NO 7
<211> LENGTH: 306
<212> TYPE: PRT
<213> ORGANISM: Neisseria gonorrhoea

<400> SEQUENCE: 7

```
Gly Ser His Met Glu Leu Pro Val Ile Asp Ala Val Thr Thr His Ala
1               5                   10                  15

Pro Glu Val Pro Pro Ala Ile Asp Arg Asp Tyr Pro Ala Lys Val Arg
            20                  25                  30
```

```
Val Lys Met Glu Thr Val Glu Lys Thr Met Lys Met Asp Asp Gly Val
            35                  40                  45

Glu Tyr Arg Tyr Trp Thr Phe Asp Gly Asp Val Pro Gly Arg Met Ile
 50                  55                  60

Arg Val Arg Glu Gly Asp Thr Val Glu Val Glu Phe Ser Asn Asn Pro
 65                  70                  75                  80

Ser Ser Thr Val Pro His Asn Val Asp Phe His Ala Ala Thr Gly Gln
                85                  90                  95

Gly Gly Gly Ala Ala Thr Phe Thr Ala Pro Gly Arg Thr Ser Thr
            100                 105                 110

Phe Ser Phe Lys Ala Leu Gln Pro Gly Leu Tyr Ile Tyr His Cys Ala
            115                 120                 125

Val Ala Pro Val Gly Met His Ile Ala Asn Gly Met Tyr Gly Leu Ile
            130                 135                 140

Leu Val Glu Pro Lys Glu Gly Leu Pro Lys Val Asp Lys Glu Phe Tyr
145                 150                 155                 160

Ile Val Gln Gly Asp Phe Tyr Thr Lys Gly Lys Gly Ala Gln Gly
                165                 170                 175

Leu Gln Pro Phe Asp Met Asp Lys Ala Val Ala Glu Gln Pro Glu Tyr
            180                 185                 190

Val Val Phe Asn Gly His Val Gly Ala Ile Ala Gly Asp Asn Ala Leu
            195                 200                 205

Lys Ala Lys Ala Gly Glu Thr Val Arg Met Tyr Val Gly Asn Gly Gly
210                 215                 220

Pro Asn Leu Val Ser Ser Phe His Val Ile Gly Glu Ile Phe Asp Lys
225                 230                 235                 240

Val Tyr Val Glu Gly Gly Lys Leu Ile Asn Glu Asn Val Gln Ser Thr
                245                 250                 255

Ile Val Pro Ala Gly Gly Ser Ala Ile Val Glu Phe Lys Val Asp Ile
                260                 265                 270

Pro Gly Asn Tyr Thr Leu Val Asp His Ser Ile Phe Arg Ala Phe Asn
            275                 280                 285

Lys Gly Ala Leu Gly Gln Leu Lys Val Glu Gly Ala Glu Asn Pro Glu
290                 295                 300

Ile Met
305

<210> SEQ ID NO 8
<211> LENGTH: 319
<212> TYPE: PRT
<213> ORGANISM: Neisseria gonorrhoea

<400> SEQUENCE: 8

Gly Ser His Met Glu Leu Pro Val Ile Asp Ala Val Thr Thr His Ala
 1               5                  10                  15

Pro Glu Val Pro Pro Ala Ile Asp Arg Asp Tyr Pro Ala Lys Val Arg
                20                  25                  30

Val Lys Met Glu Thr Val Glu Lys Thr Met Lys Met Asp Asp Gly Val
            35                  40                  45

Glu Tyr Arg Tyr Trp Thr Phe Asp Gly Asp Val Pro Gly Arg Met Ile
 50                  55                  60

Arg Val Arg Glu Gly Asp Thr Val Glu Val Glu Phe Ser Asn Asn Pro
 65                  70                  75                  80

Ser Ser Thr Val Pro His Asn Val Asp Phe His Ala Ala Thr Gly Gln
```

```
                85                  90                  95
Gly Gly Gly Ala Ala Ala Thr Phe Thr Ala Pro Gly Arg Thr Ser Thr
            100                 105                 110

Phe Ser Phe Lys Ala Leu Gln Pro Gly Leu Tyr Ile Tyr His Cys Ala
            115                 120                 125

Val Ala Pro Val Gly Met His Ile Ala Asn Gly Met Tyr Gly Leu Ile
            130                 135                 140

Leu Val Glu Pro Lys Glu Gly Leu Pro Lys Val Asp Lys Glu Phe Tyr
145                 150                 155                 160

Ile Val Gln Gly Asp Phe Tyr Thr Lys Gly Lys Gly Ala Gln Gly
                165                 170                 175

Leu Gln Pro Phe Asp Met Asp Lys Ala Val Ala Glu Gln Pro Glu Tyr
            180                 185                 190

Val Val Phe Asn Gly His Val Gly Ala Ile Ala Gly Asp Asn Ala Leu
                195                 200                 205

Lys Ala Lys Ala Gly Glu Thr Val Arg Met Tyr Val Gly Asn Gly Gly
            210                 215                 220

Pro Asn Leu Val Ser Ser Phe His Val Ile Gly Glu Ile Phe Asp Lys
225                 230                 235                 240

Val Tyr Val Glu Gly Gly Lys Leu Ile Asn Glu Asn Val Gln Ser Thr
                245                 250                 255

Ile Val Pro Ala Gly Gly Ser Ala Ile Val Glu Phe Lys Val Asp Ile
            260                 265                 270

Pro Gly Asn Tyr Thr Leu Val Asp His Ser Ile Phe Arg Ala Phe Asn
            275                 280                 285

Lys Gly Ala Leu Gly Gln Leu Lys Val Glu Gly Ala Glu Asn Pro Glu
            290                 295                 300

Ile Met Thr Gln Lys Leu Ser Asp Thr Ala Tyr Ala Gly Ser Gly
305                 310                 315

<210> SEQ ID NO 9
<211> LENGTH: 344
<212> TYPE: PRT
<213> ORGANISM: Neisseria gonorrhoea

<400> SEQUENCE: 9

Gly Ser His Met Glu Leu Pro Val Ile Asp Ala Val Thr Thr His Ala
1               5                   10                  15

Pro Glu Val Pro Pro Ala Ile Asp Arg Asp Tyr Pro Ala Lys Val Arg
            20                  25                  30

Val Lys Met Glu Thr Val Glu Lys Thr Met Lys Met Asp Asp Gly Val
            35                  40                  45

Glu Tyr Arg Tyr Trp Thr Phe Asp Gly Asp Val Pro Gly Arg Met Ile
        50                  55                  60

Arg Val Arg Glu Gly Asp Thr Val Glu Val Glu Phe Ser Asn Asn Pro
65                  70                  75                  80

Ser Ser Thr Val Pro His Asn Val Asp Phe His Ala Ala Thr Gly Gln
                85                  90                  95

Gly Gly Gly Ala Ala Ala Thr Phe Thr Ala Pro Gly Arg Thr Ser Thr
            100                 105                 110

Phe Ser Phe Lys Ala Leu Gln Pro Gly Leu Tyr Ile Tyr His Cys Ala
            115                 120                 125

Val Ala Pro Val Gly Met His Ile Ala Asn Gly Met Tyr Gly Leu Ile
            130                 135                 140
```

```
Leu Val Glu Pro Lys Glu Gly Leu Pro Lys Val Asp Lys Glu Phe Tyr
145                 150                 155                 160

Ile Val Gln Gly Asp Phe Tyr Thr Lys Gly Lys Gly Ala Gln Gly
                165                 170                 175

Leu Gln Pro Phe Asp Met Asp Lys Ala Val Ala Glu Gln Pro Glu Tyr
            180                 185                 190

Val Val Phe Asn Gly His Val Gly Ala Ile Ala Gly Asp Asn Ala Leu
                195                 200                 205

Lys Ala Lys Ala Gly Glu Thr Val Arg Met Tyr Val Gly Asn Gly Gly
    210                 215                 220

Pro Asn Leu Val Ser Ser Phe His Val Ile Gly Glu Ile Phe Asp Lys
225                 230                 235                 240

Val Tyr Val Glu Gly Gly Lys Leu Ile Asn Glu Asn Val Gln Ser Thr
                245                 250                 255

Ile Val Pro Ala Gly Gly Ser Ala Ile Val Glu Phe Lys Val Asp Ile
                260                 265                 270

Pro Gly Asn Tyr Thr Leu Val Asp His Ser Ile Phe Arg Ala Phe Asn
            275                 280                 285

Lys Gly Ala Leu Gly Gln Leu Lys Val Glu Gly Ala Glu Asn Pro Glu
    290                 295                 300

Ile Met Thr Gln Lys Leu Ser Asp Thr Ala Tyr Ala Gly Ser Gly Ala
305                 310                 315                 320

Ala Ser Ala Pro Ala Ser Ala Pro Ala Ser Ala Pro Ala Ala
                325                 330                 335

Ser Ala Ser Glu Lys Ser Val Tyr
            340

<210> SEQ ID NO 10
<211> LENGTH: 19
<212> TYPE: DNA
<213> ORGANISM: Artificial Sequence
<220> FEATURE:
<223> OTHER INFORMATION: Primer sequence.

<400> SEQUENCE: 10
atgaaacgcc aagccttag                                             19

<210> SEQ ID NO 11
<211> LENGTH: 25
<212> TYPE: DNA
<213> ORGANISM: Artificial Sequence
<220> FEATURE:
<223> OTHER INFORMATION: Primer sequence.

<400> SEQUENCE: 11
ttatcggctt gtgcaacgga agccc                                      25

<210> SEQ ID NO 12
<211> LENGTH: 80
<212> TYPE: DNA
<213> ORGANISM: Artificial Sequence
<220> FEATURE:
<223> OTHER INFORMATION: Primer sequence.

<400> SEQUENCE: 12
aataaccgga catacttcat ctcgagtcac ttgtcgtcat cgtccttgta gtcataaacg    60
cttttttcgg atgcagaggc                                                80

<210> SEQ ID NO 13
```

```
<211> LENGTH: 31
<212> TYPE: DNA
<213> ORGANISM: Artificial Sequence
<220> FEATURE:
<223> OTHER INFORMATION: Primer sequence.

<400> SEQUENCE: 13
ctcgagatga agtatgtccg gttatttttc c                            31

<210> SEQ ID NO 14
<211> LENGTH: 65
<212> TYPE: DNA
<213> ORGANISM: Artificial Sequence
<220> FEATURE:
<223> OTHER INFORMATION: Primer sequence.

<400> SEQUENCE: 14
ttcatctcga gtcacttgtc gtcatcgtcc ttgtagtcat aaaccatgat ttcagggttt    60
tctgc                                                            65

<210> SEQ ID NO 15
<211> LENGTH: 32
<212> TYPE: DNA
<213> ORGANISM: Artificial Sequence
<220> FEATURE:
<223> OTHER INFORMATION: Primer sequence.

<400> SEQUENCE: 15
cgcactcata tgccgcacaa gctaccgccg aa                           32

<210> SEQ ID NO 16
<211> LENGTH: 29
<212> TYPE: DNA
<213> ORGANISM: Artificial Sequence
<220> FEATURE:
<223> OTHER INFORMATION: Primer sequence.

<400> SEQUENCE: 16
cgcactcata tgaactgccc gtcatcgat                               29

<210> SEQ ID NO 17
<211> LENGTH: 33
<212> TYPE: DNA
<213> ORGANISM: Artificial Sequence
<220> FEATURE:
<223> OTHER INFORMATION: Primer sequence.

<400> SEQUENCE: 17
gcgtccggat ccttactcta ctttcaattg ccc                          33

<210> SEQ ID NO 18
<211> LENGTH: 33
<212> TYPE: DNA
<213> ORGANISM: Artificial Sequence
<220> FEATURE:
<223> OTHER INFORMATION: Primer sequence.

<400> SEQUENCE: 18
gcgtccggat ccttacatga tttcagggtt ttc                          33

<210> SEQ ID NO 19
<211> LENGTH: 33
<212> TYPE: DNA
<213> ORGANISM: Artificial Sequence
<220> FEATURE:
<223> OTHER INFORMATION: Primer sequence.
```

```
<400> SEQUENCE: 19
gcgtccggat ccttagccgc tgccggcgta agc                                33

<210> SEQ ID NO 20
<211> LENGTH: 33
<212> TYPE: DNA
<213> ORGANISM: Artificial Sequence
<220> FEATURE:
<223> OTHER INFORMATION: Primer sequence.

<400> SEQUENCE: 20
gcgtccggat ccttattaat aaacgctttt ttc                                33

<210> SEQ ID NO 21
<211> LENGTH: 33
<212> TYPE: DNA
<213> ORGANISM: Neisseria meningitidis

<400> SEQUENCE: 21
atggaaaccg tcgaaaaaac catgaccatg gaa                                33

<210> SEQ ID NO 22
<211> LENGTH: 33
<212> TYPE: DNA
<213> ORGANISM: Neisseria meningitidis

<400> SEQUENCE: 22
atggaaaccg tcgaaaaaac catgaccatg gaa                                33

<210> SEQ ID NO 23
<211> LENGTH: 33
<212> TYPE: DNA
<213> ORGANISM: Neisseria meningitidis

<400> SEQUENCE: 23
atggaaaccg tcgaaaaaac catgaccatg gaa                                33

<210> SEQ ID NO 24
<211> LENGTH: 33
<212> TYPE: DNA
<213> ORGANISM: Neisseria meningitidis

<400> SEQUENCE: 24
atggaaaccg tcgaaaaaac catgaccatg gaa                                33

<210> SEQ ID NO 25
<211> LENGTH: 33
<212> TYPE: DNA
<213> ORGANISM: Neisseria meningitidis

<400> SEQUENCE: 25
atggaaaccg tcgaaaaaac catgaaaatg gac                                33

<210> SEQ ID NO 26
<211> LENGTH: 33
<212> TYPE: DNA
<213> ORGANISM: Neisseria gonorrhoea

<400> SEQUENCE: 26
atggaaaccg tcgaaaaaac catgaaaatg gac                                33

<210> SEQ ID NO 27
```

```
<211> LENGTH: 33
<212> TYPE: DNA
<213> ORGANISM: Neisseria gonorrhoea

<400> SEQUENCE: 27
atggaaaccg tcgaaaaaac catgaaaatg gac                           33

<210> SEQ ID NO 28
<211> LENGTH: 32
<212> TYPE: DNA
<213> ORGANISM: Neisseria meningitidis

<400> SEQUENCE: 28
atggaaaccg tcgaaaaacc atgaccatgg aa                            32

<210> SEQ ID NO 29
<211> LENGTH: 32
<212> TYPE: DNA
<213> ORGANISM: Neisseria meningitidis

<400> SEQUENCE: 29
atggaaaccg tcgaaaaacc atgaccatgg aa                            32

<210> SEQ ID NO 30
<211> LENGTH: 32
<212> TYPE: DNA
<213> ORGANISM: Neisseria meningitidis

<400> SEQUENCE: 30
atggaaaccg tcgaaaaacc atgaccatgg aa                            32

<210> SEQ ID NO 31
<211> LENGTH: 390
<212> TYPE: PRT
<213> ORGANISM: Neisseria meningitidis

<400> SEQUENCE: 31
```

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Glu Thr Pro
            20                  25                  30

Ala Ala Ala Ala Glu Ala Ala Ser Ser Ala Ala Gln Thr Ala Ala Glu
        35                  40                  45

Thr Pro Ser Gly Glu Leu Pro Val Ile Asp Ala Val Thr Thr His Ala
    50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
        115                 120                 125

Ser Ser Thr Val Pro His Asn Val Asp Phe His Ala Ala Thr Gly Gln
    130                 135                 140

Gly Gly Gly Ala Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

```
Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Lys Gly Ala Gln Gly
    210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Met Thr Gln Lys Leu Ser Asp Thr Ala Tyr Ala Gly Asn Gly Ala
        355                 360                 365

Ala Pro Ala Ala Ser Ala Pro Ala Ala Ser Ala Pro Ala Ala Ser Ala
    370                 375                 380

Ser Glu Lys Ser Val Tyr
385                 390

<210> SEQ ID NO 32
<211> LENGTH: 390
<212> TYPE: PRT
<213> ORGANISM: Neisseria meningitidis

<400> SEQUENCE: 32

Met Lys Arg Gln Ala Leu Ala Ala Met Ile Ala Ser Leu Phe Ala Leu
1               5                   10                  15

Ala Ala Cys Gly Gly Glu Pro Ala Gln Ala Pro Ala Glu Thr Pro
            20                  25                  30

Ala Ala Ala Ala Glu Ala Ala Ser Ser Ala Ala Gln Thr Ala Ala Glu
            35                  40                  45

Thr Pro Ser Gly Glu Leu Pro Val Ile Asp Ala Val Thr Thr His Ala
50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
            85                  90                  95

Glu Tyr Arg Tyr Trp Thr Phe Asp Gly Asp Val Pro Gly Arg Met Ile
        100                 105                 110

Arg Val Arg Glu Gly Asp Thr Val Glu Val Glu Phe Ser Asn Asn Pro
    115                 120                 125

Ser Ser Thr Val Pro His Asn Val Asp Phe His Ala Ala Thr Gly Gln
130                 135                 140

Gly Gly Gly Ala Ala Ala Thr Phe Thr Ala Pro Gly Arg Thr Ser Thr
145                 150                 155                 160
```

```
Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Gly Ala Gln Gly
    210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Met Thr Gln Lys Leu Ser Asp Thr Ala Tyr Ala Gly Asn Gly Ala
        355                 360                 365

Ala Pro Ala Ala Ser Ala Pro Ala Ala Ser Ala Pro Ala Ala Ser Ala
    370                 375                 380

Ser Glu Lys Ser Val Tyr
385                 390

<210> SEQ ID NO 33
<211> LENGTH: 390
<212> TYPE: PRT
<213> ORGANISM: Neisseria meningitidis

<400> SEQUENCE: 33

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Glu Thr Pro
            20                  25                  30

Ala Ala Ala Ala Glu Ala Ala Ser Ser Ala Ala Gln Thr Ala Ala Glu
        35                  40                  45

Thr Pro Ser Gly Glu Leu Pro Val Ile Asp Ala Val Thr Thr His Ala
50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
        115                 120                 125

Ser Ser Thr Val Pro His Asn Val Asp Phe His Ala Ala Thr Gly Gln
```

```
            130                 135                 140
Gly Gly Gly Ala Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Gly Ala Gln Gly
    210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Ile Thr Gln Lys Leu Ser Asp Thr Ala Tyr Ala Gly Asn Gly Ala
        355                 360                 365

Ala Pro Ala Ala Ser Ala Pro Ala Ala Ser Ala Pro Ala Ala Ser Ala
    370                 375                 380

Ser Glu Lys Ser Val Tyr
385                 390

<210> SEQ ID NO 34
<211> LENGTH: 390
<212> TYPE: PRT
<213> ORGANISM: Neisseria meningitidis

<400> SEQUENCE: 34

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Glu Thr Pro
            20                  25                  30

Ala Ala Ala Ala Glu Ala Ala Ser Ser Ala Ala Gln Thr Ala Ala Glu
        35                  40                  45

Thr Pro Ser Gly Glu Leu Pro Val Ile Asp Ala Val Thr Thr His Ala
    50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110
```

Arg Val Arg Glu Gly Asp Thr Val Glu Val Glu Phe Ser Asn Asn Pro
115                 120                 125

Ser Ser Thr Val Pro His Asn Val Asp Phe His Ala Ala Thr Gly Gln
130                 135                 140

Gly Gly Gly Ala Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
                180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Gly Ala Gln Gly
        210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
                260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
        290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
                340                 345                 350

Ile Met Thr Gln Lys Leu Ser Asp Thr Ala Tyr Ala Gly Asn Gly Ala
                355                 360                 365

Ala Pro Ala Ala Ser Ala Pro Ala Ala Ser Ala Pro Ala Ala Ser Ala
370                 375                 380

Ser Glu Lys Ser Val Tyr
385                 390

<210> SEQ ID NO 35
<211> LENGTH: 336
<212> TYPE: PRT
<213> ORGANISM: Neisseria meningitidis

<400> SEQUENCE: 35

Ala Ser Leu Phe Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
                20                  25                  30

Ala Gln Thr Ala Ala Glu Thr Pro Ser Gly Glu Leu Pro Val Ile Asp
            35                  40                  45

Ala Val Thr Thr His Ala Pro Glu Val Pro Ala Ile Asp Arg Asp
        50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

```
Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
            115                 120                 125

His Ala Ala Thr Gly Gln Gly Gly Ala Ala Ala Thr Phe Thr Ala
            130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
            165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
            195                 200                 205

Lys Lys Gly Ala Gln Gly Leu Gln Pro Phe Asp Met Asp Lys Ala Val
210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
            245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Gly Lys Leu Ile Asn
            275                 280                 285

Glu Asn Val Gln Ser Thr Ile Val Pro Ala Gly Gly Ser Ala Ile Val
            290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
            325                 330                 335

<210> SEQ ID NO 36
<211> LENGTH: 336
<212> TYPE: PRT
<213> ORGANISM: Neisseria meningitidis

<400> SEQUENCE: 36

Ala Ser Leu Phe Ala Leu Ala Ala Cys Gly Gly Glu Pro Ala Ala Gln
1               5                   10                  15

Ala Pro Ala Glu Thr Pro Ala Ala Ser Ala Glu Ala Ala Ser Ser Ala
            20                  25                  30

Ala Gln Thr Ala Ala Glu Thr Pro Ser Gly Glu Leu Pro Val Ile Asp
            35                  40                  45

Ala Val Thr Thr His Ala Pro Glu Val Pro Pro Ala Ile Asp Arg Asp
50                  55                  60

Tyr Pro Ala Lys Val Arg Val Lys Met Glu Thr Val Glu Lys Thr Met
65                  70                  75                  80

Lys Met Asp Asp Gly Val Glu Tyr His Tyr Trp Thr Phe Asp Gly Asp
            85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
            115                 120                 125

His Ala Ala Thr Gly Gln Gly Gly Gly Ala Ala Ala Thr Phe Thr Ala
```

-continued

```
                130                 135                 140
Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
                180                 185                 190

Val Asp Lys Glu Phe Tyr Ile Val Gln Gly Asp Phe Tyr Thr Lys Gly
                195                 200                 205

Lys Lys Gly Ala Gln Gly Leu Gln Pro Phe Asp Met Asp Lys Ala Ile
                210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
                260                 265                 270

Gly Glu Ile Phe Asp Lys Val Tyr Val Glu Gly Gly Lys Leu Ile Asn
                275                 280                 285

Glu Asn Val Gln Ser Thr Ile Val Pro Ala Gly Gly Ser Ala Ile Val
                290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 37
<211> LENGTH: 336
<212> TYPE: PRT
<213> ORGANISM: Neisseria meningitidis

<400> SEQUENCE: 37

Ala Ser Leu Phe Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
                20                  25                  30

Ala Gln Thr Ala Ala Glu Thr Pro Ser Gly Glu Leu Pro Val Ile Asp
                35                  40                  45

Ala Val Thr Thr His Ala Pro Glu Val Pro Ala Ile Asp Arg Asp
                50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
                100                 105                 110

Glu Phe Ser Asn Asn Pro Ser Ser Thr Val Pro His Asn Val Asp Phe
                115                 120                 125

His Ala Ala Thr Gly Gln Gly Gly Gly Ala Ala Thr Phe Thr Ala
                130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175
```

```
Gly Met Tyr Gly Leu Ile Leu Val Glu Pro Lys Glu Gly Leu Pro Lys
              180                 185                 190

Val Asp Lys Glu Phe Tyr Ile Val Gln Gly Asp Phe Tyr Thr Lys Gly
          195                 200                 205

Lys Lys Gly Ala Gln Gly Leu Gln Pro Phe Asp Met Asp Lys Ala Val
          210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
              245                 250                 255

Tyr Val Gly Asn Gly Pro Asn Leu Val Ser Ser Phe His Val Ile
              260                 265                 270

Gly Glu Ile Phe Asp Lys Val Tyr Val Glu Gly Gly Lys Leu Ile Asn
          275                 280                 285

Glu Asn Val Gln Ser Thr Ile Val Pro Ala Gly Gly Ser Ala Ile Val
          290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
              325                 330                 335

<210> SEQ ID NO 38
<211> LENGTH: 336
<212> TYPE: PRT
<213> ORGANISM: Neisseria meningitidis

<400> SEQUENCE: 38

Ala Ser Leu Phe Ala Leu Ala Ala Cys Gly Gly Glu Pro Ala Gln
1               5                   10                  15

Ala Pro Ala Glu Thr Pro Ala Ala Ala Glu Ala Ala Ser Ser Ala
              20                  25                  30

Ala Gln Thr Ala Ala Glu Thr Pro Ser Gly Glu Leu Pro Val Ile Asp
          35                  40                  45

Ala Val Thr Thr His Ala Pro Glu Val Pro Ala Ile Asp Arg Asp
50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
              85                  90                  95

Val Pro Gly Arg Met Ile Arg Val Arg Glu Gly Asp Thr Val Glu Val
          100                 105                 110

Glu Phe Ser Asn Asn Pro Ser Ser Thr Val Pro His Asn Val Asp Phe
          115                 120                 125

His Ala Ala Thr Gly Gln Gly Gly Gly Ala Ala Thr Phe Thr Ala
              130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
              165                 170                 175

Gly Met Tyr Gly Leu Ile Leu Val Glu Pro Lys Glu Gly Leu Pro Lys
              180                 185                 190

Val Asp Lys Glu Phe Tyr Ile Val Gln Gly Asp Phe Tyr Thr Lys Gly
          195                 200                 205

Lys Lys Gly Ala Gln Gly Leu Gln Pro Phe Asp Met Asp Lys Ala Val
          210                 215                 220
```

```
Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
            245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Gly Lys Leu Ile Asn
            275                 280                 285

Glu Asn Val Gln Ser Thr Ile Val Pro Ala Gly Ser Ala Ile Val
290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335
```

<210> SEQ ID NO 39
<211> LENGTH: 336
<212> TYPE: PRT
<213> ORGANISM: Neisseria meningitidis

<400> SEQUENCE: 39

```
Ala Ser Leu Leu Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
            20                  25                  30

Ala Gln Thr Ala Ala Glu Thr Pro Ser Gly Glu Leu Pro Val Ile Asp
        35                  40                  45

Ala Val Thr Thr His Ala Pro Glu Val Pro Ala Ile Asp Arg Asp
50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
        115                 120                 125

His Ala Ala Thr Gly Gln Gly Gly Ala Ala Thr Phe Thr Ala
130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
        195                 200                 205

Lys Lys Gly Ala Gln Gly Leu Gln Pro Phe Asp Met Asp Lys Ala Val
210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
            245                 250                 255

Tyr Val Gly Asn Gly Gly Pro Asn Leu Val Ser Ser Phe His Val Ile
```

```
                260                 265                 270
Gly Glu Ile Phe Asp Lys Val Tyr Val Glu Gly Gly Lys Leu Ile Asn
            275                 280                 285
Glu Asn Val Gln Ser Thr Ile Val Pro Ala Gly Gly Ser Ala Ile Val
        290                 295                 300
Glu Phe Lys Val Asp Ile Pro Gly Ser Tyr Thr Leu Val Asp His Ser
305                 310                 315                 320
Ile Phe Arg Ala Phe Asn Lys Gly Ala Leu Gly Gln Leu Lys Val Glu
                325                 330                 335

<210> SEQ ID NO 40
<211> LENGTH: 336
<212> TYPE: PRT
<213> ORGANISM: Neisseria meningitidis

<400> SEQUENCE: 40

Ala Ser Leu Leu Ala Leu Ala Ala Cys Gly Gly Glu Pro Ala Ala Gln
1               5                   10                  15
Ala Pro Ala Glu Thr Pro Ala Ala Ala Glu Ala Ala Ser Ser Ala
            20                  25                  30
Ala Gln Thr Ala Ala Glu Thr Pro Ser Gly Glu Leu Pro Val Ile Asp
        35                  40                  45
Ala Val Thr Thr His Ala Pro Glu Val Pro Ala Ile Asp Arg Asp
50                  55                  60
Tyr Pro Ala Lys Val Arg Val Lys Met Glu Thr Val Glu Lys Thr Met
65                  70                  75                  80
Thr Met Glu Asp Gly Val Glu Tyr Arg Tyr Trp Thr Phe Asp Gly Asp
                85                  90                  95
Val Pro Gly Arg Met Ile Arg Val Arg Glu Gly Asp Thr Val Glu Val
            100                 105                 110
Glu Phe Ser Asn Asn Pro Ser Ser Thr Val Pro His Asn Val Asp Phe
        115                 120                 125
His Ala Ala Thr Gly Gln Gly Gly Ala Ala Thr Phe Thr Ala
130                 135                 140
Pro Gly Arg Thr Ser Thr Phe Ser Phe Lys Ala Leu Gln Pro Gly Leu
145                 150                 155                 160
Tyr Ile Tyr His Cys Ala Val Ala Pro Val Gly Met His Ile Ala Asn
                165                 170                 175
Gly Met Tyr Gly Leu Ile Leu Val Glu Pro Lys Glu Gly Leu Pro Lys
            180                 185                 190
Val Asp Lys Glu Phe Tyr Ile Val Gln Gly Asp Phe Tyr Thr Lys Gly
        195                 200                 205
Lys Lys Gly Ala Gln Gly Leu Gln Pro Phe Asp Met Asp Lys Ala Val
210                 215                 220
Ala Glu Gln Pro Glu Tyr Val Val Phe Asn Gly His Val Gly Ala Ile
225                 230                 235                 240
Ala Gly Asp Asn Ala Leu Lys Ala Lys Ala Gly Glu Thr Val Arg Met
                245                 250                 255
Tyr Val Gly Asn Gly Gly Pro Asn Leu Val Ser Ser Phe His Val Ile
            260                 265                 270
Gly Glu Ile Phe Asp Lys Val Tyr Val Glu Gly Gly Lys Leu Ile Asn
        275                 280                 285
Glu Asn Val Gln Ser Thr Ile Val Pro Ala Gly Gly Ser Ala Ile Val
    290                 295                 300
```

```
Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 41
<211> LENGTH: 336
<212> TYPE: PRT
<213> ORGANISM: Neisseria meningitidis

<400> SEQUENCE: 41

Ala Ser Leu Phe Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
            20                  25                  30

Ala Gln Thr Ala Ala Glu Thr Pro Ser Gly Glu Leu Pro Val Ile Asp
            35                  40                  45

Ala Val Thr Thr His Ala Pro Glu Val Pro Ala Ile Asp Arg Asp
            50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
            115                 120                 125

His Ala Ala Thr Gly Gln Gly Gly Ala Ala Ala Thr Phe Thr Ala
            130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
            195                 200                 205

Lys Lys Gly Ala Gln Gly Leu Gln Pro Phe Asp Met Asp Lys Ala Val
210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Gly Lys Leu Ile Asn
            275                 280                 285

Glu Asn Val Gln Ser Thr Ile Val Pro Ala Gly Gly Ser Ala Ile Val
            290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 42
```

```
<211> LENGTH: 386
<212> TYPE: PRT
<213> ORGANISM: Neisseria meningitidis

<400> SEQUENCE: 42

Met Lys Arg Gln Ala Leu Ala Ala Ile Ile Ala Ser Met Phe Ala Leu
1               5                   10                  15

Ala Ala Cys Gly Gly Glu Pro Ala Ala Gln Thr Pro Ala Ala Ser Ala
            20                  25                  30

Glu Ala Ser Ser Ala Ala Gln Thr Ala Ala Glu Thr Pro Ser Gly
        35                  40                  45

Glu Leu Pro Val Ile Asp Ala Val Thr Thr His Ala Pro Glu Val Pro
50                  55                  60

Pro Ala Ile Asp Arg Asp Tyr Pro Ala Lys Val Arg Val Lys Met Glu
65                  70                  75                  80

Thr Val Glu Lys Thr Met Lys Met Asp Asp Gly Val Glu Tyr Arg Tyr
                85                  90                  95

Trp Thr Phe Asp Gly Asp Val Pro Gly Arg Met Ile Arg Val Arg Glu
            100                 105                 110

Gly Asp Thr Val Glu Val Glu Phe Ser Asn Asn Pro Ser Ser Thr Val
        115                 120                 125

Pro His Asn Val Asp Phe His Ala Ala Thr Gly Gln Gly Gly Gly Ala
    130                 135                 140

Ala Ala Thr Phe Thr Ala Pro Gly Arg Thr Ser Thr Phe Ser Phe Lys
145                 150                 155                 160

Ala Leu Gln Pro Gly Leu Tyr Ile Tyr His Cys Ala Val Ala Pro Val
                165                 170                 175

Gly Met His Ile Ala Asn Gly Met Tyr Gly Leu Ile Leu Val Glu Pro
            180                 185                 190

Lys Glu Gly Leu Pro Lys Val Asp Lys Glu Phe Tyr Ile Val Gln Gly
        195                 200                 205

Asp Phe Tyr Thr Lys Gly Lys Lys Gly Ala Gln Gly Leu Gln Pro Phe
    210                 215                 220

Asp Met Asp Lys Ala Ile Ala Glu Gln Pro Glu Tyr Val Val Phe Asn
225                 230                 235                 240

Gly His Val Gly Ala Ile Ala Gly Asp Asn Ala Leu Lys Ala Lys Ala
                245                 250                 255

Gly Glu Thr Val Arg Met Tyr Val Gly Asn Gly Pro Asn Leu Val
            260                 265                 270

Ser Ser Phe His Val Ile Gly Glu Ile Phe Asp Lys Val Tyr Val Glu
        275                 280                 285

Gly Gly Lys Leu Ile Asn Glu Asn Val Gln Ser Thr Ile Val Pro Ala
    290                 295                 300

Gly Gly Ser Ala Ile Val Glu Phe Lys Val Asp Ile Pro Gly Ser Tyr
305                 310                 315                 320

Thr Leu Val Asp His Ser Ile Phe Arg Ala Phe Asn Lys Gly Ala Leu
                325                 330                 335

Gly Gln Leu Lys Val Glu Gly Ala Glu Asn Pro Glu Ile Met Thr Gln
            340                 345                 350

Lys Leu Ser Asp Thr Ala Tyr Ala Gly Asn Gly Ala Ala Pro Ala Ala
        355                 360                 365

Ser Ala Pro Ala Ala Ser Ala Pro Ala Ala Ser Ala Pro Ala Lys Ser
    370                 375                 380

Asp Tyr
```

<210> SEQ ID NO 43
<211> LENGTH: 332
<212> TYPE: PRT
<213> ORGANISM: Neisseria meningitidis

<400> SEQUENCE: 43

| | | | | | | | | | | | | | | |
|---|---|---|---|---|---|---|---|---|---|---|---|---|---|---|
| Ala | Ser | Leu | Phe | Ala | Leu | Ala | Ala | Cys | Gly | Gly | Glu | Pro | Ala | Gln |
| 1 | | | | 5 | | | | | 10 | | | | | 15 |
| Ala | Pro | Ala | Ala | Ser | Ala | Glu | Ala | Ala | Ser | Ser | Ala | Ala | Gln | Ala | Ala |
| | | 20 | | | | | 25 | | | | | 30 | | | |
| Ala | Glu | Thr | Pro | Ala | Gly | Glu | Leu | Pro | Val | Ile | Asp | Ala | Val | Thr | Thr |
| | | | 35 | | | | | 40 | | | | | 45 | | |
| His | Ala | Pro | Glu | Val | Pro | Ala | Ile | Asp | Arg | Asp | Tyr | Pro | Ala | Lys |
| | 50 | | | | | 55 | | | | | 60 | | | |
| Val | Arg | Val | Lys | Met | Glu | Thr | Val | Glu | Lys | Thr | Met | Thr | Met | Glu | Asp |
| 65 | | | | | 70 | | | | | 75 | | | | | 80 |
| Gly | Val | Glu | Tyr | Arg | Tyr | Trp | Thr | Phe | Asp | Gly | Asp | Val | Pro | Gly | Arg |
| | | | | 85 | | | | | 90 | | | | | 95 | |
| Met | Ile | Arg | Val | Arg | Glu | Gly | Asp | Thr | Val | Glu | Val | Glu | Phe | Ser | Asn |
| | | | 100 | | | | | 105 | | | | | 110 | | |
| Asn | Pro | Ser | Ser | Thr | Val | Pro | His | Asn | Val | Asp | Phe | His | Ala | Ala | Thr |
| | | | 115 | | | | | 120 | | | | | 125 | | |
| Gly | Gln | Gly | Gly | Gly | Ala | Ala | Ala | Thr | Phe | Thr | Ala | Pro | Gly | Arg | Thr |
| | 130 | | | | | 135 | | | | | 140 | | | | |
| Ser | Thr | Phe | Ser | Phe | Lys | Ala | Leu | Gln | Pro | Gly | Leu | Tyr | Ile | Tyr | His |
| 145 | | | | | 150 | | | | | 155 | | | | | 160 |
| Cys | Ala | Val | Ala | Pro | Val | Gly | Met | His | Ile | Ala | Asn | Gly | Met | Tyr | Gly |
| | | | | 165 | | | | | 170 | | | | | 175 | |
| Leu | Ile | Leu | Val | Glu | Pro | Lys | Glu | Gly | Leu | Pro | Lys | Val | Asp | Lys | Glu |
| | | | 180 | | | | | 185 | | | | | 190 | | |
| Phe | Tyr | Ile | Val | Gln | Gly | Asp | Phe | Tyr | Thr | Lys | Gly | Lys | Lys | Gly | Ala |
| | | 195 | | | | | 200 | | | | | 205 | | | |
| Gln | Gly | Leu | Gln | Pro | Phe | Asp | Met | Asp | Lys | Ala | Ile | Ala | Glu | Gln | Pro |
| | 210 | | | | | 215 | | | | | 220 | | | | |
| Glu | Tyr | Val | Val | Phe | Asn | Gly | His | Val | Gly | Ala | Ile | Ala | Gly | Asp | Asn |
| 225 | | | | | 230 | | | | | 235 | | | | | 240 |
| Ala | Leu | Lys | Ala | Lys | Ala | Gly | Glu | Thr | Val | Arg | Met | Tyr | Val | Gly | Asn |
| | | | 245 | | | | | 250 | | | | | 255 | | |
| Gly | Gly | Pro | Asn | Leu | Val | Ser | Ser | Phe | His | Val | Ile | Gly | Glu | Ile | Phe |
| | | | 260 | | | | | 265 | | | | | 270 | | |
| Asp | Lys | Val | Tyr | Val | Glu | Gly | Gly | Lys | Leu | Ile | Asn | Glu | Asn | Val | Gln |
| | | 275 | | | | | 280 | | | | | 285 | | | |
| Ser | Thr | Ile | Val | Pro | Ala | Gly | Gly | Ser | Ala | Ile | Val | Glu | Phe | Lys | Val |
| | 290 | | | | | 295 | | | | | 300 | | | | |
| Asp | Ile | Pro | Gly | Ser | Tyr | Thr | Leu | Val | Asp | His | Ser | Ile | Phe | Arg | Ala |
| 305 | | | | | 310 | | | | | 315 | | | | | 320 |
| Phe | Asn | Lys | Gly | Ala | Leu | Gly | Gln | Leu | Lys | Val | Glu |
| | | | | 325 | | | | | 330 | | |

<210> SEQ ID NO 44
<211> LENGTH: 332
<212> TYPE: PRT
<213> ORGANISM: Neisseria meningitidis

<400> SEQUENCE: 44

```
Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Ala Ala
            20                  25                  30

Ala Glu Thr Pro Ala Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Thr Met Lys Met Asp Asp
65                  70                  75                  80

Gly Val Glu Tyr Arg Tyr Trp Thr Phe Asp Gly Asp Val Pro Gly Arg
                85                  90                  95

Met Ile Arg Val Arg Glu Gly Asp Thr Val Glu Val Glu Phe Ser Asn
            100                 105                 110

Asn Pro Ser Ser Thr Val Pro His Asn Val Asp Phe His Ala Ala Thr
        115                 120                 125

Gly Gln Gly Gly Gly Ala Ala Ala Thr Phe Thr Ala Pro Gly Arg Thr
130                 135                 140

Ser Thr Phe Ser Phe Lys Ala Leu Gln Pro Gly Leu Tyr Ile Tyr His
145                 150                 155                 160

Cys Ala Val Ala Pro Val Gly Met His Ile Ala Asn Gly Met Tyr Gly
                165                 170                 175

Leu Ile Leu Val Glu Pro Lys Glu Gly Leu Pro Lys Val Asp Lys Glu
            180                 185                 190

Phe Tyr Ile Val Gln Gly Asp Phe Tyr Thr Lys Gly Lys Lys Gly Ala
        195                 200                 205

Gln Gly Leu Gln Pro Phe Asp Met Asp Lys Ala Ile Ala Glu Gln Pro
    210                 215                 220

Glu Tyr Val Val Phe Asn Gly His Val Gly Ala Ile Ala Gly Asp Asn
225                 230                 235                 240

Ala Leu Lys Ala Lys Ala Gly Glu Thr Val Arg Met Tyr Val Gly Asn
                245                 250                 255

Gly Gly Pro Asn Leu Val Ser Ser Phe His Val Ile Gly Glu Ile Phe
            260                 265                 270

Asp Lys Val Tyr Val Glu Gly Gly Lys Leu Ile Asn Glu Asn Val Gln
        275                 280                 285

Ser Thr Ile Val Pro Ala Gly Gly Ser Ala Ile Val Glu Phe Lys Val
    290                 295                 300

Asp Ile Pro Gly Ser Tyr Thr Leu Val Asp His Ser Ile Phe Arg Ala
305                 310                 315                 320

Phe Asn Lys Gly Ala Leu Gly Gln Leu Lys Val Glu
                325                 330
```

<210> SEQ ID NO 45
<211> LENGTH: 332
<212> TYPE: PRT
<213> ORGANISM: Neisseria meningitidis

<400> SEQUENCE: 45

```
Ala Ser Met Phe Ala Leu Ala Ala Cys Gly Gly Glu Pro Ala Ala Gln
1               5                   10                  15

Thr Pro Ala Ala Ser Ala Glu Ala Ala Ser Ser Ala Ala Gln Thr Ala
            20                  25                  30
```

```
Ala Glu Thr Pro Ala Gly Glu Leu Pro Val Ile Asp Ala Val Thr Thr
             35                  40                  45

His Ala Pro Glu Val Pro Pro Ala Ile Asp Arg Asp Tyr Pro Ala Lys
 50                  55                  60

Val Arg Val Lys Met Glu Thr Val Glu Lys Thr Met Lys Met Asp Asp
 65                  70                  75                  80

Gly Val Glu Tyr Arg Tyr Trp Thr Phe Asp Gly Asp Val Pro Gly Arg
                 85                  90                  95

Met Ile Arg Val Arg Glu Gly Asp Thr Val Glu Val Glu Phe Ser Asn
                100                 105                 110

Asn Pro Ser Ser Thr Val Pro His Asn Val Asp Phe His Ala Ala Thr
            115                 120                 125

Gly Gln Gly Gly Gly Ala Ala Ala Thr Phe Thr Ala Pro Gly Arg Thr
130                 135                 140

Ser Thr Phe Ser Phe Lys Ala Leu Gln Pro Gly Leu Tyr Ile Tyr His
145                 150                 155                 160

Cys Ala Val Ala Pro Val Gly Met His Ile Ala Asn Gly Met Tyr Gly
                165                 170                 175

Leu Ile Leu Val Glu Pro Lys Glu Gly Leu Pro Lys Val Asp Lys Glu
            180                 185                 190

Phe Tyr Ile Val Gln Gly Asp Phe Tyr Thr Lys Gly Lys Lys Gly Ala
        195                 200                 205

Gln Gly Leu Gln Pro Phe Asp Met Asp Lys Ala Ile Ala Glu Gln Pro
    210                 215                 220

Glu Tyr Val Val Phe Asn Gly His Val Gly Ala Ile Ala Gly Asp Asn
225                 230                 235                 240

Ala Leu Lys Ala Lys Ala Gly Glu Thr Val Arg Met Tyr Val Gly Asn
                245                 250                 255

Gly Gly Pro Asn Leu Val Ser Ser Phe His Val Ile Gly Glu Ile Phe
            260                 265                 270

Asp Lys Val Tyr Val Glu Gly Gly Lys Leu Ile Asn Glu Asn Val Gln
        275                 280                 285

Ser Thr Ile Val Pro Ala Gly Gly Ser Ala Ile Val Glu Phe Lys Val
    290                 295                 300

Asp Ile Pro Gly Ser Tyr Thr Leu Val Asp His Ser Ile Phe Arg Ala
305                 310                 315                 320

Phe Asn Lys Gly Ala Leu Gly Gln Leu Lys Val Glu
                325                 330

<210> SEQ ID NO 46
<211> LENGTH: 332
<212> TYPE: PRT
<213> ORGANISM: Neisseria meningitidis

<400> SEQUENCE: 46

Ala Ser Met Phe Ala Leu Ala Ala Cys Gly Gly Glu Pro Ala Ala Gln
 1               5                  10                  15

Thr Pro Ala Ala Ser Ala Glu Ala Ala Ser Ser Ala Ala Gln Thr Ala
                20                  25                  30

Ala Glu Thr Pro Ala Gly Glu Leu Pro Val Ile Asp Ala Val Thr Thr
             35                  40                  45

His Ala Pro Glu Val Pro Pro Ala Ile Asp Arg Asp Tyr Pro Ala Lys
 50                  55                  60

Val Arg Val Lys Met Glu Thr Val Glu Lys Thr Met Lys Met Asp Asp
 65                  70                  75                  80
```

```
Gly Val Glu Tyr Arg Tyr Trp Thr Phe Asp Gly Asp Val Pro Gly Arg
                85                  90                  95

Met Ile Arg Val Arg Glu Gly Asp Thr Val Glu Val Glu Phe Ser Asn
            100                 105                 110

Asn Pro Ser Ser Thr Val Pro His Asn Val Asp Phe His Ala Ala Thr
        115                 120                 125

Gly Gln Gly Gly Gly Ala Ala Ala Thr Phe Thr Ala Pro Gly Arg Thr
    130                 135                 140

Ser Thr Phe Ser Phe Lys Ala Leu Gln Pro Gly Leu Tyr Ile Tyr His
145                 150                 155                 160

Cys Ala Val Ala Pro Val Gly Met His Ile Ala Asn Gly Met Tyr Gly
                165                 170                 175

Leu Ile Leu Val Glu Pro Lys Glu Gly Leu Pro Lys Val Asp Lys Glu
            180                 185                 190

Phe Tyr Ile Val Gln Gly Asp Phe Tyr Thr Lys Gly Lys Lys Gly Ala
        195                 200                 205

Gln Gly Leu Gln Pro Phe Asp Met Asp Lys Ala Ile Ala Glu Gln Pro
    210                 215                 220

Glu Tyr Val Val Phe Asn Gly His Val Gly Ala Ile Ala Gly Asp Asn
225                 230                 235                 240

Ala Leu Lys Ala Lys Ala Gly Glu Thr Val Arg Met Tyr Val Gly Asn
                245                 250                 255

Gly Gly Pro Asn Leu Val Ser Ser Phe His Val Ile Gly Glu Ile Phe
            260                 265                 270

Asp Lys Val Tyr Val Glu Gly Gly Lys Leu Ile Asn Glu Asn Val Gln
        275                 280                 285

Ser Thr Ile Val Pro Ala Gly Gly Ser Ala Ile Val Glu Phe Lys Val
    290                 295                 300

Asp Ile Pro Gly Ser Tyr Thr Leu Val Asp His Ser Ile Phe Arg Ala
305                 310                 315                 320

Phe Asn Lys Gly Ala Leu Gly Gln Leu Lys Val Glu
                325                 330

<210> SEQ ID NO 47
<211> LENGTH: 85
<212> TYPE: PRT
<213> ORGANISM: Neisseria meningitidis

<400> SEQUENCE: 47

Met Lys Arg Gln Ala Leu Ala Ala Met Ile Ala Ser Leu Phe Ala Leu
1               5                   10                  15

Ala Ala Cys Gly Gly Glu Pro Ala Ala Gln Pro Ala Ala Ser Ala
                20                  25                  30

Glu Ala Ala Ser Ser Ala Ala Gln Thr Ala Glu Thr Pro Thr Gly
            35                  40                  45

Glu Leu Pro Val Ile Asp Ala Val Thr Thr His Ala Pro Glu Val Pro
    50                  55                  60

Pro Ala Ile Asp Arg Asp Tyr Pro Ala Lys Val Arg Val Lys Met Glu
65                  70                  75                  80

Thr Val Glu Lys Pro
                85

<210> SEQ ID NO 48
<211> LENGTH: 85
<212> TYPE: PRT
```

<213> ORGANISM: Neisseria meningitidis

<400> SEQUENCE: 48

```
Met Lys Arg Gln Ala Leu Ala Ala Met Ile Ala Ser Leu Phe Ala Leu
1               5                   10                  15
Ala Ala Cys Gly Gly Glu Pro Ala Ala Gln Ala Pro Ala Ala Ser Ala
            20                  25                  30
Glu Ala Ala Ser Ser Ala Ala Gln Thr Ala Ala Glu Thr Pro Thr Gly
        35                  40                  45
Glu Leu Pro Val Ile Asp Ala Val Thr Thr His Ala Pro Glu Val Pro
    50                  55                  60
Pro Ala Ile Asp Arg Asp Tyr Pro Ala Lys Val Arg Val Lys Met Glu
65                  70                  75                  80
Thr Val Glu Lys Pro
                85
```

<210> SEQ ID NO 49
<211> LENGTH: 85
<212> TYPE: PRT
<213> ORGANISM: Neisseria meningitidis

<400> SEQUENCE: 49

```
Met Lys Arg Gln Ala Leu Ala Ala Met Ile Ala Ser Leu Phe Ala Leu
1               5                   10                  15
Ala Ala Cys Gly Gly Glu Pro Ala Ala Gln Ala Pro Ala Ala Ser Ala
            20                  25                  30
Glu Ala Ala Ser Ser Ala Ala Gln Thr Ala Ala Glu Thr Pro Thr Gly
        35                  40                  45
Glu Leu Pro Val Ile Asp Ala Val Thr Thr His Ala Pro Glu Val Pro
    50                  55                  60
Pro Ala Ile Asp Arg Asp Tyr Pro Ala Lys Val Arg Val Lys Met Glu
65                  70                  75                  80
Thr Val Glu Lys Pro
                85
```

<210> SEQ ID NO 50
<211> LENGTH: 85
<212> TYPE: PRT
<213> ORGANISM: Neisseria meningitidis

<400> SEQUENCE: 50

```
Met Lys Arg Gln Ala Leu Ala Ala Met Ile Ala Ser Leu Phe Ala Leu
1               5                   10                  15
Ala Ala Cys Gly Gly Glu Pro Ala Ala Gln Ala Pro Ala Ala Ser Ala
            20                  25                  30
Glu Ala Ala Ser Ser Ala Ala Gln Thr Ala Ala Glu Thr Pro Thr Gly
        35                  40                  45
Glu Leu Pro Val Ile Asp Ala Val Thr Thr His Ala Pro Glu Val Pro
    50                  55                  60
Pro Ala Ile Asp Arg Asp Tyr Pro Ala Lys Val Arg Val Lys Met Glu
65                  70                  75                  80
Thr Val Glu Lys Pro
                85
```

<210> SEQ ID NO 51
<211> LENGTH: 75
<212> TYPE: PRT
<213> ORGANISM: Neisseria meningitidis

<400> SEQUENCE: 51

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Pro
65                  70                  75

<210> SEQ ID NO 52
<211> LENGTH: 75
<212> TYPE: PRT
<213> ORGANISM: Neisseria meningitidis

<400> SEQUENCE: 52

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Pro
65                  70                  75

<210> SEQ ID NO 53
<211> LENGTH: 75
<212> TYPE: PRT
<213> ORGANISM: Neisseria meningitidis

<400> SEQUENCE: 53

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Pro
65                  70                  75

<210> SEQ ID NO 54
<211> LENGTH: 75
<212> TYPE: PRT
<213> ORGANISM: Neisseria meningitidis

<400> SEQUENCE: 54

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr

```
                35                  40                  45

His Ala Pro Glu Val Pro Pro Ala Ile Asp Arg Asp Tyr Pro Ala Lys
     50                  55                  60

Val Arg Val Lys Met Glu Thr Val Glu Lys Pro
 65                  70                  75

<210> SEQ ID NO 55
<211> LENGTH: 75
<212> TYPE: PRT
<213> ORGANISM: Neisseria meningitidis

<400> SEQUENCE: 55

Ala Ser Leu Phe Ala Leu Ala Ala Cys Gly Gly Glu Pro Ala Ala Gln
 1               5                  10                  15

Ala Pro Ala Ala Ser Ala Glu Ala Ala Ser Ser Ala Ala Gln Thr Ala
                20                  25                  30

Ala Glu Thr Pro Thr Gly Glu Leu Pro Val Ile Asp Ala Val Thr Thr
                35                  40                  45

His Ala Pro Glu Val Pro Pro Ala Ile Asp Arg Asp Tyr Pro Ala Lys
     50                  55                  60

Val Arg Val Lys Met Glu Thr Val Glu Lys Pro
 65                  70                  75

<210> SEQ ID NO 56
<211> LENGTH: 75
<212> TYPE: PRT
<213> ORGANISM: Neisseria meningitidis

<400> SEQUENCE: 56

Ala Ser Leu Phe Ala Leu Ala Ala Cys Gly Gly Glu Pro Ala Ala Gln
 1               5                  10                  15

Ala Pro Ala Ala Ser Ala Glu Ala Ala Ser Ser Ala Ala Gln Thr Ala
                20                  25                  30

Ala Glu Thr Pro Thr Gly Glu Leu Pro Val Ile Asp Ala Val Thr Thr
                35                  40                  45

His Ala Pro Glu Val Pro Pro Ala Ile Asp Arg Asp Tyr Pro Ala Lys
     50                  55                  60

Val Arg Val Lys Met Glu Thr Val Glu Lys Pro
 65                  70                  75

<210> SEQ ID NO 57
<211> LENGTH: 75
<212> TYPE: PRT
<213> ORGANISM: Neisseria meningitidis

<400> SEQUENCE: 57

Ala Ser Leu Phe Ala Leu Ala Ala Cys Gly Gly Glu Pro Ala Ala Gln
 1               5                  10                  15

Ala Pro Ala Ala Ser Ala Glu Ala Ala Ser Ser Ala Ala Gln Thr Ala
                20                  25                  30

Ala Glu Thr Pro Thr Gly Glu Leu Pro Val Ile Asp Ala Val Thr Thr
                35                  40                  45

His Ala Pro Glu Val Pro Pro Ala Ile Asp Arg Asp Tyr Pro Ala Lys
     50                  55                  60

Val Arg Val Lys Met Glu Thr Val Glu Lys Pro
 65                  70                  75

<210> SEQ ID NO 58
```

```
<211> LENGTH: 75
<212> TYPE: PRT
<213> ORGANISM: Neisseria meningitidis

<400> SEQUENCE: 58

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Pro
65                  70                  75

<210> SEQ ID NO 59
<211> LENGTH: 75
<212> TYPE: PRT
<213> ORGANISM: Neisseria meningitidis

<400> SEQUENCE: 59

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Pro
65                  70                  75

<210> SEQ ID NO 60
<211> LENGTH: 96
<212> TYPE: PRT
<213> ORGANISM: Neisseria meningitidis

<400> SEQUENCE: 60

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Pro Arg Pro Trp Lys Thr
65                  70                  75                  80

Val Trp Asn Thr Ala Thr Gly His Leu Thr Ala Thr Phe Arg Val Ala
                85                  90                  95

<210> SEQ ID NO 61
<211> LENGTH: 337
<212> TYPE: PRT
<213> ORGANISM: Neisseria meningitidis

<400> SEQUENCE: 61

Ala Ser Val Phe Ala Leu Ala Ala Cys Gly Glu Gln Ala Ala Lys Pro
```

```
  1               5                  10                 15
Ala Glu Thr Pro Ala Ala Thr Ala Ser Ala Glu Ala Pro Ala Ala Ser
                20                  25                 30

Asn Ser Gln Ala Ala Ala Glu Thr Pro Ser Ser Glu Leu Pro Val Ile
                35                  40                 45

Asp Ala Ile Val Thr His Ala Pro Glu Val Pro Pro Thr Asp Arg
 50                 55                  60

Asp His Pro Ala Lys Val Arg Val Lys Met Glu Thr Val Glu Lys Thr
 65                 70                  75                 80

Met Lys Met Asp Asp Gly Val Glu Tyr His Tyr Trp Thr Phe Asp Gly
                85                  90                 95

Asp Val Pro Gly Arg Met Ile Arg Val Arg Glu Gly Asp Thr Val Glu
                100                 105                110

Val Glu Phe Ser Asn Asn Pro Ser Ser Thr Val Pro His Asn Val Asp
                115                 120                125

Phe His Ala Ala Thr Gly Gln Gly Gly Gly Ala Ala Ala Thr Phe Thr
130                 135                 140

Ala Pro Gly Arg Thr Ser Thr Phe Ser Phe Lys Ala Leu Gln Ala Gly
145                 150                 155                160

Leu Tyr Ile Tyr His Cys Ala Val Ala Pro Val Gly Met His Ile Ala
                165                 170                175

Asn Gly Met Tyr Gly Leu Ile Leu Val Glu Pro Lys Glu Gly Leu Pro
                180                 185                190

Lys Val Asp Lys Glu Phe Tyr Ile Val Gln Gly Asp Phe Tyr Thr Lys
                195                 200                205

Gly Lys Lys Gly Ala Gln Gly Leu Gln Pro Phe Asp Met Asp Lys Ala
                210                 215                220

Ile Ala Glu Gln Pro Glu Tyr Val Val Phe Asn Gly His Val Gly Ser
225                 230                 235                240

Ile Ala Gly Asp Asn Ala Leu Lys Ala Lys Ala Gly Glu Thr Ile Arg
                245                 250                255

Met Tyr Val Gly Asn Gly Gly Pro Asn Leu Val Ser Ser Phe His Val
                260                 265                270

Ile Gly Glu Ile Phe Asp Lys Val Tyr Val Glu Gly Lys Leu Ile
                275                 280                285

Asn Glu Asn Val Gln Ser Thr Ile Val Pro Ala Gly Gly Ser Ala Ile
                290                 295                300

Val Glu Phe Lys Val Asp Ile Pro Gly Ser Tyr Thr Leu Val Asp His
305                 310                 315                320

Ser Ile Phe Arg Ala Phe Asn Lys Gly Ala Leu Gly Gln Leu Lys Val
                325                 330                335

Glu
```

<210> SEQ ID NO 62
<211> LENGTH: 337
<212> TYPE: PRT
<213> ORGANISM: Neisseria meningitidis

<400> SEQUENCE: 62

```
Ala Ser Val Phe Ala Leu Ala Ala Cys Gly Glu Gln Ala Ala Lys Pro
 1               5                  10                 15

Ala Glu Thr Pro Ala Ala Thr Ala Ser Ala Glu Ala Pro Ala Ala Ser
                20                  25                 30

Asn Ser Gln Ala Ala Ala Glu Thr Pro Ser Ser Glu Leu Pro Val Ile
```

```
                  35                  40                  45
Asp Ala Ile Val Thr His Ala Pro Glu Val Pro Pro Thr Asp Arg
 50                  55                  60

Asp His Pro Ala Lys Val Arg Val Lys Met Glu Thr Val Glu Lys Thr
 65                  70                  75                  80

Met Lys Met Asp Asp Gly Val Glu Tyr His Tyr Trp Thr Phe Asp Gly
                 85                  90                  95

Asp Val Pro Gly Arg Met Ile Arg Val Arg Glu Gly Asp Thr Val Glu
                100                 105                 110

Val Glu Phe Ser Asn Asn Pro Ser Ser Thr Val Pro His Asn Val Asp
            115                 120                 125

Phe His Ala Ala Thr Gly Gln Gly Gly Ala Ala Ala Thr Phe Thr
        130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 63
<211> LENGTH: 337
<212> TYPE: PRT
<213> ORGANISM: Neisseria meningitidis

<400> SEQUENCE: 63

Ala Ser Val Phe Ala Leu Ala Ala Cys Gly Glu Gln Ala Ala Lys Pro
  1               5                  10                  15

Ala Glu Thr Pro Ala Ala Thr Ala Ser Ala Glu Ala Pro Ala Ala Ser
                 20                  25                  30

Asn Ser Gln Ala Ala Ala Glu Thr Pro Ser Ser Glu Leu Pro Val Ile
             35                  40                  45

Asp Ala Ile Val Thr His Ala Pro Glu Val Pro Pro Thr Asp Arg
         50                  55                  60

Asp His Pro Ala Lys Val Arg Val Lys Met Glu Thr Val Glu Lys Thr
```

```
            65                  70                  75                  80
        Met Lys Met Asp Asp Gly Val Glu Tyr His Tyr Trp Thr Phe Asp Gly
                            85                  90                  95

Asp Val Pro Gly Arg Met Ile Arg Val Arg Glu Gly Asp Thr Val Glu
                        100                 105                 110

Val Glu Phe Ser Asn Asn Pro Ser Ser Thr Val Pro His Asn Val Asp
                    115                 120                 125

Phe His Ala Ala Thr Gly Gln Gly Gly Ala Ala Ala Thr Phe Thr
                130                 135                 140

Ala Pro Gly Arg Thr Ser Thr Phe Ser Phe Lys Ala Leu Gln Ala Gly
        145                 150                 155                 160

Leu Tyr Ile Tyr His Cys Ala Val Ala Pro Val Gly Met His Ile Ala
                            165                 170                 175

Asn Gly Met Tyr Gly Leu Ile Leu Val Glu Pro Lys Glu Gly Leu Pro
                        180                 185                 190

Lys Val Asp Lys Glu Phe Tyr Ile Val Gln Gly Asp Phe Tyr Thr Lys
                    195                 200                 205

Gly Lys Lys Gly Ala Gln Gly Leu Gln Pro Phe Asp Met Asp Lys Ala
                210                 215                 220

Ile Ala Glu Gln Pro Glu Tyr Val Val Phe Asn Gly His Val Gly Ser
        225                 230                 235                 240

Ile Ala Gly Asp Asn Ala Leu Lys Ala Lys Ala Gly Glu Thr Ile Arg
                            245                 250                 255

Met Tyr Val Gly Asn Gly Gly Pro Asn Leu Val Ser Ser Phe His Val
                        260                 265                 270

Ile Gly Glu Ile Phe Asp Lys Val Tyr Val Glu Gly Lys Leu Ile
                    275                 280                 285

Asn Glu Asn Val Gln Ser Thr Ile Val Pro Ala Gly Ser Ala Ile
                290                 295                 300

Val Glu Phe Lys Val Asp Ile Pro Gly Ser Tyr Thr Leu Val Asp His
        305                 310                 315                 320

Ser Ile Phe Arg Ala Phe Asn Lys Gly Ala Leu Gly Gln Leu Lys Val
                            325                 330                 335

Glu

<210> SEQ ID NO 64
<211> LENGTH: 337
<212> TYPE: PRT
<213> ORGANISM: Neisseria meningitidis

<400> SEQUENCE: 64

Ala Ser Val Phe Ala Leu Ala Ala Cys Gly Glu Gln Ala Ala Lys Pro
        1               5                   10                  15

Ala Glu Thr Pro Ala Ala Thr Ala Ser Ala Glu Ala Pro Ala Ala Ser
                        20                  25                  30

Asn Ser Gln Ala Ala Ala Glu Thr Pro Ser Ser Glu Leu Pro Val Ile
                    35                  40                  45

Asp Ala Ile Val Thr His Ala Pro Glu Val Pro Pro Thr Asp Arg
                50                  55                  60

Asp His Pro Ala Lys Val Arg Val Lys Met Glu Thr Val Glu Lys Thr
        65                  70                  75                  80

Met Lys Met Asp Asp Gly Val Glu Tyr His Tyr Trp Thr Phe Asp Gly
                            85                  90                  95

Asp Val Pro Gly Arg Met Ile Arg Val Arg Glu Gly Asp Thr Val Glu
```

```
            100                 105                 110
Val Glu Phe Ser Asn Asn Pro Ser Ser Thr Val Pro His Asn Val Asp
            115                 120                 125

Phe His Ala Ala Thr Gly Gln Gly Gly Gly Ala Ala Ala Thr Phe Thr
        130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 65
<211> LENGTH: 337
<212> TYPE: PRT
<213> ORGANISM: Neisseria meningitidis

<400> SEQUENCE: 65

Ala Ser Val Phe Ala Leu Ala Ala Cys Gly Glu Gln Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Gly Ala Ala Ala Thr Phe Thr
```

```
            130                 135                 140
Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
            165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
                195                 200                 205

Gly Lys Lys Gly Ala Gln Gly Leu Gln Pro Phe Asp Met Asp Lys Ala
            210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
                260                 265                 270

Ile Gly Glu Ile Phe Asp Lys Val Tyr Val Glu Gly Gly Lys Leu Ile
                275                 280                 285

Asn Glu Asn Val Gln Ser Thr Ile Val Pro Ala Gly Gly Ser Ala Ile
            290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 66
<211> LENGTH: 337
<212> TYPE: PRT
<213> ORGANISM: Neisseria meningitidis

<400> SEQUENCE: 66

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Gly Asp Thr Val Glu
            100                 105                 110

Val Glu Phe Ser Asn Asn Pro Ser Ser Thr Val Pro His Asn Val Asp
                115                 120                 125

Phe His Ala Ala Thr Gly Gln Gly Gly Ala Ala Thr Phe Thr
            130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
```

```
                    165                 170                 175
Asn Gly Met Tyr Gly Leu Ile Leu Val Glu Pro Lys Glu Gly Leu Pro
                180                 185                 190
Lys Val Asp Lys Glu Phe Tyr Ile Val Gln Gly Asp Phe Tyr Thr Lys
            195                 200                 205
Gly Lys Lys Gly Ala Gln Gly Leu Gln Pro Phe Asp Met Asp Lys Ala
        210                 215                 220
Ile Ala Glu Gln Pro Glu Tyr Val Val Phe Asn Gly His Val Gly Ser
225                 230                 235                 240
Ile Ala Gly Asp Asn Ala Leu Lys Ala Lys Ala Gly Glu Thr Ile Arg
                245                 250                 255
Met Tyr Val Gly Asn Gly Gly Pro Asn Leu Val Ser Ser Phe His Val
                260                 265                 270
Ile Gly Glu Ile Phe Asp Lys Val Tyr Val Glu Gly Gly Lys Leu Ile
            275                 280                 285
Asn Glu Asn Val Gln Ser Thr Ile Val Pro Ala Gly Gly Ser Ala Ile
        290                 295                 300
Val Glu Phe Lys Val Asp Ile Pro Gly Ser Tyr Thr Leu Val Asp His
305                 310                 315                 320
Ser Ile Phe Arg Ala Phe Asn Lys Gly Ala Leu Gly Gln Leu Lys Val
                325                 330                 335
Glu

<210> SEQ ID NO 67
<211> LENGTH: 337
<212> TYPE: PRT
<213> ORGANISM: Neisseria meningitidis

<400> SEQUENCE: 67

Ala Ser Val Phe Ala Leu Ala Ala Cys Gly Glu Gln Ala Ala Lys Pro
1               5                   10                  15
Ala Glu Thr Pro Ala Ala Thr Ala Ser Ala Glu Ala Pro Ala Ala Ser
            20                  25                  30
Asn Ser Gln Ala Ala Ala Glu Thr Pro Ser Ser Glu Leu Pro Val Ile
        35                  40                  45
Asp Ala Ile Val Thr His Ala Pro Glu Val Pro Pro Thr Asp Arg
    50                  55                  60
Asp His Pro Ala Lys Val Arg Val Lys Met Glu Thr Val Glu Lys Thr
65                  70                  75                  80
Met Lys Met Asp Asp Gly Val Glu Tyr His Tyr Trp Thr Phe Asp Gly
                85                  90                  95
Asp Val Pro Gly Arg Met Ile Arg Val Arg Glu Gly Asp Thr Val Glu
            100                 105                 110
Val Glu Phe Ser Asn Asn Pro Ser Ser Thr Val Pro His Asn Val Asp
        115                 120                 125
Phe His Ala Ala Thr Gly Gln Gly Gly Ala Ala Thr Phe Thr
    130                 135                 140
Ala Pro Gly Arg Thr Ser Thr Phe Ser Phe Lys Ala Leu Gln Ala Gly
145                 150                 155                 160
Leu Tyr Ile Tyr His Cys Ala Val Ala Pro Val Gly Met His Ile Ala
                165                 170                 175
Asn Gly Met Tyr Gly Leu Ile Leu Val Glu Pro Lys Glu Gly Leu Pro
            180                 185                 190
Lys Val Asp Lys Glu Phe Tyr Ile Val Gln Gly Asp Phe Tyr Thr Lys
```

```
              195                 200                 205
Gly Lys Lys Gly Ala Gln Gly Leu Gln Pro Phe Asp Met Asp Lys Ala
        210                 215                 220
Ile Ala Glu Gln Pro Glu Tyr Val Val Phe Asn Gly His Val Gly Ser
225                 230                 235                 240
Ile Ala Gly Asp Asn Ala Leu Lys Ala Lys Ala Gly Glu Thr Ile Arg
            245                 250                 255
Met Tyr Val Gly Asn Gly Gly Pro Asn Leu Val Ser Ser Phe His Val
        260                 265                 270
Ile Gly Glu Ile Phe Asp Lys Val Tyr Val Glu Gly Lys Leu Ile
    275                 280                 285
Asn Glu Asn Val Gln Ser Thr Ile Val Pro Ala Gly Ser Ala Ile
    290                 295                 300
Val Glu Phe Lys Val Asp Ile Pro Gly Ser Tyr Thr Leu Val Asp His
305                 310                 315                 320
Ser Ile Phe Arg Ala Phe Asn Lys Gly Ala Leu Gly Gln Leu Lys Val
            325                 330                 335
Glu
```

<210> SEQ ID NO 68
<211> LENGTH: 337
<212> TYPE: PRT
<213> ORGANISM: Neisseria meningitidis

<400> SEQUENCE: 68

```
Ala Ser Val Phe Ala Leu Ala Ala Cys Gly Glu Gln Ala Ala Lys Pro
1               5                   10                  15
Ala Glu Thr Pro Ala Ala Thr Ala Ser Ala Glu Ala Pro Ala Ala Ser
            20                  25                  30
Asn Ser Gln Ala Ala Ala Glu Thr Pro Ser Ser Glu Leu Pro Val Ile
        35                  40                  45
Asp Ala Ile Val Thr His Ala Pro Glu Val Pro Pro Thr Asp Arg
    50                  55                  60
Asp His Pro Ala Lys Val Arg Val Lys Met Glu Thr Val Glu Lys Thr
65                  70                  75                  80
Met Lys Met Asp Asp Gly Val Glu Tyr His Tyr Trp Thr Phe Asp Gly
                85                  90                  95
Asp Val Pro Gly Arg Met Ile Arg Val Arg Glu Gly Asp Thr Val Glu
            100                 105                 110
Val Glu Phe Ser Asn Asn Pro Ser Ser Thr Val Pro His Asn Val Asp
        115                 120                 125
Phe His Ala Ala Thr Gly Gln Gly Gly Ala Ala Ala Thr Phe Thr
    130                 135                 140
Ala Pro Gly Arg Thr Ser Thr Phe Ser Phe Lys Ala Leu Gln Ala Gly
145                 150                 155                 160
Leu Tyr Ile Tyr His Cys Ala Val Ala Pro Val Gly Met His Ile Ala
                165                 170                 175
Asn Gly Met Tyr Gly Leu Ile Leu Val Glu Pro Lys Glu Gly Leu Pro
            180                 185                 190
Lys Val Asp Lys Glu Phe Tyr Ile Val Gln Gly Asp Phe Tyr Thr Lys
        195                 200                 205
Gly Lys Lys Gly Ala Gln Gly Leu Gln Pro Phe Asp Met Asp Lys Ala
    210                 215                 220
Ile Ala Glu Gln Pro Glu Tyr Val Val Phe Asn Gly His Val Gly Ser
```

```
225                 230                 235                 240
Ile Ala Gly Asp Asn Ala Leu Lys Ala Lys Ala Gly Glu Thr Ile Arg
                245                 250                 255
Met Tyr Val Gly Asn Gly Gly Pro Asn Leu Val Ser Ser Phe His Val
                260                 265                 270
Ile Gly Glu Ile Phe Asp Lys Val Tyr Val Gly Gly Lys Leu Ile
                275                 280                 285
Asn Glu Asn Val Gln Ser Thr Ile Val Pro Ala Gly Ser Ala Ile
290                 295                 300
Val Glu Phe Lys Val Asp Ile Pro Gly Ser Tyr Thr Leu Val Asp His
305                 310                 315                 320
Ser Ile Phe Arg Ala Phe Asn Lys Gly Ala Leu Gly Gln Leu Lys Val
                325                 330                 335
Glu

<210> SEQ ID NO 69
<211> LENGTH: 337
<212> TYPE: PRT
<213> ORGANISM: Neisseria meningitidis

<400> SEQUENCE: 69

Ala Ser Val Phe Ala Leu Ala Ala Cys Gly Glu Gln Ala Ala Lys Pro
1               5                   10                  15
Ala Glu Thr Pro Ala Ala Thr Ala Ser Ala Glu Ala Pro Ala Ala Ser
                20                  25                  30
Asn Ser Gln Ala Ala Ala Glu Thr Pro Ser Ser Glu Leu Pro Val Ile
            35                  40                  45
Asp Ala Ile Val Thr His Ala Pro Glu Val Pro Pro Thr Asp Arg
        50                  55                  60
Asp His Pro Ala Lys Val Arg Val Lys Met Glu Thr Val Glu Lys Thr
65                  70                  75                  80
Met Lys Met Asp Asp Gly Val Glu Tyr His Tyr Trp Thr Phe Asp Gly
                85                  90                  95
Asp Val Pro Gly Arg Met Ile Arg Val Arg Glu Gly Asp Thr Val Glu
                100                 105                 110
Val Glu Phe Ser Asn Asn Pro Ser Ser Thr Val Pro His Asn Val Asp
            115                 120                 125
Phe His Ala Ala Thr Gly Gln Gly Gly Ala Ala Ala Thr Phe Thr
        130                 135                 140
Ala Pro Gly Arg Thr Ser Thr Phe Ser Phe Lys Ala Leu Gln Ala Gly
145                 150                 155                 160
Leu Tyr Ile Tyr His Cys Ala Val Ala Pro Val Gly Met His Ile Ala
                165                 170                 175
Asn Gly Met Tyr Gly Leu Ile Leu Val Glu Pro Lys Glu Gly Leu Pro
                180                 185                 190
Lys Val Asp Lys Glu Phe Tyr Ile Val Gln Gly Asp Phe Tyr Thr Lys
            195                 200                 205
Gly Lys Lys Gly Ala Gln Gly Leu Gln Pro Phe Asp Met Asp Lys Ala
        210                 215                 220
Ile Ala Glu Gln Pro Glu Tyr Val Val Phe Asn Gly His Val Gly Ser
225                 230                 235                 240
Ile Ala Gly Asp Asn Ala Leu Lys Ala Lys Ala Gly Glu Thr Ile Arg
                245                 250                 255
Met Tyr Val Gly Asn Gly Gly Pro Asn Leu Val Ser Ser Phe His Val
```

```
              260                 265                 270
Ile Gly Glu Ile Phe Asp Lys Val Tyr Val Glu Gly Gly Lys Leu Ile
            275                 280                 285

Asn Glu Asn Val Gln Ser Thr Ile Val Pro Ala Gly Gly Ser Ala Ile
        290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 70
<211> LENGTH: 337
<212> TYPE: PRT
<213> ORGANISM: Neisseria meningitidis

<400> SEQUENCE: 70

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
```

```
            290                 295                 300
Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 71
<211> LENGTH: 337
<212> TYPE: PRT
<213> ORGANISM: Neisseria meningitidis

<400> SEQUENCE: 71

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
                20                  25                  30

Asn Ser Gln Ala Ala Glu Thr Pro Ser Ser Glu Leu Pro Val Ile
            35                  40                  45

Asp Ala Ile Val Thr His Ala Pro Glu Val Pro Pro Thr Asp Arg
50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
                100                 105                 110

Val Glu Phe Ser Asn Asn Pro Ser Ser Thr Val Pro His Asn Val Asp
                115                 120                 125

Phe His Ala Ala Thr Gly Gln Gly Gly Ala Ala Ala Thr Phe Thr
            130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
                180                 185                 190

Lys Val Asp Lys Glu Phe Tyr Ile Val Gln Gly Asp Phe Tyr Thr Lys
                195                 200                 205

Gly Lys Lys Gly Ala Gln Gly Leu Gln Pro Phe Asp Met Asp Lys Ala
                210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
                260                 265                 270

Ile Gly Glu Ile Phe Asp Lys Val Tyr Val Glu Gly Gly Lys Leu Ile
                275                 280                 285

Asn Glu Asn Val Gln Ser Thr Ile Val Pro Ala Gly Gly Ser Ala Ile
                290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
```

```
                    325                 330                 335

Glu

<210> SEQ ID NO 72
<211> LENGTH: 390
<212> TYPE: PRT
<213> ORGANISM: Neisseria meningitidis

<400> SEQUENCE: 72

Met Lys Arg Gln Ala Leu Ala Ala Met Ile Ala Ser Leu Phe Ala Leu
1               5                   10                  15

Ala Ala Cys Gly Gly Glu Pro Ala Ala Gln Pro Ala Glu Thr Pro
            20                  25                  30

Ala Ala Ala Ala Glu Ala Ala Ser Ser Ala Ala Gln Thr Ala Ala Glu
        35                  40                  45

Thr Pro Ser Gly Glu Leu Pro Val Ile Asp Ala Val Thr Thr His Ala
    50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
        115                 120                 125

Ser Ser Thr Val Pro His Asn Val Asp Phe His Ala Ala Thr Gly Gln
130                 135                 140

Gly Gly Gly Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Lys Gly Ala Gln Gly
    210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Met Thr Gln Lys Leu Ser Asp Thr Ala Tyr Ala Gly Asn Gly Ala
```

355                 360                 365
Ala Pro Ala Ala Ser Ala Pro Ala Ala Ser Ala Pro Ala Ala Ser Ala
                370                 375                 380

Ser Glu Lys Ser Val Tyr
385                 390

<210> SEQ ID NO 73
<211> LENGTH: 390
<212> TYPE: PRT
<213> ORGANISM: Neisseria meningitidis

<400> SEQUENCE: 73

Met Lys Arg Gln Ala Leu Ala Ala Met Ile Ala Ser Leu Phe Ala Leu
1               5                   10                  15

Ala Ala Cys Gly Gly Glu Pro Ala Ala Gln Pro Ala Glu Thr Pro
            20                  25                  30

Ala Ala Ala Ala Glu Ala Ala Ser Ser Ala Ala Gln Thr Ala Ala Glu
            35                  40                  45

Thr Pro Ser Gly Glu Leu Pro Val Ile Asp Ala Val Thr Thr His Ala
50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
        115                 120                 125

Ser Ser Thr Val Pro His Asn Val Asp Phe His Ala Ala Thr Gly Gln
    130                 135                 140

Gly Gly Gly Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Lys Gly Ala Gln Gly
    210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

```
Lys Gly Ala Leu Gly Gln Leu Lys Val Gly Ala Glu Asn Pro Glu
                340                 345                 350

Ile Met Thr Gln Lys Leu Ser Asp Thr Ala Tyr Ala Gly Asn Gly Ala
        355                 360                 365

Ala Pro Ala Ala Ser Ala Pro Ala Ala Ser Ala Pro Ala Ala Ser Ala
370                 375                 380

Ser Glu Lys Ser Val Tyr
385             390

<210> SEQ ID NO 74
<211> LENGTH: 390
<212> TYPE: PRT
<213> ORGANISM: Neisseria meningitidis

<400> SEQUENCE: 74

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Glu Thr Pro
            20                  25                  30

Ala Ala Ala Ala Glu Ala Ala Ser Ser Ala Ala Gln Thr Ala Ala Glu
        35                  40                  45

Thr Pro Ser Gly Glu Leu Pro Val Ile Asp Ala Val Thr Thr His Ala
    50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
                85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Phe Ser Asn Asn Pro
        115                 120                 125

Ser Ser Thr Val Pro His Asn Val Asp Phe His Ala Ala Thr Gly Gln
    130                 135                 140

Gly Gly Gly Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Gly Ala Gln Gly
    210                 215                 220

Leu Gln Pro Phe Asp Met Asp Lys Ala Val Glu Gln Pro Glu Tyr
225                 230                 235                 240

Val Val Phe Asn Gly His Val Gly Ala Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
    290                 295                 300

Ile Val Pro Ala Gly Gly Ser Ala Ile Val Glu Phe Lys Val Asp Ile
305                 310                 315                 320
```

```
Pro Gly Ser Tyr Thr Leu Val Asp His Ser Ile Phe Arg Ala Phe Asn
            325                 330                 335

Lys Gly Ala Leu Gly Gln Leu Lys Val Glu Gly Ala Glu Asn Pro Glu
            340                 345                 350

Ile Ile Thr Gln Lys Leu Ser Asp Thr Ala Tyr Ala Gly Asn Gly Ala
            355                 360                 365

Ala Pro Ala Ala Ser Ala Pro Ala Ala Ser Ala Pro Ala Ala Ser Ala
            370                 375                 380

Ser Glu Lys Ser Val Tyr
385                 390

<210> SEQ ID NO 75
<211> LENGTH: 390
<212> TYPE: PRT
<213> ORGANISM: Neisseria meningitidis

<400> SEQUENCE: 75

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Glu Thr Pro
            20                  25                  30

Ala Ala Ala Ala Glu Ala Ala Ser Ser Ala Ala Gln Thr Ala Ala Glu
            35                  40                  45

Thr Pro Ser Gly Glu Leu Pro Val Ile Asp Ala Val Thr Thr His Ala
50                  55                  60

Pro Glu Val Pro Pro Ala Ile Asp Arg Asp Tyr Pro Ala Lys Val Arg
65                  70                  75                  80

Val Lys Met Glu Thr Val Glu Lys Thr Met Thr Met Glu Asp Gly Val
            85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
            115                 120                 125

Ser Ser Thr Val Pro His Asn Val Asp Phe His Ala Ala Thr Gly Gln
130                 135                 140

Gly Gly Gly Ala Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
            165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
            195                 200                 205

Ile Val Gln Gly Asp Phe Tyr Thr Lys Gly Lys Lys Gly Ala Gln Gly
            210                 215                 220

Leu Gln Pro Phe Asp Met Asp Lys Ala Val Ala Glu Gln Pro Glu Tyr
225                 230                 235                 240

Val Val Phe Asn Gly His Val Gly Ala Ile Ala Gly Asp Asn Ala Leu
            245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
            275                 280                 285

Val Tyr Val Glu Gly Gly Lys Leu Ile Asn Glu Asn Val Gln Ser Thr
```

```
            290             295             300
Ile Val Pro Ala Gly Gly Ser Ala Ile Val Glu Phe Lys Val Asp Ile
305             310             315             320

Pro Gly Ser Tyr Thr Leu Val Asp His Ser Ile Phe Arg Ala Phe Asn
            325             330             335

Lys Gly Ala Leu Gly Gln Leu Lys Val Glu Ala Glu Asn Pro Glu
            340             345             350

Ile Met Thr Gln Lys Leu Ser Asp Thr Ala Tyr Ala Gly Asn Gly Ala
            355             360             365

Ala Pro Ala Ala Ser Ala Pro Ala Ala Ser Ala Pro Ala Ala Ser Ala
370             375             380

Ser Glu Lys Ser Val Tyr
385             390

<210> SEQ ID NO 76
<211> LENGTH: 336
<212> TYPE: PRT
<213> ORGANISM: Neisseria meningitidis

<400> SEQUENCE: 76

Ala Ser Leu Phe Ala Leu Ala Ala Cys Gly Gly Glu Pro Ala Ala Gln
1               5               10              15

Ala Pro Ala Glu Thr Pro Ala Ala Ala Glu Ala Ala Ser Ser Ala
            20              25              30

Ala Gln Thr Ala Ala Glu Thr Pro Ser Gly Glu Leu Pro Val Ile Asp
            35              40              45

Ala Val Thr Thr His Ala Pro Glu Val Pro Pro Ala Ile Asp Arg Asp
50              55              60

Tyr Pro Ala Lys Val Arg Val Lys Met Glu Thr Val Glu Lys Thr Met
65              70              75              80

Thr Met Glu Asp Gly Val Glu Tyr Arg Tyr Trp Thr Phe Asp Gly Asp
                85              90              95

Val Pro Gly Arg Met Ile Arg Val Arg Glu Gly Asp Thr Val Glu Val
            100             105             110

Glu Phe Ser Asn Asn Pro Ser Ser Thr Val Pro His Asn Val Asp Phe
            115             120             125

His Ala Ala Thr Gly Gln Gly Gly Gly Ala Ala Thr Phe Thr Ala
            130             135             140

Pro Gly Arg Thr Ser Thr Phe Ser Phe Lys Ala Leu Gln Pro Gly Leu
145             150             155             160

Tyr Ile Tyr His Cys Ala Val Ala Pro Val Gly Met His Ile Ala Asn
                165             170             175

Gly Met Tyr Gly Leu Ile Leu Val Glu Pro Lys Glu Gly Leu Pro Lys
            180             185             190

Val Asp Lys Glu Phe Tyr Ile Val Gln Gly Asp Phe Tyr Thr Lys Gly
            195             200             205

Lys Lys Gly Ala Gln Gly Leu Gln Pro Phe Asp Met Asp Lys Ala Val
            210             215             220

Ala Glu Gln Pro Glu Tyr Val Val Phe Asn Gly His Val Gly Ala Ile
225             230             235             240

Ala Gly Asp Asn Ala Leu Lys Ala Lys Ala Gly Glu Thr Val Arg Met
                245             250             255

Tyr Val Gly Asn Gly Gly Pro Asn Leu Val Ser Ser Phe His Val Ile
            260             265             270
```

```
Gly Glu Ile Phe Asp Lys Val Tyr Val Glu Gly Lys Leu Ile Asn
            275                 280                 285

Glu Asn Val Gln Ser Thr Ile Val Pro Ala Gly Ser Ala Ile Val
            290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 77
<211> LENGTH: 336
<212> TYPE: PRT
<213> ORGANISM: Neisseria meningitidis

<400> SEQUENCE: 77

Ala Ser Leu Phe Ala Leu Ala Ala Cys Gly Gly Glu Pro Ala Ala Gln
1               5                   10                  15

Ala Pro Ala Glu Thr Pro Ala Ala Ser Ala Glu Ala Ala Ser Ser Ala
            20                  25                  30

Ala Gln Thr Ala Ala Glu Thr Pro Ser Gly Glu Leu Pro Val Ile Asp
            35                  40                  45

Ala Val Thr Thr His Ala Pro Glu Val Pro Pro Ala Ile Asp Arg Asp
50                  55                  60

Tyr Pro Ala Lys Val Arg Val Lys Met Glu Thr Val Glu Lys Thr Met
65                  70                  75                  80

Lys Met Asp Asp Gly Val Glu Tyr His Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
            115                 120                 125

His Ala Ala Thr Gly Gln Gly Gly Gly Ala Ala Ala Thr Phe Thr Ala
            130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
            195                 200                 205

Lys Lys Gly Ala Gln Gly Leu Gln Pro Phe Asp Met Asp Lys Ala Ile
            210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Lys Leu Ile Asn
            275                 280                 285

Glu Asn Val Gln Ser Thr Ile Val Pro Ala Gly Gly Ser Ala Ile Val
            290                 295                 300

Glu Phe Lys Val Asp Ile Pro Gly Ser Tyr Thr Leu Val Asp His Ser
305                 310                 315                 320
```

```
Ile Phe Arg Ala Phe Asn Lys Gly Ala Leu Gly Gln Leu Lys Val Glu
            325                 330                 335

<210> SEQ ID NO 78
<211> LENGTH: 336
<212> TYPE: PRT
<213> ORGANISM: Neisseria meningitidis

<400> SEQUENCE: 78

Ala Ser Leu Phe Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
            20                  25                  30

Ala Gln Thr Ala Ala Glu Thr Pro Ser Gly Glu Leu Pro Val Ile Asp
            35                  40                  45

Ala Val Thr Thr His Ala Pro Glu Val Pro Ala Ile Asp Arg Asp
        50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
        115                 120                 125

His Ala Ala Thr Gly Gln Gly Gly Ala Ala Thr Phe Thr Ala
130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
        195                 200                 205

Lys Lys Gly Ala Gln Gly Leu Gln Pro Phe Asp Met Asp Lys Ala Val
    210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Gly Lys Leu Ile Asn
        275                 280                 285

Glu Asn Val Gln Ser Thr Ile Val Pro Ala Gly Ser Ala Ile Val
    290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 79
<211> LENGTH: 336
<212> TYPE: PRT
```

<213> ORGANISM: Neisseria meningitidis

<400> SEQUENCE: 79

| | | | | | | | | | | | | | | |
|---|---|---|---|---|---|---|---|---|---|---|---|---|---|---|
| Ala | Ser | Leu | Phe | Ala | Leu | Ala | Ala | Cys | Gly | Gly | Glu | Pro | Pro | Ala | Gln |
| 1 | | | | 5 | | | | | 10 | | | | | 15 |
| Ala | Pro | Ala | Glu | Thr | Pro | Ala | Ala | Ala | Glu | Ala | Ala | Ser | Ser | Ala |
| | | | 20 | | | | | 25 | | | | | 30 | |
| Ala | Gln | Thr | Ala | Ala | Glu | Thr | Pro | Ser | Gly | Glu | Leu | Pro | Val | Ile | Asp |
| | | 35 | | | | | 40 | | | | | 45 | | |
| Ala | Val | Thr | Thr | His | Ala | Pro | Glu | Val | Pro | Pro | Ala | Ile | Asp | Arg | Asp |
| | 50 | | | | | 55 | | | | | 60 | | | | |
| Tyr | Pro | Ala | Lys | Val | Arg | Val | Lys | Met | Glu | Thr | Val | Glu | Lys | Thr | Met |
| 65 | | | | | 70 | | | | | 75 | | | | | 80 |
| Thr | Met | Glu | Asp | Gly | Val | Glu | Tyr | Arg | Tyr | Trp | Thr | Phe | Asp | Gly | Asp |
| | | | | 85 | | | | | 90 | | | | | 95 | |
| Val | Pro | Gly | Arg | Met | Ile | Arg | Val | Arg | Glu | Gly | Asp | Thr | Val | Glu | Val |
| | | | 100 | | | | | 105 | | | | | 110 | | |
| Glu | Phe | Ser | Asn | Asn | Pro | Ser | Ser | Thr | Val | Pro | His | Asn | Val | Asp | Phe |
| | | | 115 | | | | | 120 | | | | | 125 | | |
| His | Ala | Thr | Gly | Gln | Gly | Gly | Gly | Ala | Ala | Ala | Thr | Phe | Thr | Ala |
| | 130 | | | | | 135 | | | | | 140 | | | | |
| Pro | Gly | Arg | Thr | Ser | Thr | Phe | Ser | Phe | Lys | Ala | Leu | Gln | Pro | Gly | Leu |
| 145 | | | | | 150 | | | | | 155 | | | | | 160 |
| Tyr | Ile | Tyr | His | Cys | Ala | Val | Ala | Pro | Val | Gly | Met | His | Ile | Ala | Asn |
| | | | | 165 | | | | | 170 | | | | | 175 | |
| Gly | Met | Tyr | Gly | Leu | Ile | Leu | Val | Glu | Pro | Lys | Glu | Gly | Leu | Pro | Lys |
| | | | 180 | | | | | 185 | | | | | 190 | | |
| Val | Asp | Lys | Glu | Phe | Tyr | Ile | Val | Gln | Gly | Asp | Phe | Tyr | Thr | Lys | Gly |
| | | 195 | | | | | 200 | | | | | 205 | | | |
| Lys | Lys | Gly | Ala | Gln | Gly | Leu | Gln | Pro | Phe | Asp | Met | Asp | Lys | Ala | Val |
| 210 | | | | | 215 | | | | | 220 | | | | | |
| Ala | Glu | Gln | Pro | Glu | Tyr | Val | Val | Phe | Asn | Gly | His | Val | Gly | Ala | Ile |
| 225 | | | | | 230 | | | | | 235 | | | | | 240 |
| Ala | Gly | Asp | Asn | Ala | Leu | Lys | Ala | Lys | Ala | Gly | Glu | Thr | Val | Arg | Met |
| | | | | 245 | | | | | 250 | | | | | 255 | |
| Tyr | Val | Gly | Asn | Gly | Gly | Pro | Asn | Leu | Val | Ser | Ser | Phe | His | Val | Ile |
| | | | 260 | | | | | 265 | | | | | 270 | | |
| Gly | Glu | Ile | Phe | Asp | Lys | Val | Tyr | Val | Glu | Gly | Gly | Lys | Leu | Ile | Asn |
| | | 275 | | | | | 280 | | | | | 285 | | | |
| Glu | Asn | Val | Gln | Ser | Thr | Ile | Val | Pro | Ala | Gly | Gly | Ser | Ala | Ile | Val |
| | 290 | | | | | 295 | | | | | 300 | | | | |
| Glu | Phe | Lys | Val | Asp | Ile | Pro | Gly | Ser | Tyr | Thr | Leu | Val | Asp | His | Ser |
| 305 | | | | | 310 | | | | | 315 | | | | | 320 |
| Ile | Phe | Arg | Ala | Phe | Asn | Lys | Gly | Ala | Leu | Gly | Gln | Leu | Lys | Val | Glu |
| | | | | 325 | | | | | 330 | | | | | 335 | |

<210> SEQ ID NO 80
<211> LENGTH: 336
<212> TYPE: PRT
<213> ORGANISM: Neisseria meningitidis

<400> SEQUENCE: 80

| | | | | | | | | | | | | | | | |
|---|---|---|---|---|---|---|---|---|---|---|---|---|---|---|---|
| Ala | Ser | Leu | Leu | Ala | Leu | Ala | Ala | Cys | Gly | Gly | Glu | Pro | Ala | Ala | Gln |
| 1 | | | | 5 | | | | | 10 | | | | | 15 | |
| Ala | Pro | Ala | Glu | Thr | Pro | Ala | Ala | Ala | Glu | Ala | Ala | Ser | Ser | Ala |

```
            20                  25                  30
Ala Gln Thr Ala Ala Glu Thr Pro Ser Gly Glu Leu Pro Val Ile Asp
            35                  40                  45

Ala Val Thr Thr His Ala Pro Glu Val Pro Pro Ala Ile Asp Arg Asp
        50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
        115                 120                 125

His Ala Ala Thr Gly Gln Gly Gly Ala Ala Thr Phe Thr Ala
        130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
        195                 200                 205

Lys Lys Gly Ala Gln Gly Leu Gln Pro Phe Asp Met Asp Lys Ala Val
210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Gly Lys Leu Ile Asn
        275                 280                 285

Glu Asn Val Gln Ser Thr Ile Val Pro Ala Gly Gly Ser Ala Ile Val
        290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 81
<211> LENGTH: 336
<212> TYPE: PRT
<213> ORGANISM: Neisseria meningitidis

<400> SEQUENCE: 81

Ala Ser Leu Leu Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
            20                  25                  30

Ala Gln Thr Ala Ala Glu Thr Pro Ser Gly Glu Leu Pro Val Ile Asp
            35                  40                  45

Ala Val Thr Thr His Ala Pro Glu Val Pro Pro Ala Ile Asp Arg Asp
        50                  55                  60
```

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
        115                 120                 125

His Ala Ala Thr Gly Gln Gly Gly Ala Ala Thr Phe Thr Ala
    130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
            180                 185                 190

Val Asp Lys Glu Phe Tyr Ile Val Gln Gly Asp Phe Tyr Thr Lys Gly
        195                 200                 205

Lys Lys Gly Ala Gln Gly Leu Gln Pro Phe Asp Met Asp Lys Ala Val
210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
            260                 265                 270

Gly Glu Ile Phe Asp Lys Val Tyr Val Glu Gly Gly Lys Leu Ile Asn
        275                 280                 285

Glu Asn Val Gln Ser Thr Ile Val Pro Ala Gly Gly Ser Ala Ile Val
290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 82
<211> LENGTH: 336
<212> TYPE: PRT
<213> ORGANISM: Neisseria meningitidis

<400> SEQUENCE: 82

Ala Ser Leu Phe Ala Leu Ala Ala Cys Gly Gly Glu Pro Ala Ala Gln
1               5                   10                  15

Ala Pro Ala Glu Thr Pro Ala Ala Ala Glu Ala Ala Ser Ser Ala
            20                  25                  30

Ala Gln Thr Ala Ala Glu Thr Pro Ser Gly Glu Leu Pro Val Ile Asp
        35                  40                  45

Ala Val Thr Thr His Ala Pro Glu Val Pro Pro Ala Ile Asp Arg Asp
    50                  55                  60

Tyr Pro Ala Lys Val Arg Val Lys Met Glu Thr Val Glu Lys Thr Met
65                  70                  75                  80

Thr Met Glu Asp Gly Val Glu Tyr Arg Tyr Trp Thr Phe Asp Gly Asp
                85                  90                  95

Val Pro Gly Arg Met Ile Arg Val Arg Glu Gly Asp Thr Val Glu Val
            100                 105                 110

Glu Phe Ser Asn Asn Pro Ser Ser Thr Val Pro His Asn Val Asp Phe
              115                 120                 125

His Ala Ala Thr Gly Gln Gly Gly Ala Ala Thr Phe Thr Ala
130                 135                 140

Pro Gly Arg Thr Ser Thr Phe Ser Phe Lys Ala Leu Gln Pro Gly Leu
145                 150                 155                 160

Tyr Ile Tyr His Cys Ala Val Ala Pro Val Gly Met His Ile Ala Asn
                165                 170                 175

Gly Met Tyr Gly Leu Ile Leu Val Glu Pro Lys Glu Gly Leu Pro Lys
                180                 185                 190

Val Asp Lys Glu Phe Tyr Ile Val Gln Gly Asp Phe Tyr Thr Lys Gly
                195                 200                 205

Lys Lys Gly Ala Gln Gly Leu Gln Pro Phe Asp Met Asp Lys Ala Val
210                 215                 220

Ala Glu Gln Pro Glu Tyr Val Val Phe Asn Gly His Val Gly Ala Ile
225                 230                 235                 240

Ala Gly Asp Asn Ala Leu Lys Ala Lys Ala Gly Glu Thr Val Arg Met
                245                 250                 255

Tyr Val Gly Asn Gly Gly Pro Asn Leu Val Ser Ser Phe His Val Ile
                260                 265                 270

Gly Glu Ile Phe Asp Lys Val Tyr Val Glu Gly Gly Lys Leu Ile Asn
                275                 280                 285

Glu Asn Val Gln Ser Thr Ile Val Pro Ala Gly Gly Ser Ala Ile Val
                290                 295                 300

Glu Phe Lys Val Asp Ile Pro Gly Ser Tyr Thr Leu Val Asp His Ser
305                 310                 315                 320

Ile Phe Arg Ala Phe Asn Lys Gly Ala Leu Gly Gln Leu Lys Val Glu
                325                 330                 335

<210> SEQ ID NO 83
<211> LENGTH: 386
<212> TYPE: PRT
<213> ORGANISM: Neisseria meningitidis

<400> SEQUENCE: 83

Met Lys Arg Gln Ala Leu Ala Ala Ile Ile Ala Ser Met Phe Ala Leu
1               5                   10                  15

Ala Ala Cys Gly Gly Glu Pro Ala Ala Gln Thr Pro Ala Ala Ser Ala
                20                  25                  30

Glu Ala Ala Ser Ser Ala Ala Gln Thr Ala Ala Glu Thr Pro Ser Gly
                35                  40                  45

Glu Leu Pro Val Ile Asp Ala Val Thr His Ala Pro Glu Val Pro
50                  55                  60

Pro Ala Ile Asp Arg Asp Tyr Pro Ala Lys Val Arg Val Lys Met Glu
65                  70                  75                  80

Thr Val Glu Lys Thr Met Lys Met Asp Asp Gly Val Glu Tyr Arg Tyr
                85                  90                  95

Trp Thr Phe Asp Gly Asp Val Pro Gly Arg Met Ile Arg Val Arg Glu
                100                 105                 110

Gly Asp Thr Val Glu Val Glu Phe Ser Asn Asn Pro Ser Ser Thr Val
                115                 120                 125

Pro His Asn Val Asp Phe His Ala Ala Thr Gly Gln Gly Gly Gly Ala
                130                 135                 140

Ala Ala Thr Phe Thr Ala Pro Gly Arg Thr Ser Thr Phe Ser Phe Lys

```
                145                 150                 155                 160
Ala Leu Gln Pro Gly Leu Tyr Ile Tyr His Cys Ala Val Ala Pro Val
                165                 170                 175

Gly Met His Ile Ala Asn Gly Met Tyr Gly Leu Ile Leu Val Glu Pro
                180                 185                 190

Lys Glu Gly Leu Pro Lys Val Asp Lys Glu Phe Tyr Ile Val Gln Gly
                195                 200                 205

Asp Phe Tyr Thr Lys Gly Lys Lys Gly Ala Gln Gly Leu Gln Pro Phe
210                 215                 220

Asp Met Asp Lys Ala Ile Ala Glu Gln Pro Glu Tyr Val Val Phe Asn
225                 230                 235                 240

Gly His Val Gly Ala Ile Ala Gly Asp Asn Ala Leu Lys Ala Lys Ala
                245                 250                 255

Gly Glu Thr Val Arg Met Tyr Val Gly Asn Gly Pro Asn Leu Val
                260                 265                 270

Ser Ser Phe His Val Ile Gly Glu Ile Phe Asp Lys Val Tyr Val Glu
                275                 280                 285

Gly Gly Lys Leu Ile Asn Glu Asn Val Gln Ser Thr Ile Val Pro Ala
                290                 295                 300

Gly Gly Ser Ala Ile Val Glu Phe Lys Val Asp Ile Pro Gly Ser Tyr
305                 310                 315                 320

Thr Leu Val Asp His Ser Ile Phe Arg Ala Phe Asn Lys Gly Ala Leu
                325                 330                 335

Gly Gln Leu Lys Val Glu Gly Ala Glu Asn Pro Glu Ile Met Thr Gln
                340                 345                 350

Lys Leu Ser Asp Thr Ala Tyr Ala Gly Asn Gly Ala Ala Pro Ala Ala
                355                 360                 365

Ser Ala Pro Ala Ala Ser Ala Pro Ala Ala Ser Ala Pro Ala Lys Ser
                370                 375                 380

Asp Tyr
385

<210> SEQ ID NO 84
<211> LENGTH: 332
<212> TYPE: PRT
<213> ORGANISM: Neisseria meningitidis

<400> SEQUENCE: 84

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Ala Ala
                20                  25                  30

Ala Glu Thr Pro Ala Gly Glu Leu Pro Val Ile Asp Ala Val Thr Thr
                35                  40                  45

His Ala Pro Glu Val Pro Pro Ala Ile Asp Arg Asp Tyr Pro Ala Lys
                50                  55                  60

Val Arg Val Lys Met Glu Thr Val Glu Lys Thr Met Thr Met Glu Asp
65                  70                  75                  80

Gly Val Glu Tyr Arg Tyr Trp Thr Phe Asp Gly Asp Val Pro Gly Arg
                85                  90                  95

Met Ile Arg Val Arg Glu Gly Asp Thr Val Glu Val Glu Phe Ser Asn
                100                 105                 110

Asn Pro Ser Ser Thr Val Pro His Asn Val Asp Phe His Ala Ala Thr
                115                 120                 125
```

```
Gly Gln Gly Gly Gly Ala Ala Thr Phe Thr Ala Pro Gly Arg Thr
    130                 135                 140
Ser Thr Phe Ser Phe Lys Ala Leu Gln Pro Gly Leu Tyr Ile Tyr His
145                 150                 155                 160
Cys Ala Val Ala Pro Val Gly Met His Ile Ala Asn Gly Met Tyr Gly
                165                 170                 175
Leu Ile Leu Val Glu Pro Lys Glu Gly Leu Pro Lys Val Asp Lys Glu
                180                 185                 190
Phe Tyr Ile Val Gln Gly Asp Phe Tyr Thr Lys Gly Lys Lys Gly Ala
            195                 200                 205
Gln Gly Leu Gln Pro Phe Asp Met Asp Lys Ala Ile Ala Glu Gln Pro
    210                 215                 220
Glu Tyr Val Val Phe Asn Gly His Val Gly Ala Ile Ala Gly Asp Asn
225                 230                 235                 240
Ala Leu Lys Ala Lys Ala Gly Glu Thr Val Arg Met Tyr Val Gly Asn
                245                 250                 255
Gly Gly Pro Asn Leu Val Ser Ser Phe His Val Ile Gly Glu Ile Phe
                260                 265                 270
Asp Lys Val Tyr Val Glu Gly Lys Leu Ile Asn Glu Asn Val Gln
            275                 280                 285
Ser Thr Ile Val Pro Ala Gly Gly Ser Ala Ile Val Glu Phe Lys Val
    290                 295                 300
Asp Ile Pro Gly Ser Tyr Thr Leu Val Asp His Ser Ile Phe Arg Ala
305                 310                 315                 320
Phe Asn Lys Gly Ala Leu Gly Gln Leu Lys Val Glu
                325                 330

<210> SEQ ID NO 85
<211> LENGTH: 332
<212> TYPE: PRT
<213> ORGANISM: Neisseria meningitidis

<400> SEQUENCE: 85

Ala Ser Leu Phe Ala Leu Ala Ala Cys Gly Gly Glu Pro Ala Ala Gln
1               5                   10                  15
Ala Pro Ala Ala Ser Ala Glu Ala Ala Ser Ser Ala Ala Gln Ala Ala
                20                  25                  30
Ala Glu Thr Pro Ala Gly Glu Leu Pro Val Ile Asp Ala Val Thr Thr
            35                  40                  45
His Ala Pro Glu Val Pro Pro Ala Ile Asp Arg Asp Tyr Pro Ala Lys
    50                  55                  60
Val Arg Val Lys Met Glu Thr Val Glu Lys Thr Met Lys Met Asp Asp
65                  70                  75                  80
Gly Val Glu Tyr Arg Tyr Trp Thr Phe Asp Gly Asp Val Pro Gly Arg
                85                  90                  95
Met Ile Arg Val Arg Glu Gly Asp Thr Val Glu Val Glu Phe Ser Asn
                100                 105                 110
Asn Pro Ser Ser Thr Val Pro His Asn Val Asp Phe His Ala Ala Thr
            115                 120                 125
Gly Gln Gly Gly Gly Ala Ala Thr Phe Thr Ala Pro Gly Arg Thr
    130                 135                 140
Ser Thr Phe Ser Phe Lys Ala Leu Gln Pro Gly Leu Tyr Ile Tyr His
145                 150                 155                 160
Cys Ala Val Ala Pro Val Gly Met His Ile Ala Asn Gly Met Tyr Gly
                165                 170                 175
```

```
Leu Ile Leu Val Glu Pro Lys Glu Gly Leu Pro Lys Val Asp Lys Glu
                180                 185                 190

Phe Tyr Ile Val Gln Gly Asp Phe Tyr Thr Lys Gly Lys Lys Gly Ala
            195                 200                 205

Gln Gly Leu Gln Pro Phe Asp Met Asp Lys Ala Ile Ala Glu Gln Pro
        210                 215                 220

Glu Tyr Val Val Phe Asn Gly His Val Gly Ala Ile Ala Gly Asp Asn
225                 230                 235                 240

Ala Leu Lys Ala Lys Ala Gly Glu Thr Val Arg Met Tyr Val Gly Asn
                245                 250                 255

Gly Gly Pro Asn Leu Val Ser Ser Phe His Val Ile Gly Glu Ile Phe
            260                 265                 270

Asp Lys Val Tyr Val Glu Gly Gly Lys Leu Ile Asn Glu Asn Val Gln
        275                 280                 285

Ser Thr Ile Val Pro Ala Gly Gly Ser Ala Ile Val Glu Phe Lys Val
        290                 295                 300

Asp Ile Pro Gly Ser Tyr Thr Leu Val Asp His Ser Ile Phe Arg Ala
305                 310                 315                 320

Phe Asn Lys Gly Ala Leu Gly Gln Leu Lys Val Glu
                325                 330
```

<210> SEQ ID NO 86
<211> LENGTH: 332
<212> TYPE: PRT
<213> ORGANISM: Neisseria meningitidis

<400> SEQUENCE: 86

```
Ala Ser Met Phe Ala Leu Ala Ala Cys Gly Gly Glu Pro Ala Ala Gln
1               5                   10                  15

Thr Pro Ala Ala Ser Ala Glu Ala Ala Ser Ser Ala Ala Gln Thr Ala
            20                  25                  30

Ala Glu Thr Pro Ala Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Thr Met Lys Met Asp Asp
65                  70                  75                  80

Gly Val Glu Tyr Arg Tyr Trp Thr Phe Asp Gly Asp Val Pro Gly Arg
                85                  90                  95

Met Ile Arg Val Arg Glu Gly Asp Thr Val Glu Val Glu Phe Ser Asn
            100                 105                 110

Asn Pro Ser Ser Thr Val Pro His Asn Val Asp Phe His Ala Ala Thr
        115                 120                 125

Gly Gln Gly Gly Gly Ala Ala Ala Thr Phe Thr Ala Pro Gly Arg Thr
    130                 135                 140

Ser Thr Phe Ser Phe Lys Ala Leu Gln Pro Gly Leu Tyr Ile Tyr His
145                 150                 155                 160

Cys Ala Val Ala Pro Val Gly Met His Ile Ala Asn Gly Met Tyr Gly
                165                 170                 175

Leu Ile Leu Val Glu Pro Lys Glu Gly Leu Pro Lys Val Asp Lys Glu
            180                 185                 190

Phe Tyr Ile Val Gln Gly Asp Phe Tyr Thr Lys Gly Lys Lys Gly Ala
        195                 200                 205

Gln Gly Leu Gln Pro Phe Asp Met Asp Lys Ala Ile Ala Glu Gln Pro
```

Glu Tyr Val Val Phe Asn Gly His Val Gly Ala Ile Ala Gly Asp Asn
225                 230                 235                 240

Ala Leu Lys Ala Lys Ala Gly Glu Thr Val Arg Met Tyr Val Gly Asn
                245                 250                 255

Gly Gly Pro Asn Leu Val Ser Ser Phe His Val Ile Gly Glu Ile Phe
            260                 265                 270

Asp Lys Val Tyr Val Glu Gly Lys Leu Ile Asn Glu Asn Val Gln
        275                 280                 285

Ser Thr Ile Val Pro Ala Gly Gly Ser Ala Ile Val Glu Phe Lys Val
    290                 295                 300

Asp Ile Pro Gly Ser Tyr Thr Leu Val Asp His Ser Ile Phe Arg Ala
305                 310                 315                 320

Phe Asn Lys Gly Ala Leu Gly Gln Leu Lys Val Glu
                325                 330

<210> SEQ ID NO 87
<211> LENGTH: 332
<212> TYPE: PRT
<213> ORGANISM: Neisseria meningitidis

<400> SEQUENCE: 87

Ala Ser Met Phe Ala Leu Ala Ala Cys Gly Gly Glu Pro Ala Ala Gln
1               5                   10                  15

Thr Pro Ala Ala Ser Ala Glu Ala Ala Ser Ser Ala Ala Gln Thr Ala
                20                  25                  30

Ala Glu Thr Pro Ala Gly Glu Leu Pro Val Ile Asp Ala Val Thr Thr
            35                  40                  45

His Ala Pro Glu Val Pro Pro Ala Ile Asp Arg Asp Tyr Pro Ala Lys
        50                  55                  60

Val Arg Val Lys Met Glu Thr Val Glu Lys Thr Met Lys Met Asp Asp
65                  70                  75                  80

Gly Val Glu Tyr Arg Tyr Trp Thr Phe Asp Gly Asp Val Pro Gly Arg
                85                  90                  95

Met Ile Arg Val Arg Glu Gly Asp Thr Val Glu Val Glu Phe Ser Asn
            100                 105                 110

Asn Pro Ser Ser Thr Val Pro His Asn Val Asp Phe His Ala Ala Thr
        115                 120                 125

Gly Gln Gly Gly Gly Ala Ala Ala Thr Phe Thr Ala Pro Gly Arg Thr
130                 135                 140

Ser Thr Phe Ser Phe Lys Ala Leu Gln Pro Gly Leu Tyr Ile Tyr His
145                 150                 155                 160

Cys Ala Val Ala Pro Val Gly Met His Ile Ala Asn Gly Met Tyr Gly
                165                 170                 175

Leu Ile Leu Val Glu Pro Lys Glu Gly Leu Pro Lys Val Asp Lys Glu
            180                 185                 190

Phe Tyr Ile Val Gln Gly Asp Phe Tyr Thr Lys Gly Lys Lys Gly Ala
        195                 200                 205

Gln Gly Leu Gln Pro Phe Asp Met Asp Lys Ala Ile Ala Glu Gln Pro
210                 215                 220

Glu Tyr Val Val Phe Asn Gly His Val Gly Ala Ile Ala Gly Asp Asn
225                 230                 235                 240

Ala Leu Lys Ala Lys Ala Gly Glu Thr Val Arg Met Tyr Val Gly Asn
                245                 250                 255

-continued

```
Gly Gly Pro Asn Leu Val Ser Ser Phe His Val Ile Gly Glu Ile Phe
            260                 265                 270

Asp Lys Val Tyr Val Glu Gly Gly Lys Leu Ile Asn Glu Asn Val Gln
            275                 280                 285

Ser Thr Ile Val Pro Ala Gly Gly Ser Ala Ile Val Glu Phe Lys Val
            290                 295                 300

Asp Ile Pro Gly Ser Tyr Thr Leu Val Asp His Ser Ile Phe Arg Ala
305                 310                 315                 320

Phe Asn Lys Gly Ala Leu Gly Gln Leu Lys Val Glu
            325                 330

<210> SEQ ID NO 88
<211> LENGTH: 385
<212> TYPE: PRT
<213> ORGANISM: Neisseria meningitidis

<400> SEQUENCE: 88

Met Lys Arg Gln Ala Leu Ala Ala Met Ile Ala Ser Leu Phe Ala Leu
1               5                   10                  15

Ala Ala Cys Gly Gly Glu Pro Ala Ala Gln Pro Ala Ala Ser Ala
            20                  25                  30

Glu Ala Ala Ser Ser Ala Ala Gln Thr Ala Ala Glu Thr Pro Thr Gly
            35                  40                  45

Glu Leu Pro Val Ile Asp Ala Val Thr Thr His Ala Pro Glu Val Pro
        50                  55                  60

Pro Ala Ile Asp Arg Asp Tyr Pro Ala Lys Val Arg Val Lys Met Glu
65                  70                  75                  80

Thr Val Glu Lys Met Thr Met Glu Asp Gly Val Glu Tyr Arg Tyr Trp
                85                  90                  95

Thr Phe Asp Gly Asp Val Pro Gly Arg Met Ile Arg Val Arg Glu Gly
            100                 105                 110

Asp Thr Val Glu Val Glu Phe Ser Asn Asn Pro Ser Ser Thr Val Pro
            115                 120                 125

His Asn Val Asp Phe His Ala Ala Thr Gly Gln Gly Gly Gly Ala Ala
        130                 135                 140

Ala Thr Phe Thr Ala Pro Gly Arg Thr Ser Thr Phe Ser Phe Lys Ala
145                 150                 155                 160

Leu Gln Pro Gly Leu Tyr Ile Tyr His Cys Ala Val Ala Pro Val Gly
                165                 170                 175

Met His Ile Ala Asn Gly Met Tyr Gly Leu Ile Leu Val Glu Pro Lys
            180                 185                 190

Glu Gly Leu Pro Lys Val Asp Lys Glu Phe Tyr Ile Val Gln Gly Asp
            195                 200                 205

Phe Tyr Thr Lys Gly Lys Lys Gly Ala Gln Gly Leu Gln Pro Phe Asp
        210                 215                 220

Met Asp Lys Ala Val Ala Glu Gln Pro Glu Tyr Val Val Phe Asn Gly
225                 230                 235                 240

His Val Gly Ser Ile Ala Gly Asp Asn Ala Leu Lys Ala Lys Ala Gly
                245                 250                 255

Glu Thr Val Arg Met Tyr Val Gly Asn Gly Pro Asn Leu Val Ser
            260                 265                 270

Ser Phe His Val Ile Gly Glu Ile Phe Asp Lys Val Tyr Val Glu Gly
            275                 280                 285

Gly Lys Leu Ile Asn Glu Asn Val Gln Ser Thr Ile Val Pro Ala Gly
        290                 295                 300
```

```
Gly Ser Ala Ile Val Glu Phe Lys Val Asp Ile Pro Gly Ser Tyr Thr
305                 310                 315                 320

Leu Val Asp His Ser Ile Phe Arg Ala Phe Asn Lys Gly Ala Leu Gly
            325                 330                 335

Gln Leu Lys Val Glu Gly Ala Glu Asn Pro Glu Ile Met Thr Gln Lys
        340                 345                 350

Leu Ser Asp Thr Ala Tyr Ala Gly Asn Gly Ala Ala Pro Ala Ala Ser
    355                 360                 365

Ala Pro Ala Ala Ser Ala Pro Ala Ala Ser Ser Glu Lys Ser Val
370                 375                 380

Tyr
385

<210> SEQ ID NO 89
<211> LENGTH: 385
<212> TYPE: PRT
<213> ORGANISM: Neisseria meningitidis

<400> SEQUENCE: 89

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Ala Ser Ala
            20                  25                  30

Glu Ala Ala Ser Ser Ala Ala Gln Thr Ala Ala Glu Thr Pro Thr Gly
        35                  40                  45

Glu Leu Pro Val Ile Asp Ala Val Thr Thr His Ala Pro Glu Val Pro
    50                  55                  60

Pro Ala Ile Asp Arg Asp Tyr Pro Ala Lys Val Arg Val Lys Met Glu
65                  70                  75                  80

Thr Val Glu Lys Met Thr Met Glu Asp Gly Val Glu Tyr Arg Tyr Trp
                85                  90                  95

Thr Phe Asp Gly Asp Val Pro Gly Arg Met Ile Arg Val Arg Glu Gly
            100                 105                 110

Asp Thr Val Glu Val Glu Phe Ser Asn Asn Pro Ser Ser Thr Val Pro
        115                 120                 125

His Asn Val Asp Phe His Ala Ala Thr Gly Gln Gly Gly Gly Ala Ala
    130                 135                 140

Ala Thr Phe Thr Ala Pro Gly Arg Thr Ser Thr Phe Ser Phe Lys Ala
145                 150                 155                 160

Leu Gln Pro Gly Leu Tyr Ile Tyr His Cys Ala Val Ala Pro Val Gly
                165                 170                 175

Met His Ile Ala Asn Gly Met Tyr Gly Leu Ile Leu Val Glu Pro Lys
            180                 185                 190

Glu Gly Leu Pro Lys Val Asp Lys Glu Phe Tyr Ile Val Gln Gly Asp
        195                 200                 205

Phe Tyr Thr Lys Gly Lys Lys Gly Ala Gln Gly Gln Pro Phe Asp
    210                 215                 220

Met Asp Lys Ala Val Ala Glu Gln Pro Glu Tyr Val Val Phe Asn Gly
225                 230                 235                 240

His Val Gly Ala Ile Ala Gly Asp Asn Ala Leu Lys Ala Lys Ala Gly
                245                 250                 255

Glu Thr Val Arg Met Tyr Val Gly Asn Gly Gly Pro Asn Leu Val Ser
            260                 265                 270

Ser Phe His Val Ile Gly Glu Ile Phe Asp Lys Val Tyr Val Glu Gly
```

```
            275                 280                 285
Gly Lys Leu Ile Asn Glu Asn Val Gln Ser Thr Ile Val Pro Ala Gly
    290                 295                 300

Gly Ser Ala Ile Val Glu Phe Lys Val Asp Ile Pro Gly Ser Tyr Thr
305                 310                 315                 320

Leu Val Asp His Ser Ile Phe Arg Ala Phe Asn Lys Gly Ala Leu Gly
                325                 330                 335

Gln Leu Lys Val Glu Gly Ala Glu Asn Pro Glu Ile Met Thr Gln Lys
            340                 345                 350

Leu Ser Asp Thr Ala Tyr Ala Gly Asn Gly Ala Ala Pro Ala Ala Ser
        355                 360                 365

Ala Pro Arg Ala Ser Ala Pro Ala Ser Glu Ser Glu Lys Ser Val
    370                 375                 380

Tyr
385

<210> SEQ ID NO 90
<211> LENGTH: 385
<212> TYPE: PRT
<213> ORGANISM: Neisseria meningitidis

<400> SEQUENCE: 90

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Ala Ser Ala
            20                  25                  30

Glu Ala Ser Ser Ala Ala Gln Thr Ala Ala Glu Thr Pro Thr Gly
        35                  40                  45

Glu Leu Pro Val Ile Asp Ala Val Thr Thr His Ala Pro Glu Val Pro
    50                  55                  60

Pro Ala Ile Asp Arg Asp Tyr Pro Ala Lys Val Arg Val Lys Met Glu
65                  70                  75                  80

Thr Val Glu Lys Met Thr Met Glu Asp Gly Val Glu Tyr Arg Tyr Trp
                85                  90                  95

Thr Phe Asp Gly Asp Val Pro Gly Arg Met Ile Arg Val Arg Glu Gly
            100                 105                 110

Asp Thr Val Glu Val Glu Phe Ser Asn Asn Pro Ser Ser Thr Val Pro
        115                 120                 125

His Asn Val Asp Phe His Ala Ala Thr Gly Gln Gly Gly Ala Ala
    130                 135                 140

Ala Thr Phe Thr Ala Pro Gly Arg Thr Ser Thr Phe Ser Phe Lys Ala
145                 150                 155                 160

Leu Gln Pro Gly Leu Tyr Ile Tyr His Cys Ala Val Ala Pro Val Gly
                165                 170                 175

Met His Ile Ala Asn Gly Met Tyr Gly Leu Ile Leu Val Glu Pro Lys
            180                 185                 190

Glu Gly Leu Pro Lys Val Asp Lys Glu Phe Tyr Ile Val Gln Gly Asp
        195                 200                 205

Phe Tyr Thr Lys Gly Lys Lys Gly Ala Gln Gly Leu Gln Pro Phe Asp
    210                 215                 220

Met Asp Lys Ala Val Ala Glu Gln Pro Glu Tyr Val Val Phe Asn Gly
225                 230                 235                 240

His Val Gly Ser Ile Ala Gly Asp Asn Ala Leu Lys Ala Lys Ala Gly
                245                 250                 255
```

```
Glu Thr Val Arg Met Tyr Val Gly Asn Gly Pro Asn Leu Val Ser
            260                 265                 270

Ser Phe His Val Ile Gly Glu Ile Phe Asp Lys Val Tyr Val Glu Gly
        275                 280                 285

Gly Lys Leu Ile Asn Glu Asn Val Gln Ser Thr Ile Val Pro Ala Gly
    290                 295                 300

Gly Ser Ala Ile Val Glu Phe Lys Val Asp Ile Pro Gly Ser Tyr Thr
305                 310                 315                 320

Leu Val Asp His Ser Ile Phe Arg Ala Phe Asn Lys Gly Ala Leu Gly
                325                 330                 335

Gln Leu Lys Val Glu Gly Ala Glu Asn Pro Glu Ile Met Thr Gln Lys
            340                 345                 350

Leu Ser Asp Thr Ala Tyr Ala Gly Asn Gly Ala Ala Pro Ala Ala Ser
        355                 360                 365

Ala Pro Ala Ala Ser Ala Pro Ala Ala Ser Ser Glu Lys Ser Val
    370                 375                 380

Tyr
385

<210> SEQ ID NO 91
<211> LENGTH: 385
<212> TYPE: PRT
<213> ORGANISM: Neisseria meningitidis

<400> SEQUENCE: 91

Met Lys Arg Gln Ala Leu Ala Ala Met Ile Ala Ser Leu Phe Ala Leu
1               5                   10                  15

Ala Ala Cys Gly Gly Glu Pro Ala Ala Gln Ala Pro Ala Ala Ser Ala
            20                  25                  30

Glu Ala Ala Ser Ser Ala Ala Gln Thr Ala Ala Glu Thr Pro Thr Gly
        35                  40                  45

Glu Leu Pro Val Ile Asp Ala Val Thr Thr His Ala Pro Glu Val Pro
    50                  55                  60

Pro Ala Ile Asp Arg Asp Tyr Pro Ala Lys Val Arg Val Lys Met Glu
65                  70                  75                  80

Thr Val Glu Lys Met Thr Met Glu Asp Gly Val Glu Tyr Arg Tyr Trp
                85                  90                  95

Thr Phe Asp Gly Asp Val Pro Gly Arg Met Ile Arg Val Arg Glu Gly
            100                 105                 110

Asp Thr Val Glu Val Glu Phe Ser Asn Asn Pro Ser Ser Thr Val Pro
        115                 120                 125

His Asn Val Asp Phe His Ala Ala Thr Gly Gln Gly Gly Gly Ala Ala
    130                 135                 140

Ala Thr Phe Thr Ala Pro Gly Arg Thr Ser Thr Phe Ser Phe Lys Ala
145                 150                 155                 160

Leu Gln Pro Gly Leu Tyr Ile Tyr His Cys Ala Val Ala Pro Val Gly
                165                 170                 175

Met His Ile Ala Asn Gly Met Tyr Gly Leu Ile Leu Val Glu Pro Lys
            180                 185                 190

Glu Gly Leu Pro Lys Val Asp Lys Glu Ser Tyr Ile Val Gln Gly Asp
        195                 200                 205

Phe Tyr Thr Lys Gly Lys Lys Gly Ala Gln Gly Leu Gln Pro Phe Asp
    210                 215                 220

Met Asp Lys Ala Val Ala Glu Gln Pro Glu Tyr Val Val Phe Asn Gly
225                 230                 235                 240
```

```
His Val Gly Ala Ile Ala Gly Asp Asn Ala Leu Lys Ala Lys Ala Gly
                245                 250                 255

Glu Thr Val Arg Met Tyr Val Gly Asn Gly Pro Asn Leu Val Ser
            260                 265                 270

Ser Phe His Val Ile Gly Glu Ile Phe Asp Lys Val Tyr Val Glu Gly
        275                 280                 285

Gly Lys Leu Ile Asn Glu Asn Val Gln Ser Thr Ile Val Pro Ala Gly
        290                 295                 300

Gly Ser Ala Ile Val Glu Phe Lys Val Asp Ile Pro Gly Ser Tyr Thr
305                 310                 315                 320

Leu Val Asp His Ser Ile Phe Arg Ala Phe Asn Lys Gly Ala Leu Gly
                325                 330                 335

Gln Leu Lys Val Glu Gly Ala Glu Asn Pro Glu Ile Met Thr Gln Lys
            340                 345                 350

Leu Ser Asp Thr Ala Tyr Ala Gly Asn Gly Ala Ala Pro Ala Ala Ser
        355                 360                 365

Ala Pro Ala Ala Ser Ala Pro Ala Ala Ser Ala Ser Glu Lys Ser Val
    370                 375                 380

Tyr
385

<210> SEQ ID NO 92
<211> LENGTH: 331
<212> TYPE: PRT
<213> ORGANISM: Neisseria meningitidis

<400> SEQUENCE: 92

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
    50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Glu Phe Ser Asn Asn
            100                 105                 110

Pro Ser Ser Thr Val Pro His Asn Val Asp Phe His Ala Ala Thr Gly
        115                 120                 125

Gln Gly Gly Gly Ala Ala Ala Thr Phe Thr Ala Pro Gly Arg Thr Ser
    130                 135                 140

Thr Phe Ser Leu Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Leu Pro Lys Val Asp Lys Glu Ser
            180                 185                 190

Tyr Ile Val Gln Gly Asp Phe Tyr Thr Lys Gly Lys Lys Gly Ala Gln
        195                 200                 205

Gly Leu Gln Pro Phe Asp Met Asp Lys Ala Val Ala Glu Gln Pro Glu
```

```
            210                 215                 220
Tyr Val Val Phe Asn Gly His Val Gly Ala Ile Ala Gly Asp Asn Ala
225                 230                 235                 240

Leu Lys Ala Lys Ala Gly Glu Thr Val Arg Met Tyr Val Gly Asn Gly
                245                 250                 255

Gly Pro Asn Leu Val Ser Ser Phe His Val Ile Gly Glu Ile Phe Asp
                    260                 265                 270

Lys Val Tyr Val Glu Gly Gly Lys Leu Ile Asn Glu Asn Val Gln Ser
                275                 280                 285

Thr Ile Val Pro Ala Gly Gly Ser Ala Ile Val Glu Phe Lys Val Asp
            290                 295                 300

Ile Pro Gly Ser Tyr Thr Leu Val Asp His Ser Ile Phe Arg Ala Asn
305                 310                 315                 320

Phe Lys Gly Ala Leu Gly Gln Leu Lys Val Glu
                325                 330

<210> SEQ ID NO 93
<211> LENGTH: 331
<212> TYPE: PRT
<213> ORGANISM: Neisseria meningitidis

<400> SEQUENCE: 93

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
                20                  25                  30

Ala Glu Thr Pro Thr Gly Glu Leu Pro Val Ile Asp Ala Val Thr Thr
            35                  40                  45

His Ala Pro Glu Val Pro Pro Ala Ile Asp Arg Asp Tyr Pro Ala Lys
50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Glu Phe Ser Asn Asn
                    100                 105                 110

Pro Ser Ser Thr Val Pro His Asn Val Asp Phe His Ala Ala Thr Gly
                115                 120                 125

Gln Gly Gly Gly Ala Ala Ala Thr Phe Thr Ala Pro Gly Arg Thr Ser
130                 135                 140

Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Leu Pro Lys Val Asp Lys Glu Ser
                    180                 185                 190

Tyr Ile Val Gln Gly Asp Phe Tyr Thr Lys Gly Lys Lys Gly Ala Gln
                195                 200                 205

Gly Leu Gln Pro Phe Asp Met Asp Lys Ala Val Ala Glu Gln Pro Glu
            210                 215                 220

Tyr Val Val Phe Asn Gly His Val Gly Ala Ile Ala Gly Asp Asn Ala
225                 230                 235                 240

Leu Lys Ala Lys Ala Gly Glu Thr Val Arg Met Tyr Val Gly Asn Gly
                245                 250                 255
```

```
Gly Pro Asn Leu Val Ser Ser Phe His Val Ile Gly Glu Ile Phe Asp
                260                 265                 270

Lys Val Tyr Val Glu Gly Gly Lys Leu Ile Asn Glu Asn Val Gln Ser
            275                 280                 285

Thr Ile Val Pro Ala Gly Gly Ser Ala Ile Val Glu Phe Lys Val Asp
        290                 295                 300

Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
                325                 330

<210> SEQ ID NO 94
<211> LENGTH: 331
<212> TYPE: PRT
<213> ORGANISM: Neisseria meningitidis

<400> SEQUENCE: 94

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
            20                  25                  30

Ala Glu Thr Pro Thr Gly Glu Leu Pro Val Ile Asp Ala Val Thr Thr
        35                  40                  45

His Ala Pro Glu Val Pro Pro Ala Ile Asp Arg Asp Tyr Pro Ala Lys
50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Glu Phe Ser Asn Asn
            100                 105                 110

Pro Ser Ser Thr Val Pro His Asn Val Asp Phe His Ala Ala Thr Gly
        115                 120                 125

Gln Gly Gly Gly Ala Ala Ala Thr Phe Thr Ala Pro Gly Arg Thr Ser
    130                 135                 140

Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Leu Pro Lys Val Asp Lys Glu Phe
            180                 185                 190

Tyr Ile Val Gln Gly Asp Phe Tyr Thr Lys Gly Lys Lys Gly Ala Gln
        195                 200                 205

Gly Pro Gln Pro Phe Asp Met Asp Lys Ala Val Ala Glu Gln Pro Glu
    210                 215                 220

Tyr Val Val Phe Asn Gly His Val Gly Ala Ile Ala Gly Asp Asn Ala
225                 230                 235                 240

Leu Lys Ala Lys Ala Gly Glu Thr Val Arg Met Tyr Val Gly Asn Gly
                245                 250                 255

Gly Pro Asn Leu Val Ser Ser Phe His Val Ile Gly Glu Ile Phe Asp
            260                 265                 270

Lys Val Tyr Val Glu Gly Gly Lys Leu Ile Asn Glu Asn Val Gln Ser
        275                 280                 285

Thr Ile Val Pro Ala Gly Gly Ser Ala Ile Val Glu Phe Lys Val Asp
    290                 295                 300
```

```
Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
                325                 330

<210> SEQ ID NO 95
<211> LENGTH: 331
<212> TYPE: PRT
<213> ORGANISM: Neisseria meningitidis

<400> SEQUENCE: 95

Ala Ser Leu Phe Ala Leu Ala Ala Cys Gly Gly Glu Pro Ala Ala Gln
1               5                   10                  15

Ala Pro Ala Ala Ser Ala Glu Ala Ala Ser Ser Ala Ala Gln Thr Ala
                20                  25                  30

Ala Glu Thr Pro Thr Gly Glu Leu Pro Val Ile Asp Ala Val Thr Thr
            35                  40                  45

His Ala Pro Glu Val Pro Ala Ile Asp Arg Asp Tyr Pro Ala Lys
        50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Glu Phe Ser Asn Asn
                100                 105                 110

Pro Ser Ser Thr Val Pro His Asn Val Asp Phe His Ala Ala Thr Gly
            115                 120                 125

Gln Gly Gly Gly Ala Ala Ala Thr Phe Thr Ala Pro Gly Arg Thr Ser
    130                 135                 140

Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Leu Pro Lys Val Asp Lys Glu Ser
            180                 185                 190

Tyr Ile Val Gln Gly Asp Phe Tyr Thr Lys Gly Lys Lys Gly Ala Gln
        195                 200                 205

Gly Leu Gln Pro Phe Asp Met Asp Lys Ala Val Ala Glu Gln Pro Glu
    210                 215                 220

Tyr Val Val Phe Asn Gly His Val Gly Ala Ile Ala Gly Asp Asn Ala
225                 230                 235                 240

Leu Lys Ala Lys Ala Gly Glu Thr Val Arg Met Tyr Val Gly Asn Gly
                245                 250                 255

Gly Pro Asn Leu Val Ser Ser Phe His Val Ile Gly Glu Ile Phe Asp
            260                 265                 270

Lys Val Tyr Val Glu Gly Gly Lys Leu Ile Asn Glu Asn Val Gln Ser
        275                 280                 285

Thr Ile Val Pro Ala Gly Gly Ser Ala Ile Val Glu Phe Lys Val Asp
    290                 295                 300

Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
                325                 330
```

<210> SEQ ID NO 96
<211> LENGTH: 331
<212> TYPE: PRT
<213> ORGANISM: Neisseria meningitidis

<400> SEQUENCE: 96

| Ala | Ser | Leu | Phe | Ala | Leu | Ala | Ala | Cys | Gly | Gly | Glu | Pro | Ala | Ala | Gln |
|---|---|---|---|---|---|---|---|---|---|---|---|---|---|---|---|
| 1 | | | | 5 | | | | | 10 | | | | | 15 | |

| Ala | Pro | Ala | Ala | Ser | Ala | Glu | Ala | Ala | Ser | Ser | Ala | Ala | Gln | Thr | Ala |
| | | | 20 | | | | | 25 | | | | | 30 | | |

| Ala | Glu | Thr | Pro | Thr | Gly | Glu | Leu | Pro | Val | Ile | Asp | Ala | Val | Thr | Thr |
| | | 35 | | | | | 40 | | | | | 45 | | | |

| His | Ala | Pro | Glu | Val | Pro | Ala | Ile | Asp | Arg | Asp | Tyr | Pro | Ala | Lys |
| | 50 | | | | | 55 | | | | | 60 | | | | |

| Val | Arg | Val | Lys | Met | Glu | Thr | Val | Glu | Lys | Met | Thr | Met | Glu | Asp | Gly |
| 65 | | | | | 70 | | | | | 75 | | | | | 80 |

| Val | Glu | Tyr | Arg | Tyr | Trp | Thr | Phe | Asp | Gly | Asp | Val | Pro | Gly | Arg | Met |
| | | | | 85 | | | | | 90 | | | | | 95 | |

| Ile | Arg | Val | Arg | Glu | Gly | Asp | Thr | Val | Glu | Val | Glu | Phe | Ser | Asn | Asn |
| | | | 100 | | | | | 105 | | | | | 110 | | |

| Pro | Ser | Ser | Thr | Val | Pro | His | Asn | Val | Asp | Phe | His | Ala | Ala | Thr | Gly |
| | | 115 | | | | | 120 | | | | | 125 | | | |

| Gln | Gly | Gly | Gly | Ala | Ala | Thr | Phe | Thr | Ala | Pro | Gly | Arg | Thr | Ser |
| | 130 | | | | | 135 | | | | | 140 | | | | |

| Thr | Phe | Ser | Phe | Lys | Ala | Leu | Gln | Pro | Gly | Leu | Tyr | Ile | Tyr | His | Cys |
| 145 | | | | | 150 | | | | | 155 | | | | | 160 |

| Ala | Val | Ala | Pro | Val | Gly | Met | His | Ile | Ala | Asn | Gly | Met | Tyr | Gly | Leu |
| | | | | 165 | | | | | 170 | | | | | 175 | |

| Ile | Leu | Val | Glu | Pro | Lys | Glu | Gly | Leu | Pro | Lys | Val | Asp | Lys | Glu | Ser |
| | | | 180 | | | | | 185 | | | | | 190 | | |

| Tyr | Ile | Val | Gln | Gly | Asp | Phe | Tyr | Thr | Lys | Gly | Lys | Lys | Gly | Ala | Gln |
| | | 195 | | | | | 200 | | | | | 205 | | | |

| Gly | Leu | Gln | Pro | Phe | Asp | Met | Asp | Lys | Ala | Val | Ala | Glu | Gln | Pro | Glu |
| | 210 | | | | | 215 | | | | | 220 | | | | |

| Tyr | Val | Val | Phe | Asn | Gly | His | Val | Gly | Ala | Ile | Ala | Gly | Asp | Asn | Ala |
| 225 | | | | | 230 | | | | | 235 | | | | | 240 |

| Leu | Lys | Ala | Lys | Ala | Gly | Glu | Thr | Val | Arg | Met | Tyr | Val | Gly | Asn | Gly |
| | | | | 245 | | | | | 250 | | | | | 255 | |

| Gly | Pro | Asn | Leu | Val | Ser | Ser | Phe | His | Val | Ile | Gly | Glu | Ile | Phe | Asp |
| | | | 260 | | | | | 265 | | | | | 270 | | |

| Lys | Val | Tyr | Val | Glu | Gly | Gly | Lys | Leu | Ile | Asn | Glu | Asn | Val | Gln | Ser |
| | | 275 | | | | | 280 | | | | | 285 | | | |

| Thr | Ile | Val | Pro | Ala | Gly | Gly | Ser | Ala | Ile | Val | Glu | Phe | Lys | Val | Asp |
| | 290 | | | | | 295 | | | | | 300 | | | | |

| Ile | Pro | Gly | Ser | Tyr | Thr | Leu | Val | Asp | His | Ser | Ile | Phe | Arg | Ala | Phe |
| 305 | | | | | 310 | | | | | 315 | | | | | 320 |

| Asn | Lys | Gly | Ala | Leu | Gly | Gln | Leu | Lys | Val | Glu |
| | | | | 325 | | | | | 330 | |

<210> SEQ ID NO 97
<211> LENGTH: 331
<212> TYPE: PRT
<213> ORGANISM: Neisseria meningitidis

<400> SEQUENCE: 97

Ala Ser Leu Phe Ala Leu Ala Ala Cys Gly Gly Glu Pro Ala Ala Gln

```
            1               5                  10                 15
          Ala Pro Ala Ala Ser Ala Glu Ala Ala Ser Ser Ala Ala Gln Thr Ala
                          20                 25                 30
          Ala Glu Thr Pro Thr Gly Glu Leu Pro Val Ile Asp Ala Val Thr Thr
                          35                 40                 45
          His Ala Pro Glu Val Pro Ala Ile Asp Arg Asp Tyr Pro Ala Lys
                          50              55                 60
          Val Arg Val Lys Met Glu Thr Val Glu Lys Met Thr Met Glu Asp Gly
           65                 70                 75                 80
          Val Glu Tyr Arg Tyr Trp Thr Phe Asp Gly Asp Val Pro Gly Arg Met
                              85                 90                 95
          Ile Arg Val Arg Glu Gly Asp Thr Val Glu Val Glu Phe Ser Asn Asn
                          100                105                110
          Pro Ser Ser Thr Val Pro His Asn Val Asp Phe His Ala Ala Thr Gly
                          115                120                125
          Gln Gly Gly Gly Ala Ala Thr Phe Thr Ala Pro Gly Arg Thr Ser
                      130                135                140
          Thr Phe Ser Phe Lys Ala Leu Gln Pro Gly Leu Tyr Ile Tyr His Cys
          145                150                155                160
          Ala Val Ala Pro Val Gly Met His Ile Ala Asn Gly Met Tyr Gly Leu
                              165                170                175
          Ile Leu Val Glu Pro Lys Glu Gly Leu Pro Lys Val Asp Lys Glu Ser
                          180                185                190
          Tyr Ile Val Gln Gly Asp Phe Tyr Thr Lys Gly Lys Lys Gly Ala Gln
                          195                200                205
          Gly Leu Gln Pro Phe Asp Met Asp Lys Ala Val Ala Glu Gln Pro Glu
                      210                215                220
          Tyr Val Val Phe Asn Gly His Val Gly Ala Ile Ala Gly Asp Asn Ala
          225                230                235                240
          Leu Lys Ala Lys Ala Gly Glu Thr Val Arg Met Tyr Val Gly Asn Gly
                              245                250                255
          Gly Pro Asn Leu Val Ser Ser Phe His Val Ile Gly Glu Ile Phe Asp
                          260                265                270
          Lys Val Tyr Val Glu Gly Gly Lys Leu Ile Asn Glu Asn Val Gln Ser
                          275                280                285
          Thr Ile Val Pro Ala Gly Gly Ser Ala Ile Val Glu Phe Lys Val Asp
                      290                295                300
          Ile Pro Gly Ser Tyr Thr Leu Val Asp His Ser Ile Phe Arg Ala Phe
          305                310                315                320
          Asn Lys Gly Ala Leu Gly Gln Leu Lys Val Glu
                              325                330
```

<210> SEQ ID NO 98
<211> LENGTH: 331
<212> TYPE: PRT
<213> ORGANISM: Neisseria meningitidis

<400> SEQUENCE: 98

```
          Ala Ser Leu Phe Ala Leu Ala Ala Cys Gly Gly Glu Pro Ala Ala Gln
           1               5                  10                 15
          Ala Pro Ala Ala Ser Ala Glu Ala Ala Ser Ser Ala Ala Gln Thr Ala
                          20                 25                 30
          Ala Glu Thr Pro Thr Gly Glu Leu Pro Val Ile Asp Ala Val Thr Thr
                          35                 40                 45
```

-continued

```
His Ala Pro Glu Val Pro Ala Ile Asp Arg Asp Tyr Pro Ala Lys
    50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Phe Ser Asn Asn
                100                 105                 110

Pro Ser Ser Thr Val Pro His Asn Val Asp Phe His Ala Ala Thr Gly
                115                 120                 125

Gln Gly Gly Ala Ala Thr Phe Thr Ala Pro Gly Arg Thr Ser
    130                 135                 140

Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Leu Pro Lys Val Asp Lys Glu Phe
                180                 185                 190

Tyr Ile Val Gln Gly Asp Phe Tyr Thr Lys Gly Lys Lys Gly Ala Gln
                195                 200                 205

Gly Leu Gln Pro Phe Asp Met Asp Lys Ala Val Ala Glu Gln Pro Glu
    210                 215                 220

Tyr Val Val Phe Asn Gly His Val Gly Ser Ile Ala Gly Asp Asn Ala
225                 230                 235                 240

Leu Lys Ala Lys Ala Gly Glu Thr Val Arg Met Tyr Val Gly Asn Gly
                245                 250                 255

Gly Pro Asn Leu Val Ser Ser Phe His Val Ile Gly Glu Ile Phe Asp
                260                 265                 270

Lys Val Tyr Val Glu Gly Gly Lys Leu Ile Asn Glu Asn Val Gln Ser
                275                 280                 285

Thr Ile Val Pro Ala Gly Gly Ser Ala Ile Val Glu Phe Lys Val Asp
    290                 295                 300

Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
                325                 330
```

<210> SEQ ID NO 99
<211> LENGTH: 331
<212> TYPE: PRT
<213> ORGANISM: Neisseria meningitidis

<400> SEQUENCE: 99

```
Ala Ser Leu Phe Ala Leu Ala Ala Cys Gly Gly Glu Pro Ala Ala Gln
1               5                   10                  15

Ala Pro Ala Ala Ser Ala Glu Ala Ser Ser Ala Ala Gln Thr Ala
            20                  25                  30

Ala Glu Thr Pro Thr Gly Glu Leu Pro Val Ile Asp Ala Val Thr Thr
            35                  40                  45

His Ala Pro Glu Val Pro Ala Ile Asp Arg Asp Tyr Pro Ala Lys
    50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95
```

```
Ile Arg Val Arg Glu Gly Asp Thr Val Glu Val Glu Phe Ser Asn Asn
                100                 105                 110

Pro Ser Ser Thr Val Pro His Asn Val Asp Phe His Ala Ala Thr Gly
            115                 120                 125

Gln Gly Gly Gly Ala Ala Ala Thr Phe Thr Ala Pro Gly Arg Thr Ser
        130                 135                 140

Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Pro Lys Val Asp Lys Glu Phe
            180                 185                 190

Tyr Ile Val Gln Gly Asp Phe Tyr Thr Lys Gly Lys Lys Gly Ala Gln
        195                 200                 205

Gly Leu Gln Pro Phe Asp Met Asp Lys Ala Val Ala Glu Gln Pro Glu
    210                 215                 220

Tyr Val Val Phe Asn Gly His Val Gly Ser Ile Ala Gly Asp Asn Ala
225                 230                 235                 240

Leu Lys Glu Lys Ala Gly Glu Thr Val Arg Met Tyr Val Gly Asn Gly
                245                 250                 255

Gly Pro Asn Leu Val Ser Ser Phe His Val Ile Gly Glu Ile Phe Asp
            260                 265                 270

Lys Val Tyr Val Glu Gly Gly Lys Leu Ile Asn Glu Asn Val Gln Ser
        275                 280                 285

Thr Ile Val Pro Ala Gly Gly Ser Ala Ile Val Glu Phe Lys Val Asp
    290                 295                 300

Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
                325                 330

<210> SEQ ID NO 100
<211> LENGTH: 331
<212> TYPE: PRT
<213> ORGANISM: Neisseria meningitidis

<400> SEQUENCE: 100

Ala Ser Leu Phe Ala Leu Ala Ala Cys Gly Gly Glu Pro Pro Ala Gln
1               5                   10                  15

Ala Pro Ala Ala Ser Ala Glu Ala Ser Ser Ala Ala Gln Thr Ala
            20                  25                  30

Ala Glu Thr Pro Thr Gly Glu Leu Pro Val Ile Asp Ala Val Thr Thr
            35                  40                  45

His Ala Pro Glu Val Pro Pro Ala Ile Asp Arg Asp Tyr Pro Ala Lys
        50                  55                  60

Val Arg Val Lys Met Glu Thr Val Glu Lys Met Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Glu Phe Ser Asn Asn
                100                 105                 110

Pro Ser Ser Thr Val Pro His Asn Val Asp Phe His Ala Ala Thr Gly
            115                 120                 125

Gln Gly Gly Gly Ala Ala Ala Thr Phe Thr Ala Pro Gly Arg Thr Ser
```

```
                      130                 135                 140
Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175

Ile Leu Val Glu Pro Lys Glu Gly Leu Pro Lys Val Asp Lys Glu Ser
                180                 185                 190

Tyr Ile Val Gln Gly Asp Phe Tyr Thr Lys Gly Lys Lys Gly Ala Gln
                195                 200                 205

Gly Leu Gln Pro Phe Asp Met Asp Lys Ala Val Ala Glu Gln Pro Glu
            210                 215                 220

Tyr Val Val Phe Asn Gly His Val Gly Ala Ile Ala Gly Asp Asn Ala
225                 230                 235                 240

Leu Lys Ala Lys Ala Gly Glu Thr Val Arg Met Tyr Val Gly Asn Gly
                245                 250                 255

Gly Pro Asn Leu Val Ser Ser Phe His Val Ile Gly Glu Ile Phe Asp
                260                 265                 270

Lys Val Tyr Val Glu Gly Gly Lys Leu Ile Asn Glu Asn Val Gln Ser
                275                 280                 285

Thr Ile Val Pro Ala Gly Gly Ser Ala Ile Val Glu Phe Lys Val Asp
            290                 295                 300

Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
                325                 330

<210> SEQ ID NO 101
<211> LENGTH: 331
<212> TYPE: PRT
<213> ORGANISM: Neisseria meningitidis

<400> SEQUENCE: 101

Ala Ser Leu Phe Ala Leu Ala Ala Cys Gly Gly Glu Pro Ala Ala Gln
1               5                   10                  15

Ala Pro Ala Ala Ser Ala Glu Ala Ser Ser Ala Ala Gln Thr Ala
                20                  25                  30

Ala Glu Thr Pro Thr Gly Glu Leu Pro Val Ile Asp Ala Val Thr Thr
            35                  40                  45

His Ala Pro Glu Val Pro Pro Ala Ile Asp Arg Asp Tyr Pro Ala Lys
        50                  55                  60

Val Arg Val Lys Met Glu Thr Val Glu Lys Lys Thr Met Glu Asp Gly
65                  70                  75                  80

Val Glu Tyr Arg Tyr Trp Thr Phe Asp Gly Asp Val Pro Gly Arg Met
                85                  90                  95

Ile Arg Val Arg Glu Gly Asp Thr Val Glu Val Glu Phe Ser Asn Asn
                100                 105                 110

Pro Ser Ser Thr Val Pro His Asn Val Asp Phe His Ala Ala Thr Gly
            115                 120                 125

Gln Gly Gly Gly Ala Ala Thr Phe Thr Ala Pro Gly Arg Thr Ser
        130                 135                 140

Thr Phe Ser Phe Lys Ala Leu Gln Pro Gly Leu Tyr Ile Tyr His Cys
145                 150                 155                 160

Ala Val Ala Pro Val Gly Met His Ile Ala Asn Gly Met Tyr Gly Leu
                165                 170                 175
```

```
Ile Leu Val Glu Pro Lys Glu Gly Leu Pro Lys Val Asp Lys Glu Ser
            180                 185                 190

Tyr Ile Val Gln Gly Asp Phe Tyr Thr Lys Gly Lys Lys Gly Ala Gln
            195                 200                 205

Gly Leu Gln Pro Phe Asp Met Asp Lys Ala Val Ala Glu Gln Pro Glu
            210                 215                 220

Tyr Val Val Phe Asn Gly His Val Gly Ala Ile Ala Gly Asp Asn Ala
225                 230                 235                 240

Leu Lys Ala Lys Ala Gly Glu Thr Val Arg Met Tyr Val Gly Asn Gly
            245                 250                 255

Gly Pro Asn Leu Val Ser Ser Phe His Val Ile Gly Glu Ile Phe Asp
            260                 265                 270

Lys Val Tyr Val Glu Gly Gly Lys Leu Ile Asn Glu Asn Val Gln Ser
            275                 280                 285

Thr Ile Val Pro Ala Gly Gly Ser Ala Ile Val Glu Phe Lys Val Asp
            290                 295                 300

Ile Pro Gly Ser Tyr Thr Leu Val Asp His Ser Ile Phe Arg Ala Phe
305                 310                 315                 320

Asn Lys Gly Ala Leu Gly Gln Leu Lys Val Glu
            325                 330

<210> SEQ ID NO 102
<211> LENGTH: 337
<212> TYPE: PRT
<213> ORGANISM: Neisseria meningitidis

<400> SEQUENCE: 102

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
            35                  40                  45

Asp Ala Ile Val Thr His Ala Pro Glu Val Pro Pro Thr Asp Arg
50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
            85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
            115                 120                 125

Phe His Ala Ala Thr Gly Gln Gly Gly Ala Ala Thr Phe Thr
            130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
            165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
            195                 200                 205

Gly Lys Lys Gly Ala Gln Gly Leu Gln Pro Phe Asp Met Asp Lys Ala
            210                 215                 220
```

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
            245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
            275                 280                 285

Asn Glu Asn Val Gln Ser Thr Ile Val Pro Ala Gly Gly Ser Ala Ile
            290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 103
<211> LENGTH: 337
<212> TYPE: PRT
<213> ORGANISM: Neisseria meningitidis

<400> SEQUENCE: 103

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

```
Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
            275                 280                 285

Asn Glu Asn Val Gln Ser Thr Ile Val Pro Ala Gly Gly Ser Ala Ile
            290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 104
<211> LENGTH: 337
<212> TYPE: PRT
<213> ORGANISM: Neisseria meningitidis

<400> SEQUENCE: 104

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285
```

```
Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 105
<211> LENGTH: 337
<212> TYPE: PRT
<213> ORGANISM: Neisseria meningitidis

<400> SEQUENCE: 105

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
                20                  25                  30

Asn Ser Gln Ala Ala Ala Glu Thr Pro Ser Ser Glu Leu Pro Val Ile
            35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
                100                 105                 110

Val Glu Phe Ser Asn Asn Pro Ser Ser Thr Val Pro His Asn Val Asp
            115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
                180                 185                 190

Lys Val Asp Lys Glu Phe Tyr Ile Val Gln Gly Asp Phe Tyr Thr Lys
            195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
                260                 265                 270

Ile Gly Glu Ile Phe Asp Lys Val Tyr Val Gly Gly Lys Leu Ile
            275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320
```

Ser Ile Phe Arg Ala Phe Asn Lys Gly Ala Leu Gly Gln Leu Lys Val
            325                 330                 335

Glu

<210> SEQ ID NO 106
<211> LENGTH: 337
<212> TYPE: PRT
<213> ORGANISM: Neisseria meningitidis

<400> SEQUENCE: 106

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 107
<211> LENGTH: 337
<212> TYPE: PRT
<213> ORGANISM: Neisseria meningitidis

<400> SEQUENCE: 107

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 108
<211> LENGTH: 337
<212> TYPE: PRT
<213> ORGANISM: Neisseria meningitidis

<400> SEQUENCE: 108

```
Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu
```

<210> SEQ ID NO 109
<211> LENGTH: 337
<212> TYPE: PRT
<213> ORGANISM: Neisseria meningitidis

<400> SEQUENCE: 109

```
Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu
```

<210> SEQ ID NO 110
<211> LENGTH: 337
<212> TYPE: PRT
<213> ORGANISM: Neisseria meningitidis

```
<400> SEQUENCE: 110

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
            115                 120                 125

Phe His Ala Ala Thr Gly Gln Gly Gly Ala Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
            195                 200                 205

Gly Lys Lys Gly Ala Gln Gly Leu Gln Pro Phe Asp Met Asp Lys Ala
        210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
        290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 111
<211> LENGTH: 337
<212> TYPE: PRT
<213> ORGANISM: Neisseria meningitidis
```

<400> SEQUENCE: 111

```
Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Ala Thr Phe Thr
130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu
```

<210> SEQ ID NO 112
<211> LENGTH: 337
<212> TYPE: PRT
<213> ORGANISM: Neisseria me -continued

```
<400> SEQUENCE: 112

Ala Ser Val Phe Ala Leu Ala Ala Cys Gly Glu Gln Ala Ala Lys Pro
1               5                   10                  15

Ala Glu Thr Pro Ala Ala Thr Ala Ser Ala Glu Ala Pro Ala Ala Ser
            20                  25                  30

Asn Ser Gln Ala Ala Ala Glu Thr Pro Ser Ser Glu Leu Pro Val Ile
        35                  40                  45

Asp Ala Ile Val Thr His Ala Pro Glu Val Pro Pro Thr Asp Arg
    50                  55                  60

Asp His Pro Ala Lys Val Arg Val Lys Met Glu Thr Val Glu Lys Thr
65                  70                  75                  80

Met Lys Met Asp Asp Gly Val Glu Tyr His Tyr Trp Thr Phe Asp Gly
                85                  90                  95

Asp Val Pro Gly Arg Met Ile Arg Val Arg Glu Gly Asp Thr Val Glu
            100                 105                 110

Val Glu Phe Ser Asn Asn Pro Ser Ser Thr Val Pro His Asn Val Asp
        115                 120                 125

Phe His Ala Ala Thr Gly Gln Gly Gly Ala Ala Thr Phe Thr
    130                 135                 140

Ala Pro Gly Arg Thr Ser Thr Phe Ser Phe Lys Ala Leu Gln Ala Gly
145                 150                 155                 160

Leu Tyr Ile Tyr His Cys Ala Val Ala Pro Val Gly Met His Ile Ala
                165                 170                 175

Asn Gly Met Tyr Gly Leu Ile Leu Val Glu Pro Lys Glu Gly Leu Pro
            180                 185                 190

Lys Val Asp Lys Glu Phe Tyr Ile Val Gln Gly Asp Phe Tyr Thr Lys
        195                 200                 205

Gly Lys Lys Gly Ala Gln Gly Leu Gln Pro Phe Asp Met Asp Lys Ala
    210                 215                 220

Ile Ala Glu Gln Pro Glu Tyr Val Val Phe Asn Gly His Val Gly Ser
225                 230                 235                 240

Ile Ala Gly Asp Asn Ala Leu Lys Ala Lys Ala Gly Glu Thr Ile Arg
                245                 250                 255

Met Tyr Val Gly Asn Gly Gly Pro Asn Leu Val Ser Ser Phe His Val
            260                 265                 270

Ile Gly Glu Ile Phe Asp Lys Val Tyr Val Glu Gly Gly Lys Leu Ile
        275                 280                 285

Asn Glu Asn Val Gln Ser Thr Ile Val Pro Ala Gly Gly Ser Ala Ile
    290                 295                 300

Val Glu Phe Lys Val Asp Ile Pro Gly Ser Tyr Thr Leu Val Asp His
305                 310                 315                 320

Ser Ile Phe Arg Ala Phe Asn Lys Gly Ala Leu Gly Gln Leu Lys Val
                325                 330                 335

Glu

<210> SEQ ID NO 113
<211> LENGTH: 4
<212> TYPE: PRT
<213> ORGANISM: Artificial Sequence
```

```
<220> FEATURE:
<223> OTHER INFORMATION: Carboxy-terminal serine-containing tetrapeptide
      repeat

<400> SEQUENCE: 113

Ala Ala Ser Ala
1
```

MUTANT BACTERIAL GLYCOPROTEINS AND USES THEREOF

CROSS REFERENCE TO RELATED APPLICATIONS

This is the U.S. National Stage of International Application No. PCT/AU2009/001111, filed Aug. 28, 2009 which was published in English under PCT Article 21(2), which in turn claims the benefit of Australia Patent Application No. 2008904429, filed Aug. 28, 2008, and which is incorporated herein by reference in its entirety.

FIELD OF THE INVENTION

THIS INVENTION relates to mutant glycoproteins of pathogenic bacteria, such as *Neisseria*, lacking one or more post-translational modifications and their use in immunotherapy and/or vaccines.

BACKGROUND OF THE INVENTION

Disease caused by Group B *Neisseria meningitidis* (*N. meningitidis*) remains a significant health problem worldwide. There are currently no effective vaccines available for this Group, although effective treatment for meningococcal infections is available with antibiotics. However, the progression of the infection can be so rapid that in some cases treatment cannot be administered in time to be effective. The threat of meningococcal disease would be most appropriately dealt with by prevention with a generally effective vaccine. There is also no vaccine to prevent infection by the related pathogen *Neisseria gonorrhoea* (*N. gonorrhoeae*). Although effective treatment of gonococcal infections is currently available with antibiotics, resistance is increasing. Furthermore, in gonococcal infections, asymptomatic carriage (particularly common in women) can result in greater susceptibility to HIV, and may also lead to pelvic inflammatory disease.

Pili of pathogenic *Neisseria* are typical of a family of adhesins, type IV fimbriae, found in a wide range of Gram-negative pathogens. These long polymeric proteins protrude from the bacterial surface and have a crucial role in both colonization of the host and adhesion to host cells (Virji et al., 1991; McGee & Stephens, 1984). Although there are other accessory proteins, pili are composed primarily of thousands of subunits, called pilin. Pili of pathogenic *Neisseria* are major virulence factors associated with adhesion, cytotoxicity, twitching motility, auto-aggregation and DNA transformation.

Typical of many surface proteins of pathogenic *Neisseria*, pili display both phase and antigenic variation (reviewed in Seifert, 1996) and are post-translationally modified (reviewed in Virji, 1997). Four different types of modifications have been described. A phosphodiester-linked glycerol substituent has been reported at serine 93 of the pilin molecule (Stimson et al., 1996), a phosphate group has been reported at serine 68 in *N. gonorrhoeae* (Forest et al., 1999), pili of both *N. meningitidis* and *N. gonorrhoeae* are glycosylated at serine 623 with a trisaccharide molecule, Gal (β1-4) Gal (α1-3) 2,4-diacetimido-2,4,6-trideoxyhexose (Stimson et al., 1995) or a disaccharide Gal (α1-3) GlcNAc (Parge et al., 1995; Marceau et al., 1998). Covalently linked phosphorylcholine (ChoP) has been reported in *N. meningitidis* and *N. gonorrhoeae* (Kolberg et al., 1997; Weiser et al., 1998) and is found on surface-exposed moieties of many different pathogens of the respiratory tract (Gillespie et al., 1996 J Med Microbiol 44:35-40). In *H. influenzae*, *S. pneumoniae* and commensal *Neisseria*, ChoP is attached to lipopolysaccharide (LPS) and the biosynthetic pathway is well understood (Serino and Virji, 2000 Microbiology 35:1550; Weiser et al., 1989 57:3045-52; Zhang et at, 1999 Mol Microbiol 31:1477)

However, in pathogenic *Neisseria*, ChoP is covalently attached to the surface exposed pili but is not found attached to the LPS (Weiser et al., 1998 Infection & Immunity 66:4263). The position of the ChoP modification has been determined in *N. gonorrhoeae* at Serine 68 in strain MS11 (Aas et al., 2006 Journal of Biological Chemistry. 281:27712-27723). The transferase required for the ChoP to pilin of *N. meningitidis*, pptA, has been identified previously (Warren and Jennings, 2003 Infection and Immunity 71:6892-68928).

The same gene was subsequently identified in *N. gonorrhoeae* (Hegge et al., 2004 *Proc Natl Acad Sci USA* 101:10798-10803).

The role of phosphorylcholine in disease caused by pathogenic *Neisseria* is not known, nor has the function of pili post-translational modifications in host-pathogen interactions been resolved.

SUMMARY OF THE INVENTION

The present invention relates to the use of mutant glycoproteins from pathogenic bacteria lacking one or more ChoP and/or glycosylation post-translational modifications, or having modified glycosylation, as immunogens.

More particularly, the present invention relates to the surprising discovery that removal of "masking" structures from *Neisseria* glycoproteins, such as sugars and/or ChoP, can alter the proteins such that they elicit a "non-native" immune response, preferably protective against subsequent infection by the bacterium.

In a first aspect, the invention provides an isolated mutant protein of a bacterial pathogen, said isolated mutant protein lacking one or more phosphorylcholine, glycosylation and/or other post-translational modifications, or having modified glycosylation, compared to a corresponding wild-type protein thereof, including homologues or fragments thereof.

Suitably, said isolated mutant protein, or fragment thereof, is capable of eliciting an altered immune response in a host compared to a corresponding wild-type glycoprotein.

In one embodiment, said isolated mutant protein is a mutant pilin protein.

In another embodiment, said isolated mutant protein, or fragment thereof, is a mutant nitrite reductase.

Typically, said isolated mutant protein comprises an amino acid substitution or deletion that removes glycosylation.

In one particular embodiment, the bacterial pathogen is of a genus of *Neisseria*.

Preferably, said bacterial pathogen is of a species of *Neisseria meningitidis* or *Neisseria gonorrhoeae*.

In a preferred embodiment, the mutant protein is a mutant nitrite reductase.

In particular embodiments, the isolated mutant protein comprises an amino acid sequence selected from the group consisting of SEQ ID NOs: 1-9.

In a second aspect, the invention provides an isolated nucleic acid encoding (i) the isolated mutant protein of the first aspect, wherein said isolated mutant protein comprises an amino acid substitution or deletion that removes glycosylation, or (ii) a fragment of the isolated mutant protein of the first aspect.

In a third aspect, the invention provides an expression construct comprising the isolated nucleic acid of the second aspect, operably linked to one or more regulatory nucleotide sequences.

In a fourth aspect, the invention provides a bacterial cell comprising isolated mutant protein, or fragment thereof, of the first aspect.

In one embodiment, the bacterial cell is a host cell comprising the expression construct of the third aspect.

In another embodiment, the bacterial cell is produced by mutagenesis to thereby remove, inhibit or modify glycosylation of a bacterial glycoprotein.

Suitably, said bacterial cell is of a genus of *Neisseria* or is *E. coli*.

In a fifth aspect, the invention provides a method of producing the isolated mutant protein of the first aspect, or fragment thereof, in recombinant form, said method including the step of expressing said isolated mutant protein, or fragment thereof, in the bacterial host cell of the fourth aspect.

In a sixth aspect, the invention provides an antibody which binds, or is raised against, (i) the isolated mutant protein of the first aspect, or a fragment thereof, or (ii) the isolated mutant protein, or fragment thereof, produced according to the fifth aspect.

In a seventh aspect, the invention provides an immunogenic composition comprising (i) one or more one or more of the isolated mutant proteins of the first aspect, or a fragment thereof, (ii) the bacterial host cell of the fourth aspect; (iii) the isolated mutant protein, or fragment thereof, produced according to the method of the fifth aspect, and/or (iv) the antibody of the sixth aspect, and a carrier, diluent or excipient.

In an eighth aspect, the invention provides a method of eliciting an immune response in a host, said method including the step of administering to said host (i) one or more one or more of the isolated mutant proteins of the first aspect, or a fragment thereof, (ii) the bacterial host cell of the fourth aspect; (iii) the isolated mutant protein, or fragment thereof, produced according to the method of the fifth aspect, and/or (iv) the antibody of the sixth aspect, to thereby elicit an immune response in said host.

In a ninth aspect, the invention provides use of an agent selected from the group consisting of: (i) one or more one or more of the isolated mutant proteins of the first aspect, or a fragment thereof, (ii) the bacterial host cell of the fourth aspect; (iii) the isolated mutant protein, or fragment thereof, produced according to the method of the fifth aspect, and/or (iv) the antibody of the sixth aspect, for prophylactically or therapeutically treating a disease or condition caused by a bacterial pathogen in a host.

The host may be any animal, inclusive of mammals such as domestic animals, livestock, performance animals and humans.

Preferably, the host is a human.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE FIGURES

In FIG. 4D, the bar represents the full length AniA protein; sp, cleaved signal peptide with palmitoylated cysteine (1-18); N—, N-terminal repeat region (19-52); Nitrite reductase, core protein (53-354); C—, glycosylated C-terminal repeat region. NB. The region of the protein expressed and purified to determine the 3D structure of AniA "core protein" from *N. gonorrhoeae* is shown as a black line (RCSB Protein Data Bank accession 1KVS) FIG. 4E shows the number of differences seen at each amino acid position in the comparison of AniA from *N. meningitidis* strain MC58 and 42 *N. meningitidis* strains. Differences are plotted on the Y-axis. The plot only shows the differences over the region covered by the AniA "core protein" (53-354), and was used to determine the sites of highest amino acid sequence variation in the 3D structure. Black lines report differences in comparison of wild type, full length proteins (see FIG. 5A alignment), orange lines report additional differences seen when examining theoretical translations of "frame shift" strains (FIG. 5B).

FIG. 6A shows extracted ion chromatograms of ions corresponding to the tryptic peptide L$_{358}$-K$_{387}$ (with N$_{66}$ deamidated) and the same peptide with one or two DATDH monosaccharides (triple charged ions at m/z of 883.1, 959.4 and 1035.8 respectively). FIGS. 6B-6D show MS/MS spectra of non-glycosylated (FIG. 6B), mono-glycosylated (FIG. 6C), and di-glycosylated (FIG. 6D) L$_{358}$-K$_{387}$ tryptic peptide.

FIG. 8 Amino acid sequence of truncated FLAG-tagged AniA from *N. meningitidis* strain C311 (SEQ ID NO:1). As described in Example 5. Flag peptide is shown in bold.

FIG. 10 Analysis of immune response by Western blot analysis of purified truncated AniA-FLAG. AniA-FLAG purified from wild type C311, C311pglA and C311pglL were loaded on 4-12% Bis-tris Novex gel and analysed by (A) Western blots with polyclonal rabbit anti-AniA anti-sera and (B) anti-AniA monoclonal antibody.

FIG. 13 Truncated AniA proteins amplified from *N. gonorrhoeae* strain 1291 for expression in *E. coli*.

BRIEF DESCRIPTION OF THE SEQUENCE LISTING

The Sequence Listing is submitted as an ASCII text file named Sequence_Listing.txt, which was created on Jun. 19, 2011, and is 246,223 bytes, which is incorporated by reference herein.

Figure 4:
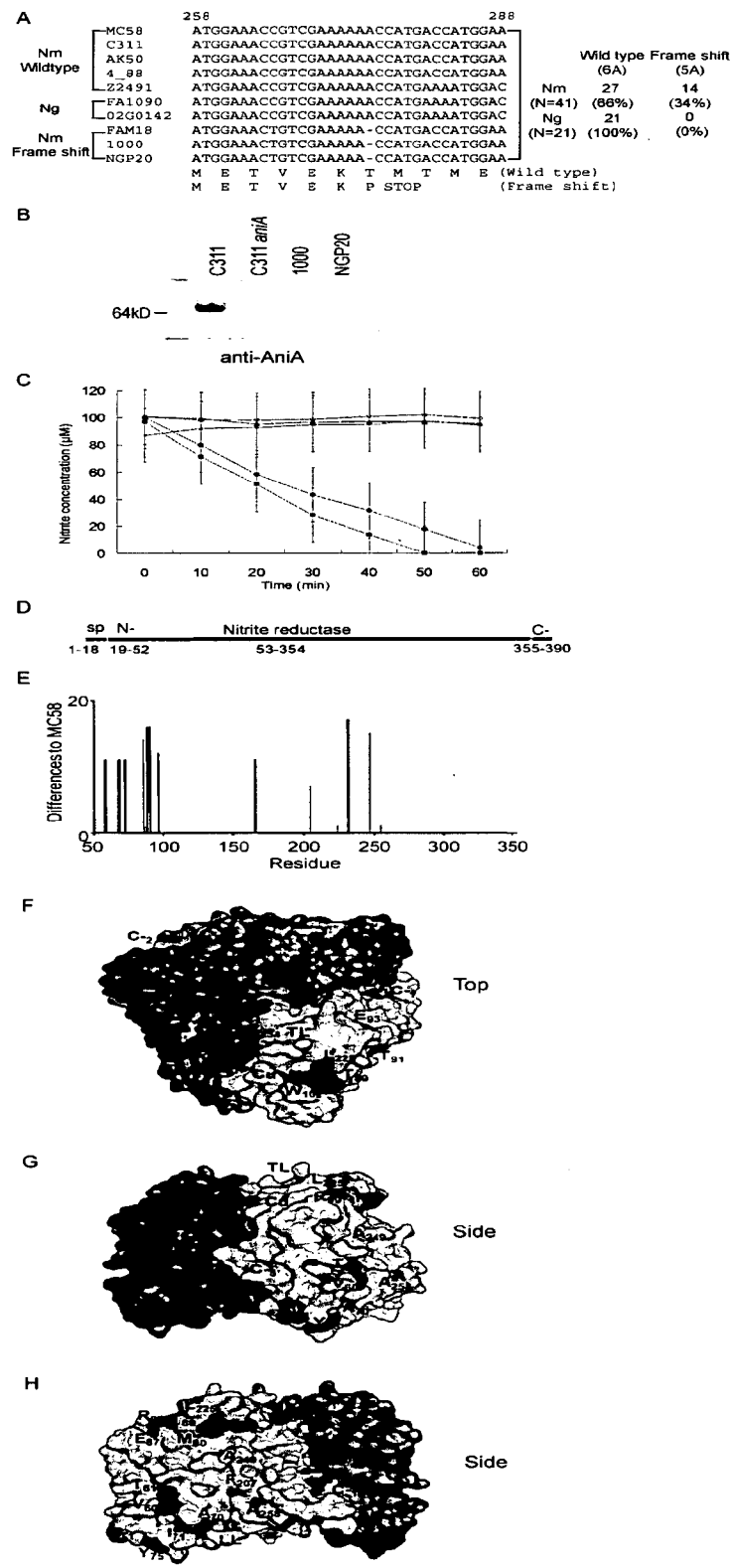
FIG. 4A is a nucleotide sequence alignment of aniA of *N. meningitidis* and *N. gonorrhoeae* strains, compared with the aniA sequence of *N. meningitidis* strain MC58 aniA sequence from base pairs 258-288 (Swiss-prot entry Q9JYE1). To the right of the comparison is the result of a survey of the frame shift mutation (6 adenosine (6A) or 5 adenosine (5A) allele) in 42 *N. meningitidis* (data derived from FIG. 5A) and 21 *N. gonorrhoeae* strains (Power, et al., 2007 Infection and Immunity 75: 3202).
FIG. 4B is an image of Western analysis of *N. meningitidis* strain C311, C311aniA and "frame shift" strains 1000 and NGP20 with anti-AniA.
FIG. 4C is a graph showing nitrite utilization vs time for wild-type C311 (filled circles), C311pglA (filled squares), C311aniA (filled triangles), and *N. meningitidis* frame shift strains 1000 (cross) and NGP20 (open circles). The cultures were supplemented with 100 μM nitrite, culture samples were collected every 10 minutes for 1 hour and the utilization of nitrite was measured colourimetrically (Anjum et al., 2002 J. Bacteriol, 184: 2087). Results are the mean of triplicate independent biological samples. Error bars show ±1 standard deviation.
FIGS. 4D and 4E are diagrams showing variation in amino acid for each residue of *N. meningitidis* AniA sequenced from 41 clinical isolates aligned against *N. meningitidis* strain MC58 AniA (see also FIGS. 5A and B).
FIGS. 4F-H are representations of MC58 AniA "core protein" trimer modelled on AniA of *N. gonorrhoeae* (RCSB Protein Data Bank accession 1KVS). Each monomer is shown in a different shade of grey. Residues of interest are only coloured in one monomer (light grey). Top view (FIG. 4F); side view (FIG. 4G), rotated 90° from FIG. 4F; and side view (FIG. 4H), rotated 90° from FIG. 4G. Red, variable amino acids in sequenced wild type *N. meningitidis* clinical isolates; green N-$_{1,2,3}$, N-terminal modelled residue, end of variable N-terminal repeat region; cyan C-$_{1,2,3}$, C-terminal modelled residue, start of glycosylated C-terminal repeat region; yellow Cu, Copper centre (buried); pale green TL and LL, Tower loop and Linker loop (deleted regions in Neisserial AniA); blue, proposed surface electron transport routes.
Figure 5A:
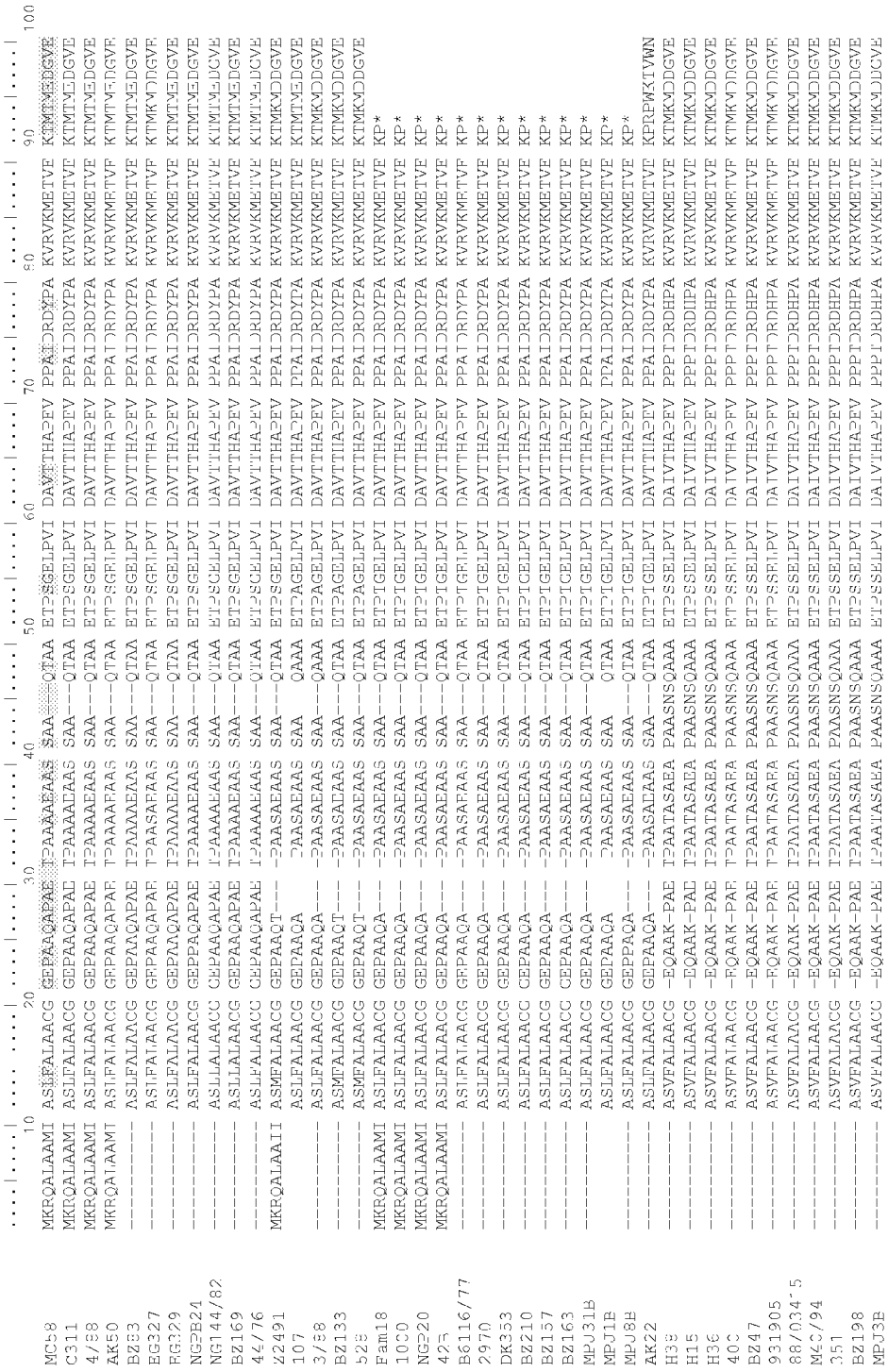
FIG. 5 AniA amino acid sequence alignment of 41 *N. meningitidis*. (A) AniA amino acid sequence alignment of 41 *N. meningitidis* strains, including 9 strains with full length sequences and 32 strains with sequences from position 11-349. SEQ ID NOS are as follows: MC58=SEQ ID NO: 31; C311=SEQ ID NO: 32; 4/88=SEQ ID NO: 33; AK50=SEQ ID NO: 34; BZ 83=SEQ ID NO: 35; EG327=SEQ ID NO: 36; EG329=SEQ ID NO: 37; NGPB24=SEQ ID NO: 38; NG144/82=SEQ ID NO: 39; BZ 169=SEQ ID NO: 40; 44/76=SEQ ID NO: 41; Z2491=SEQ ID NO: 42; 107=SEQ ID NO: 43; 3/88=SEQ ID NO: 44; BZ133=SEQ ID NO: 45; 528=SEQ ID NO: 46; FAM18=SEQ ID NO: 47; 1000=SEQ ID NO: 48; NGP20=SEQ ID NO: 49; 42B=SEQ ID NO: 50; B6116/77=SEQ ID NO: 51; 2970=SEQ ID NO: 52; DK353=SEQ ID NO: 53; BZ210=SEQ ID NO: 54; BZ157=SEQ ID NO: 55; BZ163=SEQ ID NO: 56; MPJ31B=SEQ ID NO: 57; MPJ1B=SEQ ID NO: 58; MPJ8B=SEQ ID NO: 59; AK22=SEQ ID NO: 60; H38=SEQ ID NO: 61; H15=SEQ ID NO: 62; H36=SEQ ID NO: 63; 400=SEQ ID NO: 64; BZ47=SEQ ID NO: 65; 931905=SEQ ID NO: 66; 88/03415=SEQ ID NO: 67; M40/94=SEQ ID NO: 68; 351=SEQ ID NO: 69; BZ198=SEQ ID NO: 70; MPJ3B=SEQ ID NO: 71. (B) AniA amino acid sequence alignment of wild-type AniA strains and theoretical translations of "frame shift" strains. Shaded residues showed variation within the strains analysed. SEQ ID NOS are as follows: MC58=SEQ ID NO: 72; C311=SEQ ID NO: 73; 4/88=SEQ ID NO: 74; AK50=SEQ ID NO: 75; BZ 83=SEQ ID NO: 76; EG327=SEQ ID NO: 77; EG329=SEQ ID NO: 78; NGPB24=SEQ ID NO: 79; NG144/82=SEQ ID NO: 80; BZ 169=SEQ ID NO: 81; 44/76=SEQ ID NO: 82; Z2491=SEQ ID NO: 83; 107=SEQ ID NO: 84; 3/88=SEQ ID NO: 85; BZ133=SEQ ID NO: 86; 528=SEQ ID NO: 87; FAM18=SEQ ID NO: 88; 1000=SEQ ID NO: 89; NGP20=SEQ ID NO: 90; 42B=SEQ ID NO: 91; B6116/77=SEQ ID NO: 92; 2970=SEQ ID NO: 93; DK353=SEQ ID NO: 94; BZ210=SEQ ID NO: 95; BZ157=SEQ ID NO: 96; BZ163=SEQ ID NO: 97; MPJ31B=SEQ ID NO: 98; MPJ1B=SEQ ID NO: 99; MPJ8B=SEQ ID NO: 100; AK22=SEQ ID NO: 101; H38=SEQ ID NO: 102; H15=SEQ ID NO: 103; H36=SEQ ID NO: 104; 400=SEQ ID NO: 105; BZ47=SEQ ID NO: 106; 931905=SEQ ID NO: 107; 88/03415=SEQ ID NO: 108; M40/94=SEQ ID NO: 109; 351=SEQ ID NO: 110; BZ198=SEQ ID NO: 111; MPJ3B=SEQ ID NO: 112.
Figure 5B:
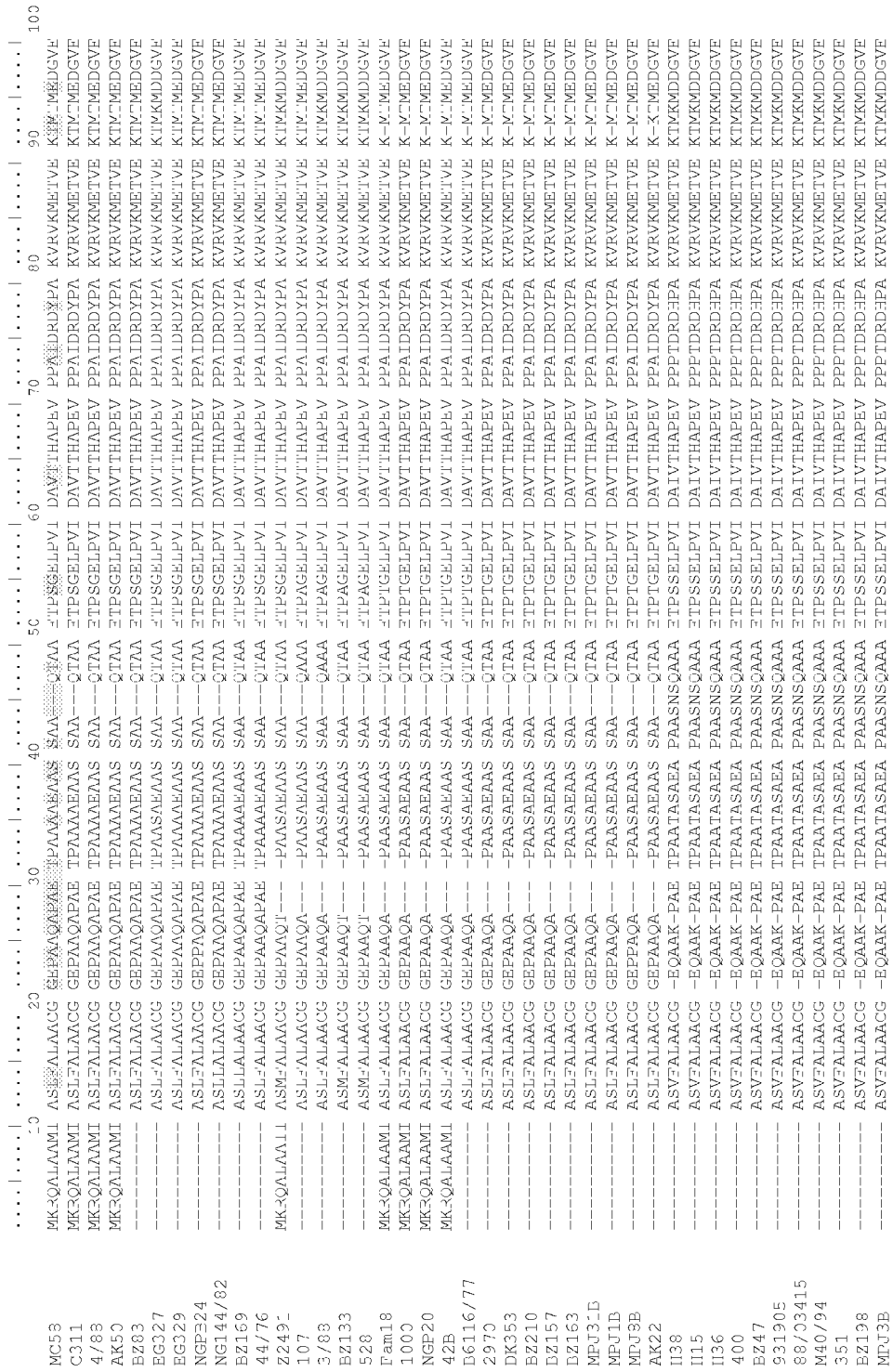

SEQ ID NO: 1: Truncated FLAG-tagged AniA (FIG. 8).
SEQ ID NOs: 2-9: Truncated AniA proteins amplified from *N. gonorrhoeae* strain 1291 for expression in *E. coli* (FIG. 13).
SEQ ID Nos: 10-14: Primer sequences (Table 1).
SEQ ID Nos: 15-20: Primer sequences (Table 2).
SEQ ID Nos: 21-30: Nucleotide sequence alignment of AniA of *N. meningitidis* and *N. gonorrhoeae* strains, compared with the AniA of *N. meningitidis* strain MC58 AniA sequence from base pairs 258-288 (FIG. 4A).
SEQ ID Nos: 31-71: AniA amino acid sequence alignment of 41 *N. meningitidis* strains, including 9 strains with full length sequences and 32 strains with sequences from positions 11-349 (FIG. 5A).
SEQ ID Nos: 72-112: AniA amino acid sequence alignment of wild-type AniA strains and theoretical translations of "frame shift" strains (FIG. 5B).

DETAILED DESCRIPTION OF THE INVENTION

The present invention is relates to mutant, modified or otherwise altered forms of bacterial glycoproteins such as pilin and nitrite reductase, particularly from pathogenic bacteria such as but not limited to *Neisseria*, and their use as immunogens. In preferred forms, the invention provides a mutant pilin protein lacking one or more of ChoP and glycosylation and/or a mutant nitrite reductase protein that lacks, or has modified, glycosylation. Pilin proteins are normally present on the bacterial surface and have a crucial role in both colonization of the host and adhesion to host cells. Wild-type pilin of pathogenic *Neisseria* contains both ChoP and glycosylation post-translational modifications. The invention also relates to another glycoprotein of *Neisseria*, AniA, which is an anaerobically induced nitrite reductase that is glycosylated by the same pathway. This demonstrates that the pilin glycosylation pathway is a general pathway for O-glycosylation in *Neisseria*. Unlike pilin, the AniA glycoprotein is not covalently modified by ChoP. It is therefore proposed that wild-type pilin and wild-type nitrite reductase thus contribute to human host-colonization.

It is also proposed that glycosylation, and/or Cho-P post-translational modification of certain bacterial proteins (including but not limited to pilin and nitrate reductase of *Neisseria* species) constitute "masking" structures that facilitate immune evasion by pathogenic bacteria. These masking structures may normally elicit a "native" immune response which is predominantly directed to the masking structure but which is not protective or otherwise useful to the host.

More particularly, the present invention is directed to the production and use of isolated pilin and nitrite reductase proteins, or fragments thereof, that lack "masking" structures such as tri-saccharide sugars and/or ChoP to thereby elicit an altered immune response which is more beneficial to the host.

By "altered" in this context is meant distinct, "non-native" immune response that preferably protects against subsequent infection by the bacterium, or is at least more immunologically effective than the native immune response. By removing either ChoP and/or sugar groups, or by reducing the number of the sugar groups from a bulky trisaccharide to a di- or monosaccharide group, the mutant pilin and/or nitrite reductase underlying conserved structure will be more exposed, or 'unmasked' to thereby enable both novel and improved antigen processing and hence a more protective immune response.

Although the present invention is exemplified herein with respect to generating novel immune responses to bacterial pathogens of the genus *Neisseria*, such as *N. meningitidis* and *N. gonorrhoeae*, the general principle provided by the present invention is applicable to Gram-negative or Gram-positive bacterial pathogens with surface expressed post-translationally modified proteins. Furthermore, while the pilin and nitrite reductase glycoproteins exemplified herein comprise O-linked glycosylation, the invention may also be practised with N-linked glycoproteins.

Particular, non-limiting examples of other pathogenic bacteria include bacteria of the genera *Campylobacter, Helicobacter, Pseudomonas* and *Mycobacterium*. For example, reference is made to Wacker et al., 2002 Science 298 790 and Szymanski et al., 1999, Mol. Microbiol. 32 1022. Particular reference is also made to reviews by Power & Jennings, 2003, EMS Microbiol. Lett. 218 211 and Szymanski & Wren, 2005, Nat. Rev. Microbiol. 3 225, which describe several other bacterial glycoproteins that may be modified according to the present invention.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical, synthetic or recombinant form.

By "antigenic" is meant capable of being recognized by components of the host immune system, such as antibodies.

By "immunogenic" is meant capable of eliciting an immune response, preferably a protective immune response upon administration to a host.

By "protein" is meant an amino acid polymer comprising D- or L-amino acids and/or natural or non-natural amino acids as are well understood in the art.

A "peptide" is a protein having no more than fifty (50) amino acids.

A "polypeptide" is a protein having more than fifty (50) amino acids.

Throughout this specification, a "glycoprotein" is a protein, peptide or polypeptide that comprises one or more glycosyl moieties or is otherwise "glycosylated" as is well known in the art. This definition includes O-linked and N-linked glycosylation. Preferably, the glycosyl moieties or glycosylation is O-linked to the protein via a serine or threonine residue. By way of example only, reference may be made to Chapter 12 of Coligan et al., CURRENT PROTOCOLS IN PROTEIN SCIENCE (John Wiley & Sons Inc. NY, 1991-2008), which provides the skilled reader with general information about the structure, analysis and preparation of glycoproteins.

By "mutant" is meant a protein lacking one or more of ChoP, glycosylation and/or other post-translational modifications, or having modified glycosylation compared to a wild-type glycoprotein.

Such mutant proteins may have amino acid substitutions, additions and/or deletions (e.g truncations) that substantially or completely prevent or inhibit glycosylation and/or Cho-P addition.

By way of example, a pilin glycoprotein of *N. meningitidis* may be glycosylated at serine 63 or a corresponding S or T residue that is capable of O-linked glycosylation. Reference to serine 63 of *N. meningitidis* pilin is made herein in the context of the pilin sequence described in Power et al., 2006, supra and other pilin sequences such as available under Genbank accession nos: AAA25487 and AAA67333. It will also be appreciated that the invention also extends to homologous serine or threonine resides in pilin and other bacterial proteins that are capable of capable of O-linked glycosylation.

Cho-P modification of pilin may be at serine 68 in *N. gonorrhoeae* strain MS11 or serine 156 and/or 160 on pilin of *N. meningitidis* strain C311.

Also by way of example, a nitrite reductase protein may be O-glycosylated at one or more carboxy terminal serine-containing peptide repeats, or homologous sequences in nitrite reductase protein and other bacterial proteins that are capable of capable of O-linked glycosylation. In this regard, reference is made to FIG. 5, for guidance as to the location of carboxy terminal serine-containing peptide repeats of *N. meningitidis* AniA nitrite reductase in a variety of *N. meningitidis* strains.

In further embodiments, a mutant nitrate reductase protein may comprise N-terminal deletions in addition to deletion of one or more carboxy terminal serine-containing peptide repeats.

In certain embodiments, the mutant proteins comprise a substitution and/or deletion of one or more amino acids at these exemplary glycosylation sites.

Particular, non-limiting examples of embodiments of a nitrite reductase of *N. meningitidis* (SEQ ID NO: 1) or *N. gonorrhoeae* (SEQ ID NOs: 2-9) having deletions of an O-linked glycosylation site are provided.

In another embodiment, the mutant protein is produced in a genetically-modified bacterium to produce a mutant protein having modified glycosylation. Non-limiting examples of modified glycosylation include O-linked monosaccharides such as 2,4-diacetamido-2,4,6 trideoxyhexose (DATDH) or glyceramido acetamido trideoxyhexose (GATDH) or disaccharides such as Gal α (1-3) 2,4-diacetamido-2,4,6 trideoxyhexose or Gal α (1-3) glyceramido acetamido trideoxyhexose.

Preferably, the disaccharide is not Gal α (1-3) GlcNAc.

The invention also provides fragments of the isolated mutant proteins.

Fragments may comprise 10, 20, 30, 40, 50, 60, 70, 80, 90, 100, 150, 200, 250, 300, 350 or more contiguous amino acids of a mutant protein, such as a nitrite reductase or pilin protein, but less than the full-length amino acid sequence of the mutant protein.

Preferably, fragments do not comprise one or more glycosylation site residues and/or residues for ChoP addition, as hereinbefore described.

Alternatively, fragments may comprise modified glycosylation as hereinbefore described.

For example, such fragments may be produced by enzymatic cleavage of mutant proteins having modified glycosylation.

In other embodiments, chemical synthesis is optimally utilized for peptides and other protein fragments that do not exceed 60-80 contiguous amino acids in length. Peptides and protein fragments may further comprise modified glycosylation produced by chemical synthesis. Such methods are well known in the art and may be available "ready to order" from commercial sources.

In a preferred form, the aforementioned fragments are immunogenic.

More preferably, the fragments elicit an antibody response.

Even more preferably, the fragments elicit a protective immune response.

The invention also contemplates "derivatives" of the isolated mutant proteins and fragments thereof. Such derivatives may include chemical derivatives, biotinylated mutant proteins, additional amino acid sequences (such as epitope tags and fusion partners) as are well understood in the art. More detailed examples of chemical modification of proteins are provided in Chapter 15 of Coligan et al., CURRENT PROTOCOLS IN PROTEIN SCIENCE (John Wiley & Sons Inc. NY, 1991-2008).

Fusion partners (e.g. MBP, His, GST & GFP) and epitope tags (e.g FLAG, myc & HA) may be particularly useful for recombinant protein purification and/or detection, as is well known in the art.

The invention also provides an isolated nucleic acid encoding the isolated mutant protein of the invention, including fragments thereof.

The term "nucleic acid" as used herein designates single- or double-stranded mRNA, RNA, cRNA and DNA inclusive of cDNA and genomic DNA and DNA-RNA hybrids.

In particular embodiments, isolated nucleic acids may facilitate recombinant mutant protein production.

Accordingly, the invention provides an expression construct comprising an isolated nucleic acid the isolated mutant protein of the invention, including fragments thereof, operably linked to one or more regulatory sequences that facilitate bacterial expression of recombinant proteins and peptides.

Non-limiting examples of regulatory sequences include a bacterial origin of replication, selection marker sequences, sequences that facilitate homologous recombination, transcription and/or translation regulatory sequences and other regulatory sequences as are well known in the art.

In one particular embodiment, recombinant expression of mutant proteins may be performed using bacteria genetically modified to lack or otherwise have altered expression of one or more enzymes involved in glycosylation and/or ChoP addition.

Examples of genes involved in glycosylation include pglA, pglE, pglG, pglH, pglI and pglL.

An example of a gene involved in ChoP addition is pptA.

A more extensive description of genes involved in the glycosylation of pilin and AniA that may facilitate manipulation of bacterial strains to produce mutant proteins with modified or absent glycosylation are provided in Jennings et al., 1998 Molecular Microbiology 29:975-984; Power et al., 2000 Microbiology 146:967-979; Power et al., 2000 Microbiology 146:967-979; Power and Jennings, 2003 FEMS Microbiology Letters 218: 211-222; Warren et al., 2004 FEMS Medical Microbiology and Immunology 41:43-50; Power et al., 2006 Biochemical and Biophysical Research Communications 347:904-908).

Examples of bacteria for recombinant protein expression are bacteria such as N. meningitidis, N. gonorrhoeae and E. coli (for example DH5α, XL1Blue, BL21(DE3), Origami and Rosetta), although without limitation thereto.

The mutant protein may be produced using genetically-modified N. meningitidis bacteria, particularly where modified glycosylation (as hereinbefore described) is required.

Alternatively, the mutant protein may be produced in a "standard" expression host such as E. coli, although without limitation thereto. This embodiment is particularly useful for the expression of isolated mutant proteins, or fragments thereof (such as set forth in SEQ ID NOS:1-9), that lack glycosylation sites.

It will also be appreciated that bacterial cells may be produced that express isolated mutant proteins of the invention, including fragments thereof, by random mutagenesis.

Chemical mutagenesis, for example, may be used to randomly mutate genes required for protein glycosylation. Mutagenized bacteria may then be selected according to an absence of glycosylation, or modified glycosylation of a glycoprotein of interest.

Bacterial cells may also be suitable for delivery of isolated mutant proteins in the context of immunogenic compositions and/or methods of eliciting an immune response. Preferably, the bacterial host is attenuated or inactivated, such as by physical, chemical or genetic means, as is well understood in the art.

One particular aspect of the invention provides antibodies which bind, recognize and/or have been raised against isolated mutant proteins of the invention, or fragments thereof.

In particular embodiments, antibodies may bind specific epitopes in a mutant pilin or mutant nitrite reductase protein of the invention.

Suitably, said antibody does not bind a corresponding wild-type glycoprotein, or glycosyl moieties thereof, or binds said wild-type glycoprotein with a lower affinity than said isolated mutant protein.

For example, the "unmasking" of isolated mutant proteins or fragments thereof may expose or otherwise reveal immunogenic epitopes that elicit a "non-native" antibody response that does not normally occur in response to the wild-type glycoprotein.

Preferably, the antibody is bactericidal and/or opsonophagocytic.

In particular embodiments, antibodies of the invention may be useful for "passive immunization" of a host against a bacterial pathogen.

Antibodies may also include antibody fragments such as Fc fragments, Fab and Fab'2 fragments, diabodies and ScFv fragments. Antibodies may be monoclonal or polyclonal.

Antibodies may be made in suitable production animal such as a mouse, rat, rabbit, sheep, chicken or goat.

Well-known protocols applicable to antibody production, purification and use may be found, for example, in Chapter 2 of Coligan et al., CURRENT PROTOCOLS IN IMMUNOLOGY (John Wiley & Sons Inc. NY, 1991-2008) and Harlow, E. & Lane, D. *Antibodies: A Laboratory Manual* (Cold Spring Harbor Laboratory, 1988).

Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

Monoclonal antibodies may be produced using standard methods, as for example described in an article by Köhler & Milstein 1975 Nature 256: 495, or by more recent modifications thereof as for example, described in Coligan et al., CURRENT PROTOCOLS IN IMMUNOLOGY, supra.

The invention also includes within its scope antibodies which comprise Fc or Fab fragments of the polyclonal or monoclonal antibodies referred to above. Alternatively, the antibodies may comprise single chain Fv antibodies (scFvs). Such scFvs may be prepared, for example, in accordance with the methods described respectively in U.S. Pat. No. 5,091,513, European Patent No 239,400 or the article by Winter & Milstein 1991 Nature 349: 293.

The antibodies of the invention may include a label selected from a group including a chromogen, a catalyst, an enzyme, a fluorophore, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

Several enzymes suitable for use as labels are disclosed in U.S. Pat. No. 4,366,241, U.S. Pat. No. 4,843,000, and U.S. Pat. No. 4,849,338. Suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution.

Fluorophores may be selected from a group including fluorescein isothiocyanate (FITC), tetramethylrhodamine isothiocyanate (TRITC), allophycocyanin (APC), Texas Red (TR), PerCP, Cy3, Cy5 or R-Phycoerythrin (RPE). Examples of useful fluorophores may be found, for example, in U.S. Pat. No. 4,520,110 and U.S. Pat. No. 4,542,104.

In other aspects, the invention provides for the use of an agent such as an isolated mutant protein, or fragment thereof, antibodies thereto or bacterial hosts that express said isolated mutant protein, or fragment thereof, for eliciting an immune response in a host, such as a human host.

The present invention also provides immunogenic compositions which may be used therapeutically or prophylactically. Such immunogenic compositions may comprise agents such as isolated mutant proteins, fragments thereof, antibodies thereto, or bacterial hosts that express said isolated mutant protein, or fragment thereof.

Suitably, the method, use of composition, elicits a "non-native" immune response when administered to a host.

Preferably, the "non-native" immune response is a protective immune response. In such embodiments, the immunogenic composition may be a vaccine.

Immunogenic compositions may be in any of a variety of forms:

(i) bacterial host cells engineered to express a mutant protein or fragment thereof (for example an attenuated bacterium such as *N. meningitidis*);

(ii) a mutant protein or fragment thereof in recombinant form;

(iii) a chemically synthesized mutant protein or fragment thereof;

(iv) an antibody that binds or is raised against a mutant protein or fragment thereof; or (v) any combination of (i)-(iv).

Suitably, the immunogenic composition is administrable to an animal host, inclusive of mammals such as domestic animals, livestock, performance animals and humans.

Preferably the host is a human.

Suitably, the immunogenic composition, use and/or method elicits an immune response to one or more pathogenic bacteria. Such bacteria include *Neisseria* sp, *Campylobacter* sp, *Helicobacter* sp, *Pseudomonas* sp and *Mycobacterium* sp, although without limitation thereto.

In one particular non-limiting embodiment, it is proposed that a mutant nitrite reductase (AniA) may be particularly useful for prevention of disease caused by *N. gonorrhoeae*.

Accordingly, the immunogenic composition, use or method may prophylactically or therapeutically treat a disease or condition caused by, or otherwise associated with, an infection by said pathogenic bacterium.

Any suitable procedure is contemplated for producing immunogenic compositions, inclusive of vaccines. Exemplary procedures include, for example, those described in New Generation Vaccines (Levine et al., 1997).

The immunogenic composition of the invention may include an "immunologically-acceptable carrier, diluent or excipient".

Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas*, *E. coli*, *Staphylococcus*, and *Streptococcus*; polyamino acids such as poly (lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a T cell epitope of a bacterial toxin, toxoid or CRM may be used. In this regard, reference may be made to U.S. Pat. No. 5,785,973.

The "immunologically-acceptable carrier, diluent or excipient" includes within its scope water, bicarbonate buffer, phosphate buffered saline or saline and/or an adjuvant as is well known in the art. Suitable adjuvants include, but are not limited to: surface active substances such as hexadecylamine, octadecylamine, octadecyl amino acid esters, lysolecithin, dimethyldioctadecylammonium bromide, N,N-dicoctadecyl-N',N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

Any safe route of administration may be employed for providing a patient with the immunotherapeutic composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions and vaccines.

The above compositions may be administered in a manner compatible with the dosage formulation, and in such amount as is immunologically-effective. The dose administered to a patient, in the context of the present invention, should be sufficient to induce a beneficial response in a patient over an appropriate period of time. The quantity of agent(s) to be administered may depend on the subject to be treated inclusive of the age, sex, weight and general health condition thereof, factors that will depend on the judgement of the practitioner.

Dosage forms may include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be achieved by using other polymer matrices, liposomes and/or microspheres.

Compositions of the present invention suitable for oral or parenteral administration may be presented as discrete units such as capsules, sachets or tablets each containing a predetermined amount of one or more immunogenic agents of the invention, as a powder or granules or as a solution or a suspension in an aqueous liquid, a non-aqueous liquid, an oil-in-water emulsion or a water-in-oil liquid emulsion.

In a further embodiment, the isolated mutant protein may comprise modified glycosylation that includes heterologous glycosyl moieties that are normally present on other glycoproteins but not on the corresponding wild-type glycoprotein.

As demonstrated herein, the ability of glycoproteins such as wild-type pilin and nitrate reductase to elicit strong antibody responses to glycosyl moieties/glycan structures "displayed" by these glycoproteins, makes them ideal "platforms" for eliciting antibody responses to heterologous glycosyl moieties. In many cases, it is difficult to elicit antibody responses to glycosyl moieties, in which case the invention contemplates "artificially glycosylated" proteins (such as pilin or nitrate reductase, or peptides corresponding to the glycosylated regions) that facilitate generation of antibody production to the "artificial" glycosylation.

Such antibodies may have diagnostic or therapeutic use, for example in vaccines. In particular embodiments, glycosylation could be added to the protein by engineering the system into E. coli, or by adding glycosylation to a peptide that corresponds to the repeating pentapeptide in the C-terminus of a nitrite reductase such as AniA.

In order that the invention may be readily understood and put into practical effect, particular preferred embodiments will now be described by way of the following non-limiting examples.

EXAMPLES

Introduction

Pilin of pathogenic *Neisseria* appeared to have all of the characteristics of ideal vaccine candidates. They are required for colonization, are surface exposed and immunogenic. However, subsequent investigations describing the specific mechanisms for high frequency changes in the amino acid sequence of the pilin glycoprotein implied that they were unsuitable as vaccine antigens. Although there is a very high frequency of sequence change in the pilin subunit protein, PilE, some short regions of conservation exist. The region of the pilin subunit that is glycosylated (Serine 63) and the glycosylated region of AniA (carboxy terminal serine containing peptide repeats) are relatively conserved with respect to amino acid substitutions associated with antigenic variation. Conservation of the underlying amino acid sequences is presumably due to maintenance of the glycosylation site. Transferases operate with a high degree of specificity and the inventors hypothesize that the conserved recognition sequences on pilin and AniA will be required for transfer to occur for both pilin and AniA glycosylation and/or ChoP modification, and/or other post-translational modifications.

In the case of AniA the extent of sequence variation amongst the sequences that are known is far less than for pilin, which is a clear example of high frequency immune evasion mechanism. In the case of AniA the data herein show an almost exclusive immune response directed towards the glycan (monosaccharide in this case from the rabbit immune data) suggests that removal of this sugar will allow a response to part of the protein other then the glycan. Our structural analysis of AniA notes that the carboxy-terminal extension on AniA from *Neisseria* is not present in other bacterial that express AniA, and is not part of the well defined active site mechanism—in fact this flexible (predicted to be flexible) C-terminal extension may "overly" these active site residues. Therefore the deletion of this region (as described in the truncation experiments in mice, may serve a two-fold purpose: 1. To remove the glycosylation by removing the target that is glycosylated (in this way there is no requirement for any PT modifications and the protein can be made in *e-coli* as described in later examples), and; 2. The removal of this flexible, repeating pentapeptide, and even larger truncations of the C-terminus (described in the *E. coli* expressed examples) may also further focus the immune response on the remained of the AniA protein that contains the key active site resides that would allow a functional blocking immune response in addition to antibodies that have other functions such as bactericidal or opsonophagocytic activities.

In *N. gonorrheae* this protein is expressed by all strains tested, and does not have the silencing mutations we have found in *N. meningitidis* (where ~30% of clinical isolates to not express the protein at all). Further, in *N. gonorrhoeae*, the function of AniA is a key for formation of biofilms, so generation of these functional blocking antibodies is anticipated to have a similar response to the mutation. Finally, in the latter examples we have proposed removal of N-terminal regions of AniA in addition to the C-terminal regions. We note that the N-terminal region of AniA from *Neisseria* is not present in other bacterial that express AniA, and, like the C-terminal extension is not part of the well defined active site mechanism—in fact this flexible (predicted to be flexible) N-terminal extension is the site where a lipid modification is added (*Neisseria* AniA is a lipoprotein) to anchor the bacterial to the membrane (in other bacteria AniA is not a lipoprotein), therefore the deletion of this N-terminal region, in addition to the C-terminal region may further direct the immune response to the conserved, regions required for AniA function.

Thus, a conserved amino acid sequence, usually masked by a glycan and/or ChoP, if presented without the overlying structure, may elicit antibodies of novel specificity that can recognize the conserved epitopes on pilin and AniA regardless of the post-translational modification.

Example 1

Vaccines Comprising Glycosylation Modified Mutant Pili

The glycosylated region of pilin is proposed to be on the surface of the pilus structure and has a relatively conserved amino acid sequence, hence the present inventors hypothesis that the removal of immunogenic and variable structures from pilin such as sugars and ChoP may elicit "non-native" immune responses against subsequent infection. Specifically, the substitution of trisaccharides for shorter mono- or disaccharides on pilin protein or pilin devoid of glycosylation is hypothesized to promote a novel antibody response not generated with wild-type pili.

Reference is made to Power et al., 2003 Mol Microbiology, 49: 833; Power et al., 1999 Microbiology 145: 3013; Jennings et al., 1998 Mol Microbiology 29: 975; Power and Jennings, 2003 FEMS Microbiology Letters 218: 211-222; Warren et al., 2004 FEMS Medical Microbiology and Immunology 41:43-50; Power et al., 2006 Biochemical and Biophysical Research Communications 347:904-908, which describe characterization of the pglA, pglB, pglC, pglD, pglE, pglF and, pglI genes, that play specific and important roles in the biosynthesis of pilin glycans having a terminal galactose as part of a Galβ(1-4)Gal(α1-3)DATDH structure and, in some cases, in biosynthesis of the disaccharide Gal(α1-3) GlcNAc. Furthermore, the basal sugar that is O-linked to Serine, DATDH, can be modified depending on whether the strain expressing the pilin has the pglB1 or pglB2 allele (Power et al., 2003 Molecular Microbiology 49: 833; Chamot-Rooke et al., 2007 PNAS 104: 14783-14788), and whether pglI is phase varied ON or OFF (Warren et. al, 2004, FEMS Medical Microbiology and Immunology 41:43-50; Chamot-Rooke et al., 2007, PNAS 104: 14783-14788).

The present invention provides a pilin peptide epitope comprising a relatively conserved peptide and a truncated oligosaccharide structure. Preferably, the truncated oligosaccharide is a monosaccharide (either a 2,4-diacetimido-2,4,6-trideoxyhexose or variant structure based on PglB allele and PglI expression) linked at serine 63 to a short peptide comprising the conserved amino acid sequence that underlies the glycosylation site. Those epitopes which are found present in all strains expressing pili and elicit functional antibodies, will be incorporated into vaccines.

Suitable glycopeptides are produced using the His-tagged pilin (Dieckelmann, et al., 2003 Protein Expression and Purification 30:69-77) or FLAG-tagged expression system in strain C311pglA and a strain expressing and alternate basal sugar structure such as strain 8013 SB pglA. These strains will express the minimal monosaccharide structures. In some embodiments, proteins may be cleaved with trypsin to release a 28 amino acid peptide. The peptides may be purified by HPLC, the identity and purity confirmed by ESI-MS and used in two separate approaches:

Example 2

PilE::Flag Construction

Flag-tag was chosen as an alternative tag system to purify pilin. Flag-tag, also called Flag octapeptide, consists of eight amino acids (DYKDDDDK) that bind to the commercially available monoclonal antibodies M1 and M2 with high specificity. The tag was fused at the C-terminus of PilE to avoid interference with secretion. To fuse the Asp-Tyr-Lys-Asp-Asp-Asp-Asp-Lys (M2 Flag) tag to the C-terminus of the chromosomally located pilE gene of C311#3, the construct pGEMTetMBpilE::Flag/lpxC was constructed to facilitate the tagging of the PilE protein. The pilE gene was amplified from strain C311#3 using the primers PilE-NotI (5'-GACCTG-CAGGCGGCCGCGAATTCACTA-3') and Flag-XhoI (5'-TTAAAACTC-GAGCTTATCGTCGTCATCCTTGTAATCGCTAGCATCACTTGCGTCGCGGCAGG-3'. The Flag-XhoI primer has Flag tag and XhoI digestion site extension to allow incorporation of the tag in-frame with pilE. The resulting pilE::Flag DNA fragment was and ligated to pGEMTetMpilEMCS/lpxC to have pGEMTetMBpilE::Flag containing the correct orientation of pilE::Flag.

This plasmid pGEMTetMBpilE::Flag/lpxC, contains the pilE gene with a Flag-tag, a tetracycline cassette used as a selectable marker, an intergenic region, and part of a gene downstream of pilE on the chromosome to allow homologous recombination to occur as shown. The construct was linearised with NotI and transformed into C311#3. Transformants in which the pilE::Flag allele had replaced the pilE region on the chromosome were selected by growth on BHI containing 5 μg/ml tetracycline. This resulted in the tagged allele being transferred to the chromosome of N. meningitidis C311#3. The plasmid pGEMTetMBpilE::Flag/lpxC was also transformed into glycosylation and phosphorylcholine mutants C311pglA (Jennings et al., 1998 Molecular Microbiology 29:975-984)), C311pptA (Warren and Jennings, 2003 Infection and Immunity 71:6892-68928) and C31126ApglA (Warren and Jennings, 2003) to have C311pilE::Flag C311pglA/pilE::Flag, C311pptA/pilE::Flag and C31126ApglA/pilE::Flag.

Flag-Tagged Pilin Purification

Figure 1:
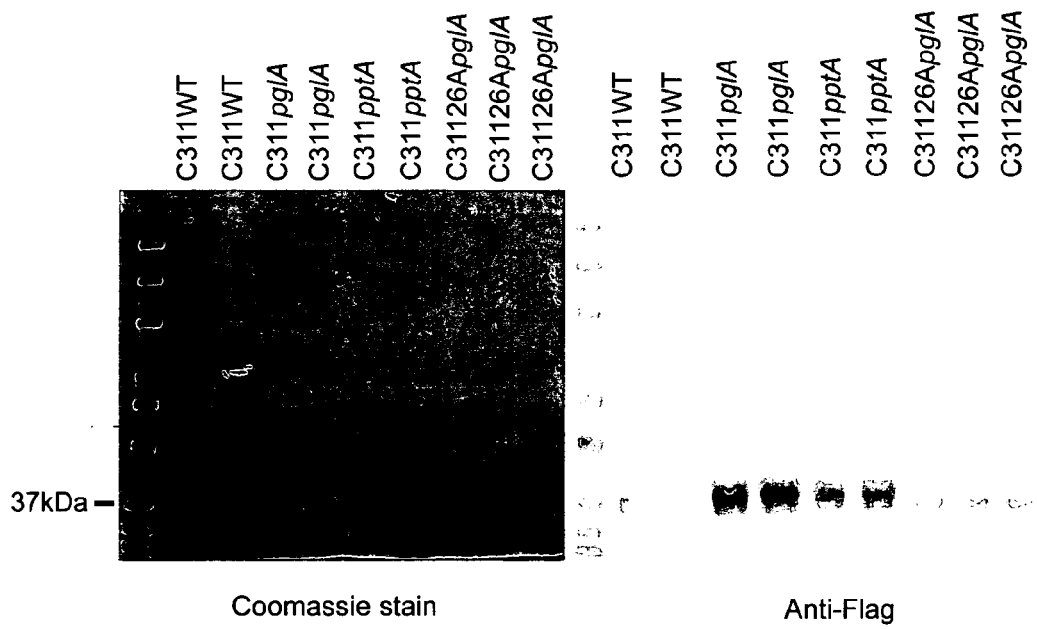
FIG. 1 Coomassie stain and western analysis of Flag-tagged pilin antigen for mouse immunization. Flag-tagged pilin antigens purified from C311 wild type, C311pglA, C311pptA, C31126ApglA were loaded on 4-12% Bis-Tris Novex gel and analysis by coomassie stain and western blots with anti-Flag mAb.

Heavily inoculated confluent cultures of C311#3pilE::Flag were grown overnight on large BHI plates (135-mm diameter; 5 plates). Each large plate of cells was harvested into 15 ml TE buffer (10 mM Tris-Cl, pH 7.5, 1 mM EDTA) and heat-killed for 1 h at 56° C. Complete EDTA-free Protease Inhibitor Cocktail was resuspended according to manufacturer's instructions (Roche), and the cells were French-pressed five times at 1000 psi gauge pressure. The lysate was centrifuged twice at 14,000 g for 30 min at 4° C. The supernatant was collected, filtered through a 0.22-μm filter (Amicon), and applied to an anti-flag affinity gel column for Flag-tagged protein purification. The entire 15 ml supernatant was loaded on a 15 ml column volume with 1 ml of anti-flag ANTI-FLAG® M2 Affinity Gel (Sigma) that had been washed with TBS buffer (50 mM Tris HCl, 150 mM NaCl, pH7.4). The binding of Flag-tagged pilin to resin was incubated on the rotor in 4° C. for overnight. The column was subsequently washed with twenty column volumes of TBS buffer and Flag-tagged pilin was eluted with eight 1 ml aliquots of 0.1M Glycine HCl (pH3.5) into vials containing 20 μl of 1M Tris, pH8.0. Purified Flag-tagged pilin (antigen for mouse immunization) from C311pil/E::Flag C311pglA/pilE::Flag, C311pptA/pilE::Flag and C31126ApglA/pilE::Flag was analyzed as shown in FIG. 1. Purified antigen were used to immunize Balb/C mice (mice, 10 per group, vaccinated with 5 μg of protein/peptide+Adjuvant (Freunds) at days 0, 21 and 28 and sacrificed on day 35.

Antigen Preparation for Western Blot Analysis

Pilin was prepared based on previously described methods (Virji, 1993 Molecular Microbiology 10:1013-1028). The cells from a plate of overnight growth were added to 500 μl of PBS. The pili were sheared off the outside of the cells by vortexing vigorously for 1 min and the cells were removed from the mixture by centrifuging at 12,000 g in a bench-top centrifuge for 15 min. The supernatant was transferred to a new tube and incubated at 56° C. for 1 hr to kill any remaining cells.

Figure 2:
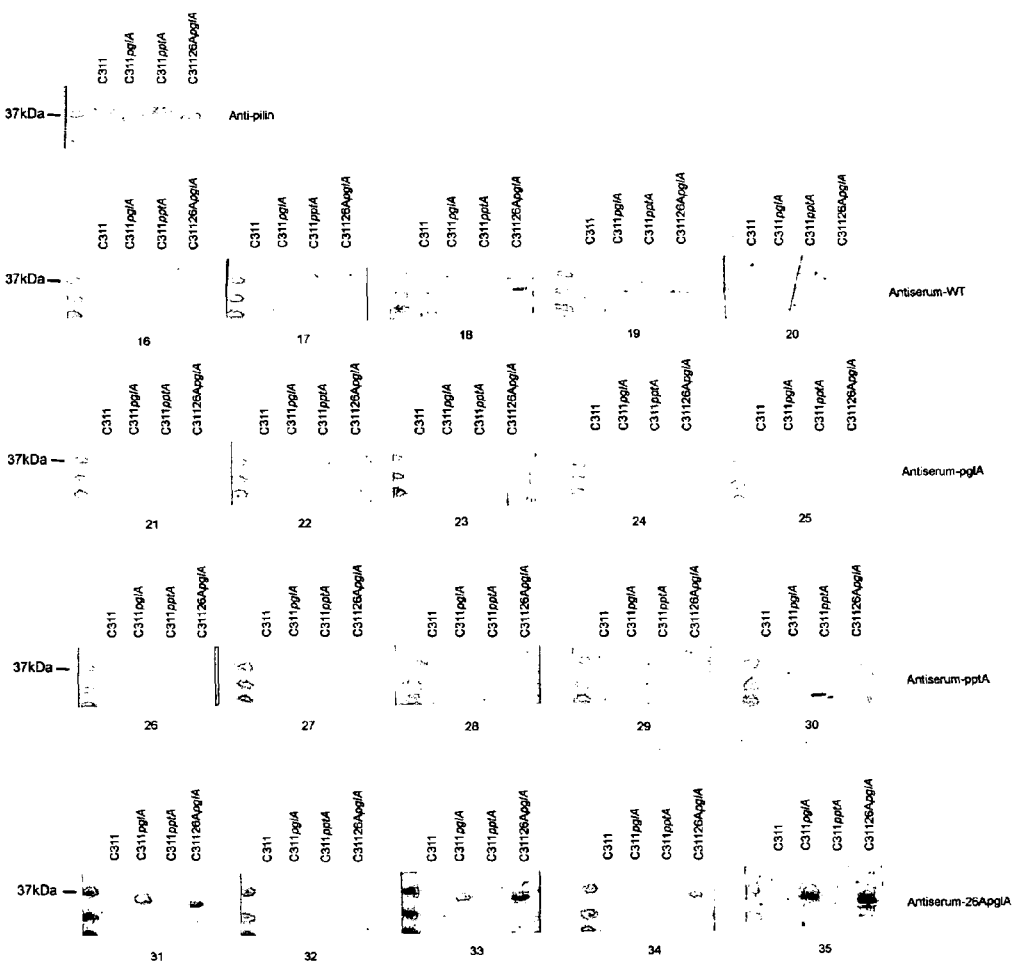
FIG. 2 Monitor of immune response by western blots analysis of vortex pilin probing with mouse antisera raised against pilin-WT, pilin-pglA, pilin-pptA and pilin-26ApglA.

Vortex pilin from C311 WT, C311pglA (Jennings et al., 1998), C311pptA (Warren and Jennings, 2003) and C31126ApglA (Warren and Jennings, 2003) were balanced by western probed by anti-pilin as shown in FIG. 2. The balanced samples were analyzed by western with the antiserum. In FIG. 2, the number 16-35 represents the mouse number. Mice 16-20 were immunized with C311 WT Flag-tagged pilin. Mice 21-25 were immunized with C311pglA Flag-tagged pilin. Mice 26-30 were immunized with C311pptA Flag-tagged pilin. Mice 31-35 were immunized with C31126ApglA Flag-tagged pilin.

Example 3

Development of Monoclonal Antibodies to Define Protective, Conserved Epitopes

Experiments to develop monoclonal antibodies using Balb/C mice for the production of monoclonal antibodies (mAbs; 5 per group, vaccinated with 5 µg of pure protein or peptide+MPL, boosted to high titre) are scheduled. The antigens used in ELISA to identify anti-pili mAbs will be whole cells of C311#3 and C311#3pilE::kan, which do not express pili. In order to find a sub-set of mAbs that have an epitope consisting of or including the ChoP modification site, purified pilin from C311#3 and derivatives of this strain that have a site directed mutation which removes the ChoP modification site (as above) will be used. Routine procedures of splice overlap PCR to make site-directed changes to pilin sequence are then performed. MAbs of the appropriate specificity may be tested in a number of ways:
1. Whole cell ELISA on large collections of strains to determine the proportion of strains that express a particular epitope. A C311#3pilE::kan mutant strain serves as the negative control. If no binding is observed in a particular strain, confirmation may be made that the strain is expressing pili by EM.
2. Bactericidal killing (BC) assays on capsulate *N. meningitidis* C311#3 and a range of heterologous strains to determine the BC titre for each monoclonal (eg. Hoogerhout et al., 1995) may be conducted.
3. Opsonophagocytic assays on capsulate *N. meningitidis* C311#3 plus a range of heterologous strains using methods described in Plested et al., 1999 may be conducted.
4. If this approach yields mAbs that define candidate epitopes and have BC or opsonophagocytic activity, then development of the antigen to optimize the production of the desired specificity follows. Characteristics such as size of peptide, conjugations to a carrier and adjuvent systems are then ascertained.

In preliminary experiments, monoclonal antibodies specific for pili glycosylation structures have been raised. BalB/C mice were immunised with wild type pilin expressed as a HIS tagged molecule in *Neisseria* that retains post-translational modifications (Dieckelmann et al., 2003 Protein Expression and Purification 30:69). Hybridomas were first screened in whole cell ELISA against wild-type, strain C311#3, or C311#3pilE::kan which does not express pili. Hybridomas specific for "pili antigens" were then subject to secondary screening, again using whole cell ELISA, but this time with wild-type C311#3 and a panel of C311#3 mutants strains expressing pili with various defects in glycosylation. Reactivity with wild type C311#3 that is lost in a specific mutant indicates that the glycan structure absent in that mutant is required for monoclonal antibody recognition and may indicate a monoclonal antibody specific for a particular glycan structure. Of the 183 hybridomas recognizing "pili antigens" that were screened, none were directed at oligosaccharide structures.

However, in secondary studies, the same set of 183 hybridomas against wild type C311#3 which expresses ChoP on pili and the C311#3 phase variant, 26A, which lacks ChoP were screened. The inventors reasoned that this process may result in an anti-ChoP monoclonal antibody that may have characteristics superior to TEPC-15. Unexpectedly, 180/183 antibodies lost reactivity with pili expressed by the 26A variant, the 26A phase variant being derived from C311#3. This variant expresses pili on the surface of the cell at the same level as wild type (as determined by whole cell ELISA and EM). It has an identical pilin subunit amino acid sequence as the wild type strain and retains wild type glycosylation. The only difference between wild type and 26A detectable was the absence of the ChoP structure. The inventors interpretation of this data, derived from hybridomas from fusions from several different mice, is that either the ChoP epitope(s) elicits a disproportionately strong immune response compared to polypeptide and oligosaccharide epitopes in the same molecule or the position of the ChoP on pili (unknown) is surface exposed and is preferentially recognized in whole cell ELISA or a combination of these two factors. In either case, these significant results indicate that ChoP is an important factor in immune response to and immune recognition of pili on the surface of *Neisseria*. As expression of the ChoP on pili can randomly switch on and off, the immune response elicited against epitopes comprised of ChoP may represent a mechanism of immune evasion.

Immunogenicity Trial

The same antigens used above in the development of monoclonal antibodies are scheduled for antigenicity trials to determine whether a short cut (cf. the development of monoclonal antibodies) can be taken by determining if antibodies of desired specificity are generated in polyclonal sera. Antigen (both pure protein and unmodified peptide, described above) from C311#3 and C311#3 pptA will be used to immunize Balb/C mice (mice, 10 per group, vaccinated with 5 µg of protein/peptide+MPL (or similar adjuvant—we used Freunds in the rabbit and mouse experiments) at days 0, 21 and 28 and sacrificed on day 35). Immune response is monitored by ELISA, as above, and by Western blot analysis. The serum produced is tested in BC assay with the capsulate, wild-type C311#3 and the derivative that expresses pili that lacks the ChoP modification site region. Differences in titre between these two will be due to the action of ChoP modification site-specific antibodies in the polyclonal sera. If data suggest that beneficial antibodies are being produced, then improvements to the response using the approaches described above will be sought. Heterologous strains that express the same basal (serine-linked) monosaccharide in their wild-type structure, but with significant amino acid sequence differences (outside the core, conserved region underlying the glycosylation site) will be selected. In this way, the assay will be biased towards detection of antibodies with BC activity that recognize epitopes comprised of both peptide and saccharide. If data suggest that beneficial antibodies are being produced, then improvements to the response using in the approaches described above will be sought.

Example 4

We have identified AniA, an anaerobically induced nitrite reductase, which is glycosylated by the same pathway. This demonstrates that the pilin glycosylation pathway is a general pathway for O-glycosylation in pathogenic *Neisseria*. AniA is known to be an immunogenic outer membrane protein, and glycosylation of this protein with the same phase variable structure that is found on pilin may serve an immunoevasion role. Removal or modification of the glycan or the glycosylated region may lead to a non-native, protective immune response.

Identification of AniA as a Glycoprotein

Figure 3:
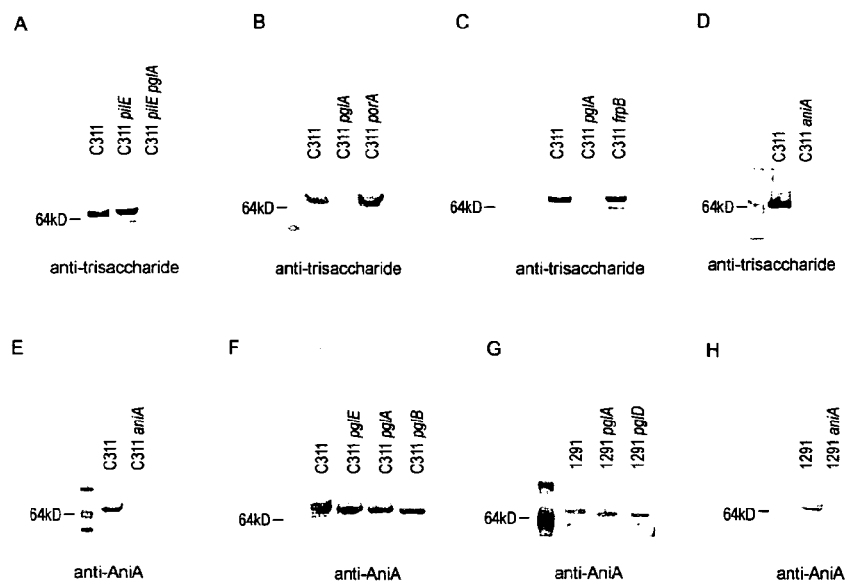
FIG. 3 Identification of AniA as a glycoprotein in *N. meningitidis* and *N. gonorrhoeae* by SDS-PAGE and Western blot analysis. (A-D) Analysis of Outer membrane Proteins (OMPs) of *N. meningitidis* C311 and mutant strains C311pilE, C311pglA, C311porA, C311frpB and C311 aniA on Western blot. Glycoproteins with addition of trisaccharides were revealed by the use of polyclonal antibody anti-trisaccharide. (E) Analysis of C311 and C311aniA by Western blot against monocloncal antibody AniA. (F) Western blot analysis of the migration of AniA isolated from *N. meningitidis* strain C311, and glycosylation pathway mutant strains C311pglE, C311pglA and C311pglB, and (G) *N. gonorrhoeae* strain 1291, glycosylation pathway mutant strains 1291pglA and 1291pglD. AniA was identified by the use of a monoclonal antibody "anti-AniA". (H) Analysis of 1291 and 1291aniA by Western blot against monocloncal antibody anti-AniA.

Western blotting using anti-trisaccharide antisera (Power et al., 2003 Molecular Microbiology 49: 833) revealed a high molecular weight band in strain C311 that disappeared in a C311pglA strain (FIG. 3A; glycosylation pathway mutant), suggesting that there was an additional glycoprotein to pilin which migrates at ~17 kDa. This band was still present in a C311pilE mutant strain (cannot make pilin) therefore the glycoprotein could not be aberrantly migrating pilin (FIG. 3A). To identify the protein the region of the gel containing the reactive protein was isolated and subject to tryptic cleavage and peptide mass analysis by mass spectrometry. Three candidate proteins were identified: PorA, the major outer membrane porin of *N. meningitidis*, FrpB, an outer membrane protein required for iron uptake, and AniA an outer membrane protein with nitrite reductase activity.

Mutations were made in each candidate gene and these mutant alleles transferred to the chromosome using established methods (eg. Power et al., 2003 Molecular Microbiology 49: 833). The band identified by the anti-trisaccharide sera was still present in the C311porA and C311frpB mutant strains (FIGS. 3B and 3C, respectively) but was lost in the C311aniA mutant, indicating that AniA may be the glycoprotein (FIG. 3D). Using and anti-AniA antibody (Cardinale et al., 2000 Infection and Immunity 68: 4368) it was demonstrated that the C311aniA mutant did not express AniA (FIG. 3E). In a series of mutants in the pilin glycosylation pathway, pglE, pglA and pglB, which result in truncation of the pilin linked glycan from a trisaccharide (wild type C311) to a di-saccharide (C311pglE) to a monosaccharide (C311pglA) to no saccharide (C311pglB), the AniA protein has a stepwise reduction in apparent molecular weight (FIG. 3F) consistent with it being a glycoprotein that is post-translationally modified by the same pathway as pilin. A similar increased migration is seen when AniA of *N. gonorrhoeae* is examined by Western blot in wild type strain 1291, compared to 1291pglA (monosaccharide) and 1291pglD (no glycosylation) (FIG. 3G). This indicates that AniA is also a glycoprotein in *N. gonorrhoeae*.

Sequencing of 41 *N. meningitidis* strains revealed that 38% of strains contained a frame shift mutation that would result in premature termination of the protein. Typical examples are shown in FIG. 4A. Analysis of two of the *N. meningitidis* strains containing the frame shift mutation, 1000 and NGP20, revealed that these strains did not express the AniA protein in Western blot analysis (FIG. 4B) and did not have nitrite utilization activity and behaved like a C311aniA mutant (FIG. 4C). This suggests that all other strains with the same allele also lack AniA expression, indicating that AniA expression has been lost in a significant minority of *N. meningitidis* isolates. In contrast, all *N. gonorrhoeae* strains tested had the wild type allele, suggesting that AniA has a key role in *N. gonorrhoeae* biology.

Comparison of the deduced amino acid sequence of the 41 *N. meningitidis* strains reveals a number of differences. These are shown graphically in FIG. 4E (data compiled from FIGS. 5A and 5B). Examination of the position of these differences (Red; FIG. 4FGH), show that they are all on the outer face of the protein, suggesting they may have been generated for by immune selective pressure. Furthermore, theoretical translations of the strains containing the frame shifted AniA gene reveal further differences also on the outer face of the protein (Orange; FIG. 4FGH).

Taken together, these data suggest that immune selective pressure has selected for both the amino acid sequence polymorphisms and silencing of the gene in 38% of *N. meningitidis* strains. The conservation that this protein is glycosylated by a phase variable glycan via the same pathway as pilin adds further evidence that this protein may be under immune selection. The glycosylation is not required for AniA function, as a truncated glycan expressed by AniA in a C311pglA strain has no difference in nitrite utilization activity compared to wild type C311 (see FIG. 4C).

AniA is Glycosylated in the Carboxy Terminal Region.

Figure 6:
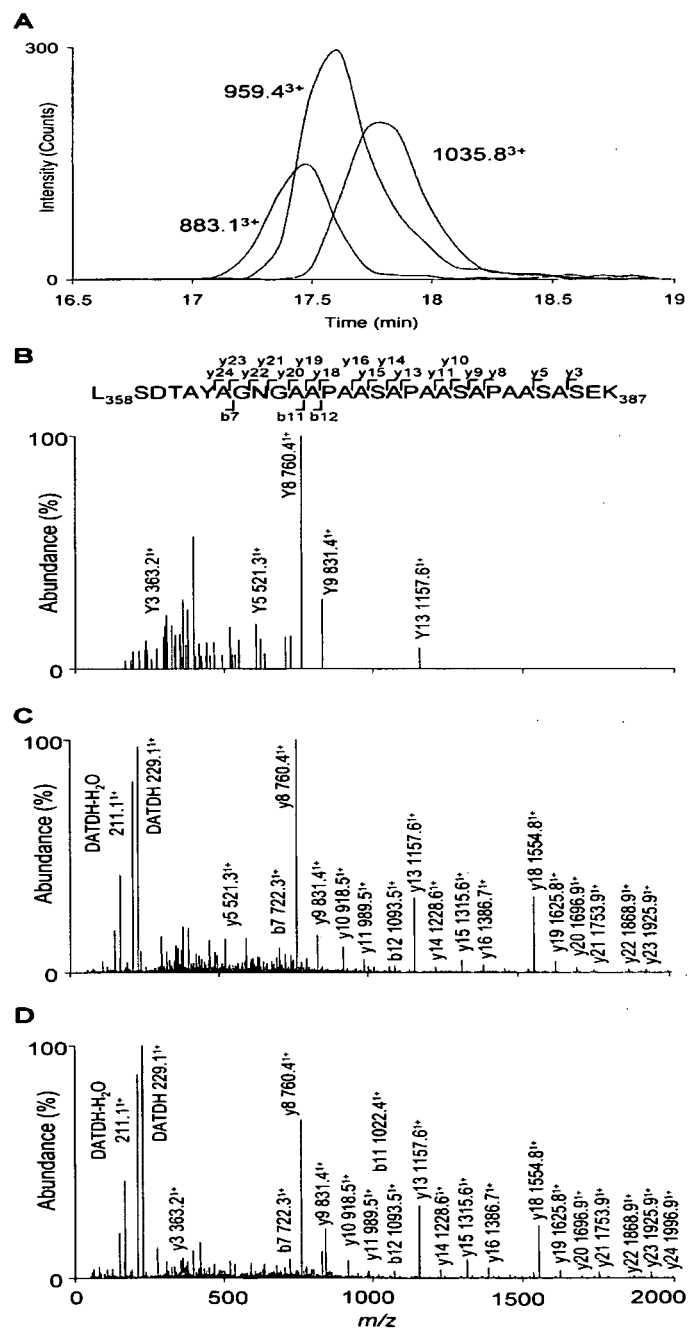
FIG. 6 Tryptic peptides and glycopeptides from flag tagged AniA purified from *N. meningitidis* strain C311pglA cells analysed by LC-ESI-MS/MS.

In order to investigate the location of the glycosylation of AniA, an AniA::flag tag fusion was made and placed on the chromosome to allow expression and affinity purification of AniA from various mutant backgrounds. The approach used was the same as in previous studies with 6×HIS-tagged pilin (Dieckelmann et al., 2003 Protein Expression and Purification 30:69-77) except the flag peptide (DYKDDDDK) was used instead of 6×HIS. MS analysis confirmed that there were multiple glycans covalently linked to a C-terminal peptide consisting of a repeating tetrapeptide (see FIG. 6B). One of the residues in the repeating peptides is serine, and these serines are the only possible candidates for the location of the O-linked glycan.

Figure 7:
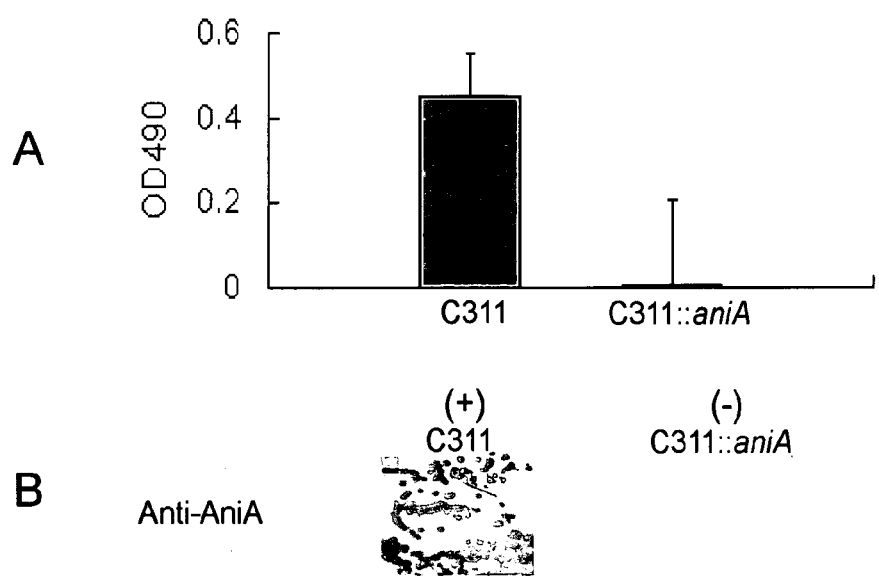
FIG. 7 Analysis of the surface expression of AniA by whole cell ELISA and immuno-colony blot. (A) Whole cell ELISA on AniA from wild-type C311 (blue) and mutant C311aniA (red) by the use of monoclonal antibody anti-AniA. The results are the mean of triplicates. Error bar indicates ±1 standard deviation from the mean. (B) Immuno-colony blot against monoclonal antibody anti-AniA from wild-type C311 (left) and mutant C311aniA (right).
Figure 9:
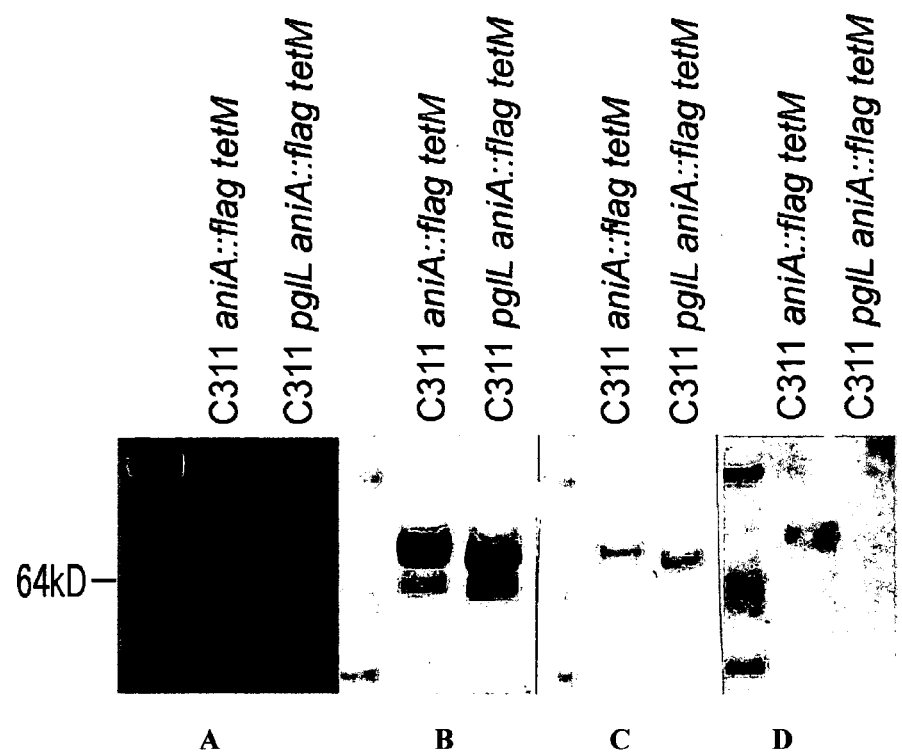
FIG. 9 Western blot analysis of AniA-FLAG. AniA-FLAG purified from wild type C311 and C311pglL were loaded on 4-12% Bis-tris Novex gel and analysed by (A) commassie staining and (B) Western blots with anti-FLAG, (C) anti-AniA mAb and (D) anti-trisaccharide sera.
Figure 11:
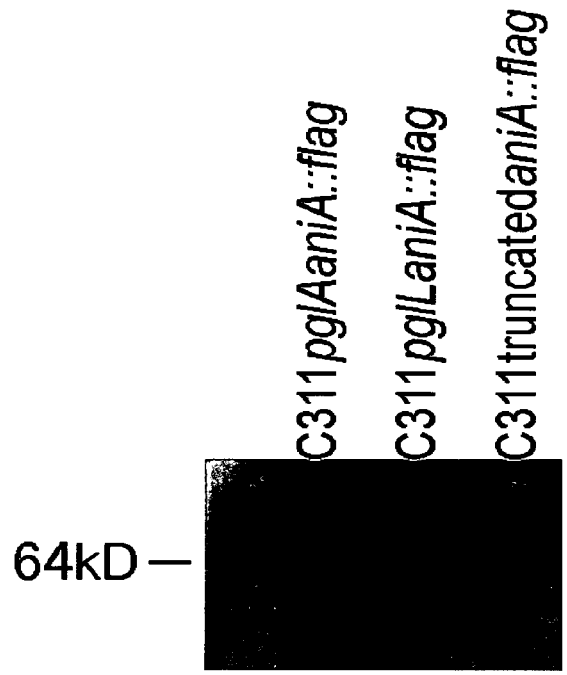
FIG. 11 Western blot analysis of AniA-FLAG antigen for immunisation of mice. AniA-FLAG purified from wild type C311, C311pglA and C311pglL were loaded on 4-12% Bis-tris Novex gel and analysed by Western blot with anti-AniA mAb.
Figure 12:
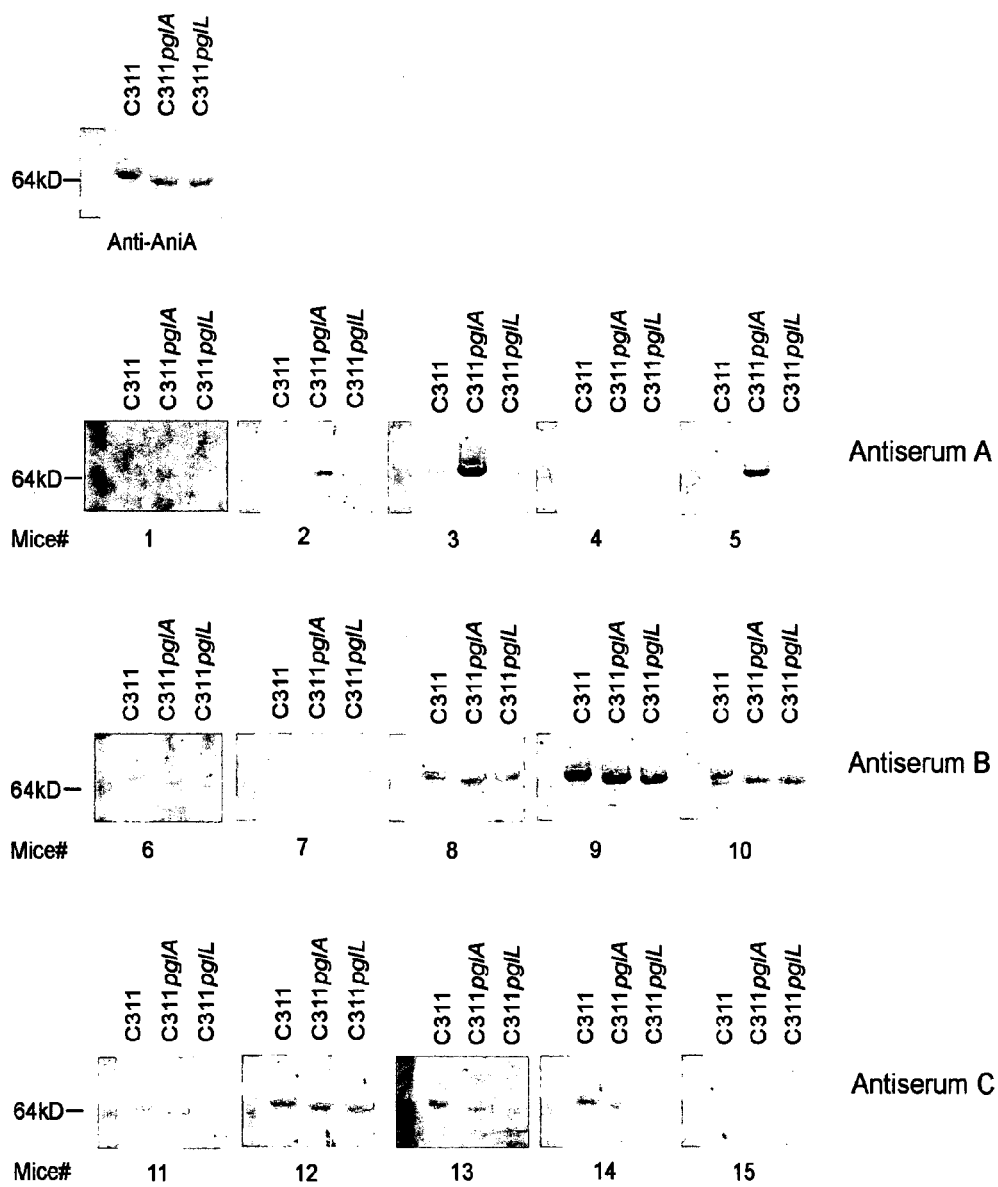
FIG. 12 Western blot analysis immune response against outer membrane proteins preparations from C311, C311pglA and C311pglL using mouse antisera raised against purified flag tagged antigens; (A) AniA-PglA, (B) truncated AniA and (C) AniA-PglL.

The crystal structure of AniA was determined using a recombinant protein expressed in *E. coli* that had the N- and C-regions deleted, including the glycosylated region, so there is no structural data on this domain of the AniA protein. However, the C-terminus (cyan; FIG. 4FGH) does emerge from the "core protein" in a cleft adjacent to the majority of the observed amino acid sequence polymorphisms, and may indicate that the C-terminus is exposed on the surface of the wild type AniA protein. Whole cell ELISA (FIG. 7A) and colony immunoblot (FIG. 7B) of cells indicated that the AniA protein is exposed on the surface of the bacterial cell.

Vaccines Comprising Glycosylation Modified Mutant AniA.

AniA of pathogenic *Neisseria* is know to be immunogenic protein, and may have key roles in anaerobic growth. An immune response against AniA may be effective in preventing disease or colonization of the host by inducing antibodies with bactericidal or opsonophagocytic activity. An immune response directed at AniA may also induce antibodies with functional blocking activities. The discovery that AniA is a glycoprotein, and that it is likely that the covalent linkage of a surface exposed phase variable glycan may act as a mechanism for immunoevasion, provides opportunities to develop recombinant antigens that will elicit a non native immune response. These antigens may be of several types. Firstly, the full length AniA protein expressed in *Neisseria* that is affinity purified (as above), or AniA enriched membrane vesicle where AniA is expressed from a strong promoter, or fragments of AniA expressed in *Neisseria* or generated by proteolytic cleavage after purification. AniA may also be expressed in a heterologous expression system like *E. coli*. In this system, if post-translational modifications are required pgl genes may be expressed in *E. coli* to provide desired components of the glycosylation pathway. The AniA antigen may also be made as a synthetic peptide.

To generate a non-native response to conserved epitopes, AniA antigens with truncated glycans may be prepared. One example is a monosaccharide where AniA antigen can be purified from a set of strains that make all 4 known variations of the basal sugar that is O-linked to Serine. For example DATDH can be modified depending on whether the strain is expressing the pglB1 or pglB2 allele (Power et al., 2003 Molecular Microbiology 49: 833; Chamot-Rooke et al., 2007 PNAS 104: 14783-14788), and whether pglI is phase varied ON or OFF (Warren et al., 2004 FEMS Medical Microbiology and Immunology 41:43-50; Chamot-Rooke et al., 2007 PNAS 104: 14783-14788).

A further example is an AniA antigen expressed with no glycans, either from pglF or pglL or similar *Neisseria* strains, or from *E. coli*, which lacks the glycosylation pathway.

Another further example is an AniA antigen where all or part of the C-terminal glycosylated region is deleted to remove the variable antigen portion of the protein.

Example 5

Construction and, Expression of FLAG-Tagged AniA from *N. meningitidis* Strain C311

Sequence encoding a FLAG tag (N-Asp-Tyr-Lys-Asp-Asp-Asp-Asp-Lys-C) was inserted at the C-terminus of the aniA gene in C311. Vector pT7blueaniA::flagtetMB was constructed by overlap PCR using the primers aniA_F, NMB1624_R, 3' flag_XhoI_ds and NMB1624_F_XhoI. The 3' flag_XhoI_ds primer encoded a FLAG-tag extension followed by a stop codon to allow incorporation of the tag in frame with aniA. The aniA::flag construct with NMB1624 (downstream of aniA) was initially cloned into pT7blue (Novagen) to create pT7blueaniA::flag. A tetracycline antibiotic resistant cassette (TetMB) was digested with SalI and cloned into XhoI linearised pT7blueaniA::flag to create pT7blueaniA::flag tetMB, which was transformed to the chromosome of C311 by homologous recombination as described (Jennings et al., 1995 *Microb Pathol* 19: 391-407). The genomic DNA of pT7blueaniA::flag tetMB was transformed to C311#3pglA and C311#3pglL using the above method for AniA with truncated glycan (i.e. monosaccharides and no glycan respectively). Expression of FLAG-tagged truncated AniA was achieved with the same approach described above but using primer aniA3'flag_trunc2 instead of 3'flag_XhoI_ds. The truncated FLAG-tagged AniA is shown in FIG. 9.

Characterisation of Antigen for Animal Immunization.

The FLAG-tagged AniA antigen and the truncated FLAG-tagged AniA antigen were purified according to manufacturer's instruction with 3% of Tween 20. The antigens purified are characterised with Western blot analysis using anti-FLAG, anti-AniA mAb and anti-trisaccharide sera (FIG. 9).

Rabbit Immunogenicity Trial.

Production of antisera specific for AniA with truncated glycosylation (AniA-PglA) were raised in rabbit, as essentially described in Power et al. (2000 Microbiology 146: 967-979). AniA-PglA antigen is prepared as described above. The immune response was monitored by Western blot analysis (FIG. 10).

Mouse Immunogenicity Trial.

Production of antisera specific for AniA with truncated glycan (AniA-PglA), deglycosylated AniA (AniA-PglL) and truncated AniA were raised in mice, In brief, purified AniA antigen from truncated glycan strains (C311pglA and C311pglL) will be used to immunise Balb/C mice (Mice, 5 per group, vaccinated with 5 ug of protein+Freunds at days 0, 21 and 28 and sacrificed on day 35). The immune response was monitored by western blot analysis.

In Vivo Nitrite Utilisation Assays.

Cells may be grown to OD 0.5 $A_{600}$, washed once in PBS containing 27.8 mM glucose, then resuspended to an OD of 1 in 10 ml of the same solution. After equilibration at 37° C. for 30 mins, heat-inactivated mouse antiserum may be added in 1/100 dilution and $NaNO_2$ was added to the cultures to a final concentration of 1 mM. Nitrite utilization may be assayed colourimetrically with the Griess reagent (Green et al., 1982 *Biochem.* 126: 131-138) essentially as described by Anjum et al. (2002 *J Bacteriol.* 184: 2984-2993). 100 μA of each sample is collected for assay every 10 min for 1 hour. 50 μl of 1% sulphanilamide was added to the samples, and the reaction iss started with the addition of 100 μl of a 0.02% solution of N-naphthylenediamine. The reaction is followed by measuring absorbance at 540 nm.

Results

The data shown in FIGS. 11 and 12 demonstrate that as prediced, glycosylated AniA elicited a strong antibody response. More particularly, this antibody response was largely directed to glycosyl moieties, even in the case of AniA proteins having modified glycosylation (eg. in C311 pglA and pglL bacteria). Most striking was the strong antibody response to the truncated AniA protein lacking glycosylation (SEQ ID NO:1). Antibodies generated by this response (Antiserum B) recognized AniA independenty of the presence or absence of AniA glycosylation.

Example 6

Given the results in Examples 5 which demonstrated the immunogenicity of truncated AniA protein fragments completely lacking glycosylation, it is proposed that such fragments may be readily expressed in "standard": expression bacterial host cells such as *E. coli* that do not glycosylate the protein. This obviates the need to use more specialized bacteria (such as the genetically-modified *N. meningitidis* strains mentioned previously) that can partially-glycosylate the protein.

Expression of Truncated AniA in *E. coli*

Truncated AniA proteins were amplified from *N. gonorrhoeae* strain 1291 using primers listed in tableXX. Truncated AniA #1 were amplified using primers ExpAniA_NdeI_F and ExpAniA_BamHI_E_R; Truncated AniA #2 using ExpAniA_NdeI_F and ExpAniA_BamHI_M_R; Truncated AniA #3 using ExpAniA_NdeI_F and ExpAniA_BamHI_G_R; Truncated AniA #4 using ExpAniA_NdeI_F and ExpAniA_BamHI_Y_R; Truncated AniA #5 using ExpAniA_NdeI_E_F and ExpAniA_BamHI_E_R; Truncated AniA #6 using ExpAniA_NdeI_E_F and ExpAniA_BamHI_M_R; Truncated AniA #7 using ExpAniA_NdeI_E_F and ExpAniA_BamHI_G_R; Truncated AniA #8 using ExpAniA_NdeI_E_F and ExpAniA_BamHI_Y_R. The amplified sequences encoding truncated AniA is cloned into pET15b expression vector (Novagen) with NdeI and BamHI sites. The truncated HIS-tagged AniA will be purified and his-tag will be cleaved with protease thrombin.

The encoded protein sequences are set forth in SEQ ID NOS:2-9 (FIG. 13).

These non-glycosylated, AniA protein fragments will be tested for immunogenicity as previously described in Example 5.

It will be appreciated by the skilled person that the present invention is not limited to the embodiments described in detail herein, and that a variety of other embodiments may be contemplated which are nevertheless consistent with the broad spirit and scope of the invention.

It will be further appreciated that the principle set forth herein is applicable to any post-translationally modified protein of any pathogenic bacterium.

All patent and scientific literature and computer programs referred to in this specification are incorporated herein by reference in their entirety.

Tables

TABLE 1

Primer sequences

| Primer Name | Sequence (5'→3') |
|---|---|
| aniA_F | ATGAAACGCCAAGCCTTAG |
| NMB1624_R | TTATCGGCTTGTGCAACGGAAGCCC |
| 3'flag_XhoI_ds | AATAACCGGACATACTTCATCTCGAGTCACTTGTCGTCATCGTCCTTGTAGTCATAAACGCTTTTTTCGGATGCAGAGGC |
| NMB1624_F_XhoI | CTCGAGATGAAGTATGTCCGGTTATTTTCC |
| aniA3'flag_trunc2 | TTCATCTCGAGTCACTTGTCGTCATCGTCCTTGTAGTCATAAACCATGATTTCAGGGTTTTCTGC |

TABLE 2

Primer sequences

| Primer Name | Sequence (5'→3') |
|---|---|
| ExpAniA_NdeI_F | CGCACT<u>CATAT</u>GCCGCACAAGCTACCGCCGAA |
| ExpAniA_NdeI_E_F | CGCACT<u>CATAT</u>GAACTGCCCGTCATCGAT |
| ExpAniA_BamHI_E_R | GCGTCC<u>GGATCC</u>TTACTCTACTTTCAATTGCCC |
| ExpAniA_BamHI_M_R | GCGTCC<u>GGATCC</u>TTACATGATTTCAGGGTTTTC |
| ExpAniA_BamHI_G_R | GCGTCC<u>GGATCC</u>TTAGCCGCTGCCGGCGTAAGC |
| ExpAniA_BamHI_Y_R | GCGTCC<u>GGATCC</u>TTATTAATAAACGCTTTTTTC |

*Restriction site is indicated by underlying letter.

The invention claimed is:

1. A method of eliciting an immune response to a bacterial pathogen of the genus *Neisseria* in a host, said method including the step of administering to said host an immunogenic composition comprising an isolated mutant *Neisseria* nitrite reductase polypeptide that is not glycosylated, wherein the mutant *Neisseria* nitrite reductase polypeptide comprises an amino acid sequence lacking a carboxy-terminal serine-containing tetrapeptide repeat AASA (SEQ ID NO: 113) of a corresponding wild-type *Neisseria* nitrite reductase glycoprotein and elicits a more immunologically effective immune response compared to the corresponding wild-type *Neisseria* nitrite reductase glycoprotein, to thereby elicit an immune response to said bacterial pathogen in said host.

2. The method of claim 1, wherein said host is a mammal.

3. The method of claim 2, wherein said host is a human.

4. The method of claim 1, wherein the immune response prophylactically or therapeutically treats an infection by a bacterial pathogen of the genus *Neisseria*.

5. The method of claim 4, wherein said bacterial pathogen is *Neisseria meningitidis* or *Neisseria gonorrhoeae*.

6. The method of claim 1, wherein the isolated mutant nitrite reductase polypeptide comprises an amino acid sequence selected from SEQ ID NOs: 1-4 or 6-8.

7. The method of claim 1, wherein the immunogenic composition further comprises a carrier, diluent or excipient.

8. The method of claim 6, wherein the isolated mutant nitrite reductase polypeptide consists of the nitrite reductase polypeptide amino acid sequence of any one of SEQ ID NOs: 1-4 or 6-8.

9. The method of claim 1, wherein the isolated mutant nitrite reductase polypeptide further lacks an N-terminal amino acid sequence of the corresponding wild-type polypeptide.

10. The method of claim 1, wherein the carboxy-terminal serine-containing tetrapeptide repeat AASA (SEQ ID NO: 113) is located within amino acids 355-390 of SEQ ID NOs: 31-34, 74, or 75.

* * * * *